US010273511B2

(12) United States Patent
Lemke et al.

(10) Patent No.: US 10,273,511 B2
(45) Date of Patent: Apr. 30, 2019

(54) ENZYMES FOR PRODUCING NON-STRAIGHT-CHAIN FATTY ACIDS

(71) Applicant: WISCONSIN ALUMNI RESEARCH FOUNDATION, Madison, WI (US)

(72) Inventors: Rachelle A. S. Lemke, Madison, WI (US); Timothy James Donohue, Middleton, WI (US); Joshua J. Coon, Middleton, WI (US); Amelia C. Peterson, Bremen (DE); Michael S. Westphall, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/755,213

(22) Filed: Jun. 30, 2015

(65) Prior Publication Data

US 2015/0376659 A1 Dec. 31, 2015

Related U.S. Application Data

(60) Provisional application No. 62/018,939, filed on Jun. 30, 2014.

(51) Int. Cl.
| | | |
|---|---|---|
| *C12P 7/64* | (2006.01) |
| *C12N 1/21* | (2006.01) |
| *C12N 1/12* | (2006.01) |
| *C12N 1/15* | (2006.01) |
| *C12N 9/10* | (2006.01) |
| *C12P 17/04* | (2006.01) |

(52) U.S. Cl.
CPC .......... *C12P 7/6409* (2013.01); *C12N 9/1007* (2013.01); *C12P 17/04* (2013.01)

(58) Field of Classification Search
None
See application file for complete search history.

(56) References Cited

U.S. PATENT DOCUMENTS

| | | | |
|---|---|---|---|
| 7,371,420 B2 | 5/2008 | Piccirilli | |
| 8,003,390 B2 | 8/2011 | Donohue et al. | |
| 8,426,620 B2 | 4/2013 | Kim et al. | |
| 2007/0141591 A1* | 6/2007 | Borns | C12N 9/1252 435/6.18 |

OTHER PUBLICATIONS

UniProt Accession No. Q3J4I7, May 2013, 1 page.*
UniProt Accession No. Q3IYV7, May 2013, 1 page.*
UniProt Accession No. Q3IYV8, May 2013, 1 page.*
Whisstock et al., Quarterly Rev. Biophys. 36:307-340, 2003 (Year: 2003).*
Seffernick et al., J. Bacteriol. 183:2405-2410, 2001 (Year: 2001).*
Witkowski et al., Biochemistry 38:11643-11650, 1999 (Year: 1999).*
Anthony JR, Warczak KL, & Donohue TJ (2005) A transcriptional response to singlet oxygen, a toxic byproduct of photosynthesis. *Proc Natl Acad Sci U S A* 102(18):6502-6507.
Anthony JR, Newman JD, & Donohue TJ (2004) Interactions between the *Rhodobacter sphaeroides* ECF sigma factor, $\sigma^E$, and its anti-sigma factor, ChrR. *J. Mol. Biol.* 341:345-360.
Armstrong G & Hearst J (1996) Carotenoids 2: Genetics and molecular biology of carotenoid pigment biosynthesis. The *FASEB Journal* 10(2):228-237.
Baba T, et al. (2006) Construction of *Escherichia coli* K-12 in-frame, single-gene knockout mutants: the Keio collection. *Molecular systems biology* 2:2006 0008.
Batna, A.; Spiteller, G. Oxidation of Furan-containing fatty acids by Soybean Lipoxygenase-1 in the Presence of Linoleic Acid. Chem. Phys. Lipids, 1994, 70, 179-185.
Bethesda-Research-Laboratories (1986) BRL pUC host: *Escherichia coli* DH5α competent cells. *Bethesda Research Laboratories Focus* 8:9-10.
Chang YY & Cronan JE, Jr. (1999) Membrane cyclopropane fatty acid content is a major factor in acid resistance of *Escherichia coli*. *Mol Microbiol* 33(2):249-259.
Christie W (2010) Lipid Analysis. ed P.J. Barnes & Associates (Eds.) (The Oily Press, Bridgwater), p. 148.
Christie W (2014) Fatty Acids: Hydroxy and other oxygenated structures, occurrence and biochemistry, © lipidlibrary.aocs.org.
Cogdell RJ (2000) How carotenoids protect bacterial photosynthesis. *Phil. Trans. R. Soc. Lond. B* 355:1345-1349.
Connor MR & Liao JC (2009) Microbial production of advanced transportation fuels in non-natural hosts. *Current Opinion in Biotechnology* 20(3):307-315.
Courtois F, Guerard C, Thomas X, & Ploux O (2004) *Escherichia coli* cyclopropane fatty acid synthase. *European journal of biochemistry / FEBS* 271(23-24):4769-4778.
Cronan JE (2002) Phospholipid modifications in bacteria. *Curr. Opin. Microbiol.* 5:202-205.
Cronan JE (2003) Bacterial membrane lipids: Where Do We Stand? *Annual Review of Microbiology* 57(1):203-224.

(Continued)

*Primary Examiner* — David Steadman
(74) *Attorney, Agent, or Firm* — Daniel A. Blasiole; DeWitt LLP

(57) ABSTRACT

Enzymes for producing non-straight-chain fatty acids, microorganisms comprising the enzymes, and in vivo and in vitro uses of the enzymes. Provided are enzymes capable of producing various non-straight-chain fatty acids, including branched-chain fatty acids, cyclic fatty acids, and furan-containing fatty acids. The enzymes include RSP2144, RSP1091, and RSP1090 from *Rhodobacter sphaeroides* and homologs thereof. The enzymes can be purified to produce non-straight-chain fatty acids in vitro or expressed in microorganisms to produce non-straight-chain fatty acids in vivo. The microorganisms can be fine-tuned to produce a specific type of non-straight-chain fatty acid by expressing, overexpressing, or deleting the enzymes in various combinations.

34 Claims, 21 Drawing Sheets

Specification includes a Sequence Listing.

(56) References Cited

OTHER PUBLICATIONS

Donohue TJ, Cain BD, & Kaplan S (1982) Purification and characterization of an N-acylphosphatidylserine from *Rhodopseudomonas sphaeroides*. *Biochemistry* 21(11):2765-2773.

Dufour YS, Landick R, & Donohue TJ (2008) Organization and evolution of the biological response to singlet oxygen stress. *J Mol Biol* 383(3):713-730.

Fuchs, C.; Spiteller, G. Iron Release from the Active Site of Lipoxygenase, Z.Naturforsch. 2000, 55, 643-648.

Girotti AW & Kriska T (2004) Role of lipid peroxides in photo-oxidative stress signalling. *Antioxidants & Redox Signalling* 6:301-310.

Glaeser J, Nuss AM, Berghoff BA, & Klug G (2011) Singlet oxygen stress in microorganisms. *Advances in Microbial Physiology*, ed Robert KP (Academic Press), Vol vol. 58, pp. 141-173.

Glass, R. L.; Krick, T. P.; Olson, D. L.; Thorson, R. L. The Occurrence and Distribution of Furan-containing fatty acids in Spawning Male Freshwater Fish. Lipids, 1977, 12, 828-836.

Glass, R. L.; Krick, T. P.; Sand, D. M.; Rahn, C. H.; Schlenk, H. Furanoid Fatty Acids from Fish Lipids. Lipids, 1975, 10, 695-702.

Glass, R. L.; Krick, T. P.; Eckhardt, A. E. New Series of Fatty Acids in Northern Pike (Esox Indus). Lipids, 1974, 9, 1004-1008.

Graft, G.; Gellerman, J. L.; Sand, D. M.; Schlenk, H. Inhibition of Blood Platelet Aggregation by Dioxo-ene Compounds. Biochim. Biophys. Acta, 1984, 799, 143-150.

Greenwell RS, Nam TW, & Donohue TJ (2011) Aspects of the zinc metalloprotein ChrR required for dissociation of $\sigma^E$/ChrR complexes. *Journal of Molecular Biology* 407:477-491.

Grogan DW & Cronan JE (1997) Cyclopropane ring formation in membrane lipids of bacteria. Microbiology and Molecular Biology Reviews 61(4):429-441.

Guianvarc'h D, Drujon T, Leang TE, Courtois F, & Ploux O (2006) Identification of new inhibitors of *E. coli* cyclopropane fatty acid synthase using a colorimetric assay. *Biochimica et Biophysica Acta (BBA)—Proteins and Proteomics* 1764(8):1381-1388.

Gunstone, F. D.; Wijesundera, R. C.; Scrimgeour, C. M. The Component Acids of Lipids from Marine and Freshwater Species with Special Reference to Furan-Containing Acids. J. Sci. Food Agric. 1978, 29, 539-550.

Halliwell, B.; Gutteridge, J. M. C. Role of Free Radicals and Catalytic Metal Ions in Human Disease: An Overview, Methods Enzymol. 1990, 186, 1-85.

Hands AR & Bartley W (1962) The fatty acids of *Rhodopseudomonas* particles. *The Biochemical journal* 84:238.

Hannemann, K.; Puchta, V.; Simon, E.; Ziegler, H.; Ziegler, G.; Spiteller, G. The Common Occurrence of Furan-containing fatty acids in Plants. Lipids, 1989, 24, 296-298.

Imlay JA (2003) Pathways of oxidative damage. *Annu. Rev. Microbiol.* 57:395-418.

Iwig DF, Uchida A, Stromberg JA, & Booker SJ (2005) The activity of *Escherichia coli* cyclopropane fatty acid synthase depends on the presence of bicarbonate. *Journal of the American Chemical Society* 127(33):11612-11613.

Jandke, J.; Schmidt, J.; Spiteller G. Über das Verhalten von F-Sauren bei der Oxidation mit Lipoxydase in Anwesenheit von SH-haltigen Verbindungen, liebigs Ann. Chem. 1988, 29-34.

Kontur WS, et al. (2012) Revised sequence and annotation of the *Rhodobacter sphaeroides* 2.4.1 genome. *Journal of Bacteriology* 194:7016-7017.

Koopman WJ, et al. (2010) Mammalian mitochondrial complex I: biogenesis, regulation, and reactive oxygen species generation. *Antioxid Redox Signal* 12(12):1431-1470.

Krinsky NI (1989) Antioxidant functions of carotenoids. *Free radical biology & medicine* 7(6):617-635.

Lands B (2012) Consequences of Essential Fatty Acids. *Nutrients* 4(9):1338-1357.

Lemke RA, Peterson AC, Ziegelhoffer EC, Westphall MS, Tjellström H, Coon JJ, Donohue TJ. Synthesis and scavenging role of furan fatty acids. *Proc Natl Acad Sci U S A*. Aug. 19, 2014;111(33):E3450-7.

Lennen RM, Braden DJ, West RA, Dumesic JA, & Pfleger BF (2010) A process for microbial hydrocarbon synthesis: Overproduction of fatty acids in *Escherichia coli* and catalytic conversion to alkanes. *Biotechnol Bioeng* 106(2):193-202.

Mackenzie C, et al. (2001) The home stretch, a first analysis of the nearly completed genome of *Rhodobacter sphaeroides* 2.4.1. *Photosynth Res* 70(1):19-41.

Magnuson K, Jackowski S, Rock CO, & Cronan JE (1993) Regulation of fatty acid biosynthesis in *Escherichia coli*. *Microbiological Reviews* 57(3):522-542.

Michaud AL, Diau G-Y, Abril R, & Brenna JT (2002) Double bond localization in minor homoallylic fatty acid methyl esters using acetonitrile chemical ionization tandem mass spectrometry. *Analytical Biochemistry* 307(2):348-360.

Montanari C, Sado Kamdem SL, Serrazanetti DI, Etoa FX, & Guerzoni ME (2010) Synthesis of cyclopropane fatty acids in *Lactobacillus helveticus* and *Lactobacillus sanfranciscensis* and their cellular fatty acids changes following short term acid and cold stresses. *Food microbiology* 27(4):493-502.

Morris, L. J.; Marshall, M. O.; Kelly, W. A Unique Furanoid Fatty Acid from Exocarpus seed oil. Tetrahedron Lett. 1966, 16, 4249-4253.

Mueller S, et al. (2008) General detoxification and stress responses are mediated by oxidized lipids through TGA transcription factors in *Arabidopsis*. *Plant Cell* 20(3):768-785.

Nam TW, Ziegelhoffer EC, Lemke RAS, & Donohue TJ (2013) Proteins needed to activate a transcriptional response to the reactive oxygen species singlet oxygen. *mBio* 4(1):e00541-00512.

Newman JD, Falkowski MJ, Schilke BA, Anthony LC, & Donohue TJ (1999) The *Rhodobacter sphaeroides* ECF sigma factor, $\sigma^E$, and the target promoters cycA P3 and rpoE P1. *J Mol Biol* 294(2):307-320.

Nuss AM, et al. (2013) DegS and RseP homologous proteases are involved in singlet oxygen dependent activation of RpoE in *Rhodobacter sphaeroides*. *PLoS ONE* 8(11):e79520.

Okada Y, Okajima H, & Konishi H (1990) Antioxidant effect of naturally occurring furan-containing fatty acids on oxidation of linoleic acid in aqueous dispersion. *Journal of the American Oil Chemists' Society (JAOCS)* 67:858-862.

Olins PO, Rangwala SH. A novel sequence element derived from bacteriophage T7 mRNA acts as an enhancer of translation of the lacZ gene in *Escherichia coli*. *J Biol Chem*. Oct. 15, 1989;264(29):16973-6.

Peralta-Yahya PP, Zhang F, del Cardayre SB, & Keasling JD (2012) Microbial engineering for the production of advanced biofuels. *Nature* 488(7411):320-328.

Peterson AC, et al. (2014) Development of a GC/Quadrupole-Orbitrap mass spectrometer, Part I: Design and characterization. *Analytical Chemistry* (Submitted).

Peterson AC, et al. (2014) Development of a GC/Quadruple-Orbitrap mass spectrometer, Part II: New approaches for discovery metabolomics. *Analytical Chemistry* (Submitted).

Qureshi N, Honovich JP, Hara H, Cotter RJ, & Takayama K (1988) Location of fatty acids in lipid A obtained from lipopolysaccharide of *Rhodopseudomonas sphaeroides* ATCC 17023. *J Biol Chem* 263(12):5502-5504.

Rothamer DA, Donohue TJ. Chemistry and combustion of fit-for-purpose biofuels. *Curr Opin Chem Biol*. Jun. 2013;17(3):522-8.

Rouser G, Fkeischer S, & Yamamoto A (1970) Two dimensional then layer chromatographic separation of polar lipids and determination of phospholipids by phosphorus analysis of spots. *Lipids* 5(5):494-496.

Russell NJ & Harwood JL (1979) Changes in the acyl lipid composition of photosynthetic bacteria grown under photosynthetic and non-photosynthetic conditions. *The Biochemical journal* 181(2):339-345.

Sayre LM, De L, Quan Y, Xiaochun Z, & Xiaoxia T (2006) Protein adducts generated from products of lipid oxidation: Focus on HNE and ONE*. *Drug Metabolism Reviews* 38(4):651-675.

(56) References Cited

OTHER PUBLICATIONS

Schilke BA & Donohue TJ (1995) ChrR positively regulates transcription of the *Rhodobacter sphaeroides* cytochrome $c_2$ gene. *Journal of Bacteriology* 177(8):1929-1937.

Schödel, R.; Spiteller, G. Uber die Strukturaufklärung von (Hydroxyoxo-cyclopentenyl) alkansauren, den Aldolkondensationsprodukten von Dioxoen carbonsäuren aus Rinderleber. *Helv. Chim. Acta,* 1985, 68, 1624-1634.

Shirasaka N, Nishi K, & Shimizu M (1995) Occurrence of a furan-containing fatty acid in marine bacteria. *Biochim Biophys Acta.* 1258(3):225-227.

Shirasaka N, Nishi K, & Shimizu S (1997) Biosynthesis of furan-containing fatty acids (F-acids) by a marine bacterium, *Shewanella putrefaciens. Biochimica et biophysica acta* 1346(3):253-260.

Simon R, Priefer U, & Puhler A (1983) A broad host range mobilization system for in vitro genetic engineering: transposon mutagenesis in Gram negative bacteria. *Bio/technology* 1:748-791.

Spiteller G (2005) Furan-containing fatty acids: occurrence, synthesis, and reactions. Are furan-containing fatty acids responsible for the cardioprotective effects of a fish diet? *Lipids* 40(8):755-771.

Tjellström H, Strawsine M, Silva J, Cahoon EB, & Ohlrogge JB (2013) Disruption of plastid acyl:acyl carrier protein synthetases increases medium chain fatty acid accumulation in seeds of transgenic *Arabidopsis. FEBS Letters* 587(7):936-942.

Wakimoto T, et al. (2011) Furan-containing fatty acid as an anti-inflammatory component from the green-lipped mussel *Perna canaliculus. Proceedings of the National Academy of Sciences* 108(42):17533-17537.

Wang AY, Grogan DW, & Cronan JE (1992) Cyclopropane fatty acid synthase of *Escherichia coli:* Deduced amino acid sequence, purification, and studies of the enzyme active site. *Biochemistry* 31(45):11020-11028.

White DC, et al. (2005) Phospholipid furan-containing fatty acids and ubiquinone-8: lipid biomarkers that may protect dehalococcoides strains from free radicals. *Applied and environmental microbiology* 71(12):8426-8433.

Yuan Y, Crane DC, Musser JM, Sreevatsan S, & Barry CE (1997) MMAS-1, the Branch Point Between cis- and trans-Cyclopropane-containing Oxygenated Mycolates in Mycobacterium tuberculosis. *J Biol Chem* 272(15):10041-10049.

Ziegelhoffer EC & Donohue TJ (2009) Bacterial responses to photo-oxidative stress. *Nat Rev Microbiol* 7(12):856-863.

Ishii, K.; Okajima, H.; Okada, Y.; Watanabe, H. Studies on Furan-containing fatty acids of Salmon Roe Phospholipids. J. Biochem. (Tokyo), 1988, 103, 836-839.

Ishii, K.; Okajima, H.; Okada, Y.; Watanabe, H. Effects of Phosphatidylcholines Containing Furan-containing fatty acid on Oxidation in Multilamellar Liposomes. Chem. Pharm. Bull. 1989, 37, 1396-1398.

Okada Y, Kaneko M, & Okajima H (1996) Hydroxyl radical scavenging activity of naturally occurring furan-containing fatty acids. Biological & pharmaceutical bulletin 19(12):1607-1610.

Ota, T.; Takagi, T. Furan-containing fatty acids in the Lipids of the Cresthead Flounder. Nippon Suisan Gakkaishi, 1992, 58, 721-725.

Watabe N, Ishida Y, Ochiai A, Tokuoka Y, & Kawashima N (2007) Oxidation decomposition of unsaturated fatty acids by singlet oxygen in phospholipid bilayer membranes. Journal of Oleo Science 56(2):73-80.

\* cited by examiner

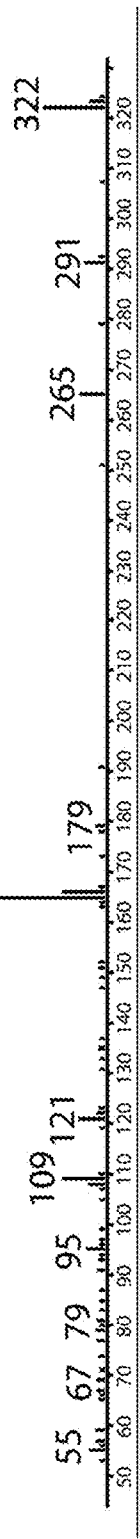
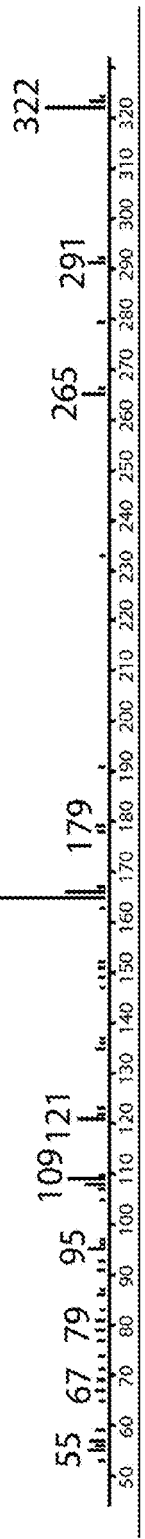
FIG. 6C
FIG. 6D

```
                     Vaccenic  Methylated  Cyclopropene  Furan
Fatty Acids Made  C18:1 ⟶ M-UFA ⟶ Ce-FA ⟶ Fu-FA Gene name                ufaM        ufaC         cfaO
RSP#                     2144        1091         1090
```

FIG. 10

ENZYMES FOR PRODUCING NON-STRAIGHT-CHAIN FATTY ACIDS

STATEMENT REGARDING FEDERALLY SPONSORED RESEARCH

This invention was made with government support under DE-FC02-07ER64494 awarded by the US Department of Energy and GM107199 and GM075273 awarded by the National Institutes of Health. The government has certain rights in the invention.

BACKGROUND

Fatty acids, or the products derived from them, are valuable as food additives, dietary supplements, specialty chemicals, lubricants, fuels, and petroleum substitutes. Fatty acids can be generally classified as straight-chain fatty acids or non-straight-chain fatty acids. Whereas straight-chain fatty acids are relatively abundant, non-straight-chain fatty acids are not. Important classes of non-straight-chain fatty acids include branched-chain fatty acids, furan-containing fatty acids, and cyclic fatty acids.

Branched-chain fatty acids are constituents of the lipids of bacteria and animals. They are sometimes found in the integral lipids of higher plants. The fatty acyl chain on branched-chain fatty acids may be saturated or unsaturated. The branch may be methyl or a higher-order branch. The most common branched-chain fatty acids are monobranched, but di- and poly-branched fatty acids also occur and may be either saturated or unsaturated.

Branched-chain fatty acids are known to have additional preferred properties when compared to straight-chain fatty acids of the same molecular weight (i.e., isomers), such as considerably lower melting points which can in turn confer lower pour points when made into industrial chemicals. These additional benefits allow the branched-chain fatty acids to confer substantially lower volatility and vapor pressure and improved stability against oxidation and rancidity. These properties make branched-chain fatty acids particularly suited as components for feedstock for cosmetic and pharmaceutical applications, or as components of plasticizers for synthetic resins, solvents for solutions for printing ink and specialty inks, and industrial lubricants or fuel additives.

Furan-containing fatty acids are a large group of fatty acids characterized by a furan ring. The furan ring typically carries at one α-position an unbranched fatty acid chain with 9, 11, or 13 carbon atoms and at the other α-position a short straight-chain alkyl group with 3 or 5 carbon atoms (Glass et al. 1975). In most cases, both β-positions of the furan ring are substituted by either one or two methyl residues or other groups. Furan-containing fatty acids without any substitutions on the β-positions of the furan ring also occur (Morris et al. 1966). Furan-containing fatty acids are widely distributed in nature as trace components of plants, fishes, amphibians, reptiles, microorganisms, and mammals, including humans (Glass et al. 1975, Glass et al. 1974, Gunstone et al. 1978, Hannemann et al. 1989, Ishii et al. 1988, Ota et al. 1992).

Furan-containing fatty acids appear to be involved in various important biological functions and act in an antioxidant, antitumoral, and antithrombotic capacity (Ishii et al. 1989, Graft et al. 1984, Okada et al. 1996). The correlation between consumption of fish rich in furan-containing fatty acids and protection against coronary heart disease mortality has been confirmed in several studies (Spiteller 2005). Furan-containing fatty acids have also been reported to have inhibitory effects on blood platelet aggregation (Graft et al. 1984) and to have potential antitumor activity (Ishii et al. 1988). Furan-containing fatty acids prevent oxidation of linoleic acid (Okada et al. 1990) and act as antioxidants in plants (Batna et al. 1994). Some studies have demonstrated that furan-containing fatty acids undergo oxidation by ring opening to form dioxoenes (Jandke et al. 1988, Schodel et al. 1985) in the presence of linoleic acid as a co-substrate, indicating that that furan-containing fatty acids act as radical scavengers (Fuchs et al. 2000, Halliwell et al. 1990). These effects of furan-containing fatty acids make them valuable as dietary supplements for animals, including humans.

Furan-containing fatty acids also have potential use as advanced biofuels, oxygenates, or fuel additives. The presence of the oxygen atom in the fatty acyl chain provides a reactive group for catalytic conversion to branched acyl chains that are useful as fuels. The presence of the oxygen in a hydrocarbon backbone may also enhance combustion or provide a site to control radicals that are formed during fuel combustion (Rothamer et al. 2013).

Cyclic fatty acids typically comprise a 3- to 7-membered ring in the hydrocarbon chain or at the terminus of the hydrocarbon chain. The ring may be saturated (cyclopropane, for example) or unsaturated (cyclopropene, for example). Cyclic fatty acids occur naturally in plants, especially certain seed oils, and microorganisms, but only rarely in animal tissues. Cyclic fatty acids include cyclopropane fatty acids, such as lactobacillic acid and majusculoic acid; cyclopropene fatty acids such as sterculic acid and malvalic acid; and fatty acids with terminal ring structures, such as 11-cyclohexylundecanoic acid, 13-cyclohexyltridecanoic acid, 2-hydroxy-11-cyclohepylundecanoic acid, ladderane fatty acids, chaulmoogric acid, and gorlic acid.

Strategies for obtaining non-straight-chain fatty acids at high quantities are needed.

SUMMARY OF THE INVENTION

The invention provides enzymes and aspects pertaining thereto for producing non-straight-chain fatty acids.

The enzymes of the invention comprise RSP2144 or a homolog thereof, RSP1091 or a homolog thereof, and RSP1090 or a homolog thereof. The RSP2144 or homolog thereof may comprise an ortholog of RSP2144, a homolog of RSP2144 comprising a sequence at least about 90% identical to SEQ ID NO:2, or a homolog of RSP2144 comprising a sequence at least about 90% identical to SEQ ID NO:15. The RSP1091 or homolog thereof may comprise an ortholog of RSP1091, a homolog of RSP1091 comprising a sequence at least about 90% identical to SEQ ID NO:4, or a homolog of RSP1091 comprising a sequence at least about 90% identical to SEQ ID NO:16. The RSP1090 or homolog thereof may comprise an ortholog of RSP1090, a homolog of RSP1090 comprising a sequence at least about 90% identical to SEQ ID NO:6, or a homolog of RSP1090 comprising a sequence at least about 90% identical to SEQ ID NO:17.

One aspect of the invention comprises a recombinant nucleic acid configured to express one or more enzymes selected from the group consisting of RSP2144 or homolog thereof, RSP1091 or homolog thereof, and RSP1090 or homolog thereof. The recombinant nucleic acid may comprise a promoter operably linked to a coding sequence for the enzyme. The promoter may be a promoter different from a promoter operably linked to the coding sequence in nature.

Another aspect of the invention comprises an isolated enzyme selected from the group consisting of RSP2144 or homolog thereof, RSP1091 or homolog thereof, and RSP1090 or homolog thereof.

Another aspect of the invention comprises a fusion protein comprising an enzyme fused to a protein tag. The enzyme may be selected from the group consisting of RSP2144 or homolog thereof, RSP1091 or homolog thereof, and RSP1090 or homolog thereof. The protein tag may be an affinity tag.

Another aspect of the invention is a recombinant microorganism modified to express or overexpress one or more enzymes selected from the group consisting of RSP2144 or homolog thereof, RSP1091 or homolog thereof, and RSP1090 or homolog thereof. In some versions, the microorganism comprises one or more recombinant nucleic acids configured to express one or more of the enzymes. The microorganism may be a bacterium, such as *Rhodobacter sphaeroides*, *Escherichia coli*, and *Rhodopseudomonas palustris*, among others. The microorganism preferably produces an increased amount of a fatty acid compared to a corresponding microorganism not comprising the one or more recombinant nucleic acids. The fatty acid may be selected from the group consisting of a branched-chain fatty acid, a cyclic fatty acid, and a furan-containing fatty acid. The branched-chain fatty acid may be a methylated fatty acid such as 11-methyl-octadecenoate. The cyclic fatty acid may be a cyclopropene fatty acid such as 11,12-methylene-octadec-11-enoate. The furan-containing fatty acid may comprise a fatty acid such as 10,13-epoxy-11-methyl-octadecadienoate. In some versions, the microorganism may further comprise a modification that eliminates from the microorganism a native protein selected from the group consisting of RSP1091 or homolog thereof and RSP1090 or homolog thereof.

Another aspect of the invention comprises an in vivo method of producing a fatty acid. The method comprises culturing a microorganism comprising a modification that increases expression of one or more enzymes with respect to a corresponding microorganism not comprising the modification, wherein the microorganism produces an increased amount of the fatty acid compared to a corresponding microorganism not comprising the modification, and isolating the fatty acid. The one or more enzymes are preferably selected from the group consisting of RSP2144 or homolog thereof, RSP1091 or homolog thereof, and RSP1090 or homolog thereof. The modification may comprise a mutation or other genetic modification. In some versions, the microorganism comprises one or more recombinant nucleic acids configured to express the one or more enzymes. In some versions, the microorganism comprises a modification that disrupts binding between ChrR and $\sigma^E$ or homologs thereof. In some versions, the microorganism comprises a modification that increases expression of $\sigma^E$ or a homolog thereof. In some versions, the microorganism comprises a modification that eliminates from the microorganism a native ChrR or homolog thereof. In some methods, the microorganism comprises a recombinant nucleic acid configured to express a protein having a mutated form of SEQ ID NO:14, wherein the mutated form of SEQ ID NO:14 comprises a mutation selected from the group consisting of K38E, K38R, and M42A. In some methods, the microorganism comprises a modification that eliminates from the microorganism a native protein having a sequence of SEQ ID NO:13 or sequence homologous thereto. In some methods, the microorganism comprises a recombinant nucleic acid configured to express a protein having a mutated form of SEQ ID NO:13, wherein the mutated form of SEQ ID NO:13 comprises a mutation selected from the group consisting of H6A, H31A, C35A, C35S, C38A, C38S, C38R and C187/189S. The microorganism is preferably a bacterium. The produced fatty acid is preferably selected from the group consisting of a branched-chain fatty acid, a cyclic fatty acid, and a furan-containing fatty acid.

Another aspect of the invention comprises an in vitro method of producing a fatty acid. The method comprises producing a second fatty acid from a first fatty acid by contacting the first fatty acid in vitro with one or more enzymes selected from the group consisting of RSP2144 or homolog thereof, RSP1091 or homolog thereof, and RSP1090 or homolog thereof. The first fatty acid may be selected from the group consisting of a straight-chain fatty acid, a branched-chain fatty acid, and a cyclic fatty acid. The second fatty acid may be selected from the group consisting of a branched-chain fatty acid, and a cyclic fatty acid, and a furan-containing fatty acid. One or both of the first fatty acid and the second fatty acid preferably comprises a contiguous chain of 18 carbons. Some versions comprise producing a branched-chain fatty acid from a straight-chain fatty acid by contacting the straight-chain fatty acid with RSP2144 or a homolog thereof. Some versions comprise producing a cyclic fatty acid from a branched-chain fatty acid by contacting the branched-chain fatty acid with RSP1091 or a homolog thereof. Some versions comprise producing a furan-containing fatty acid from a cyclic fatty acid by contacting the cyclic fatty acid with RSP1090 or a homolog thereof.

Another aspect of the invention comprises a method of scavenging a reactive oxygen species. The method comprises contacting the reactive oxygen species with an isolated furan-containing fatty acid. The furan-containing fatty acid is preferably 10,13-epoxy-11-methyl-octadecadienoate. The reactive oxygen species may comprise $^1O_2$.

The objects and advantages of the invention will appear more fully from the following detailed description of the preferred embodiment of the invention made in conjunction with the accompanying drawings.

spectra using acetonitrile (ACN) positive chemical ionization (PCI). The top panel in FIG. 3B shows a full-scan MS spectrum of the 19M-UFA indicated in FIG. 1B, indicating key ACN PCI adducts of the intact species. The bottom panel in FIG. 3B shows an MS/MS spectrum of the [M+MIE]$^+$ ion of the 19M-UFA indicated in FIG. 1B at 25 eV, showing key fragments that localize the double bond to position 12.

Figure 4A:
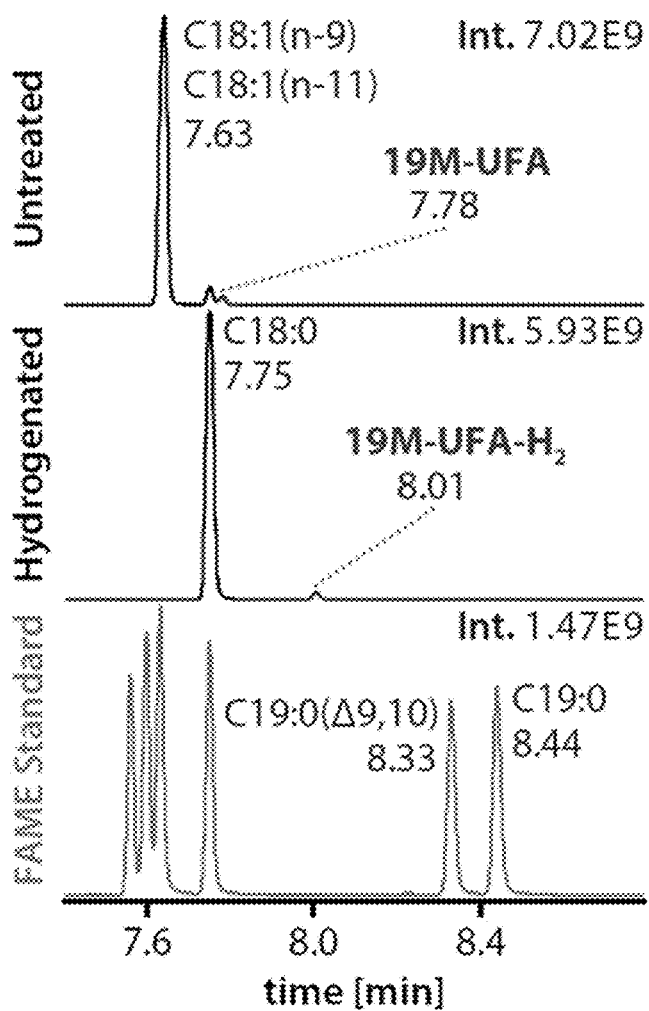
Figure 4B:
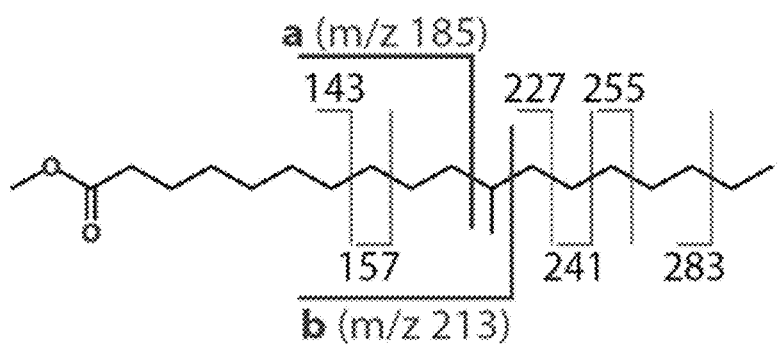
Figure 4C:
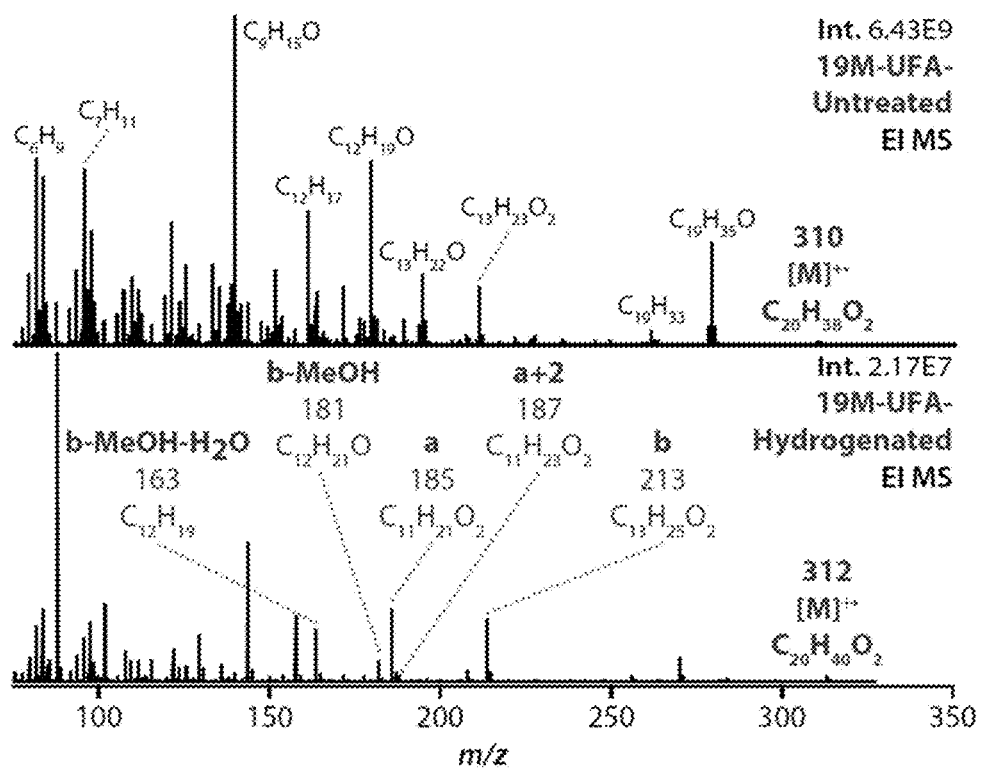
Figure 4D:
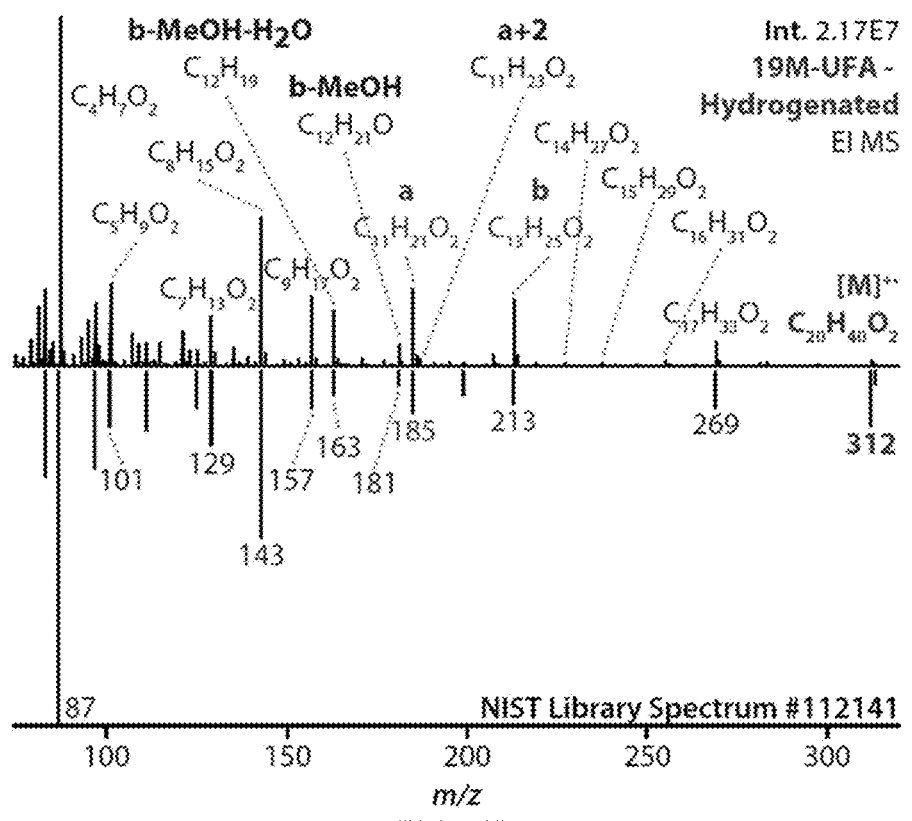

FIG. 4A shows show gas chromatograms of untreated 19M-UFA FAME derived from ΔChrR *R. sphaeroides* cells (top panel), hydrogenated 19M-UFA FAME derived from ΔChrR *R. sphaeroides* cells (middle panel), and a FAME standard (bottom panel). FIG. 4B shows fragmentation sites methyl 11-methyl-octadecanoate in electron ionization. FIG. 4C shows electron ionization spectra of untreated 19M-UFA FAME (top trace) and hydrogenated 19M-UFA (methyl 11-methyl-octadecanoate) (bottom trace). FIG. 4D shows the electron ionization spectrum of hydrogenated 19M-UFA FAME (top trace) and its comparison to the reference library spectrum for methyl 11-methyl-octadecanoate in electron ionization (bottom trace).

Figure 5:
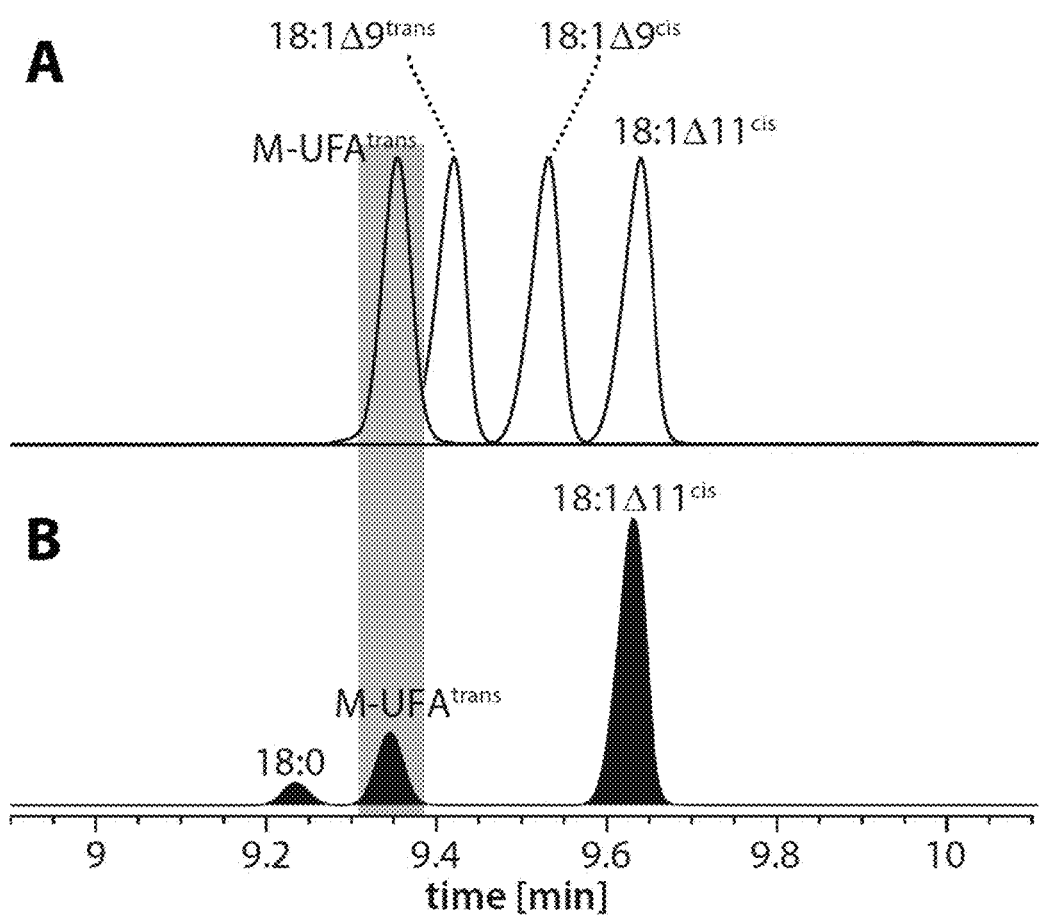
Figure 6A:
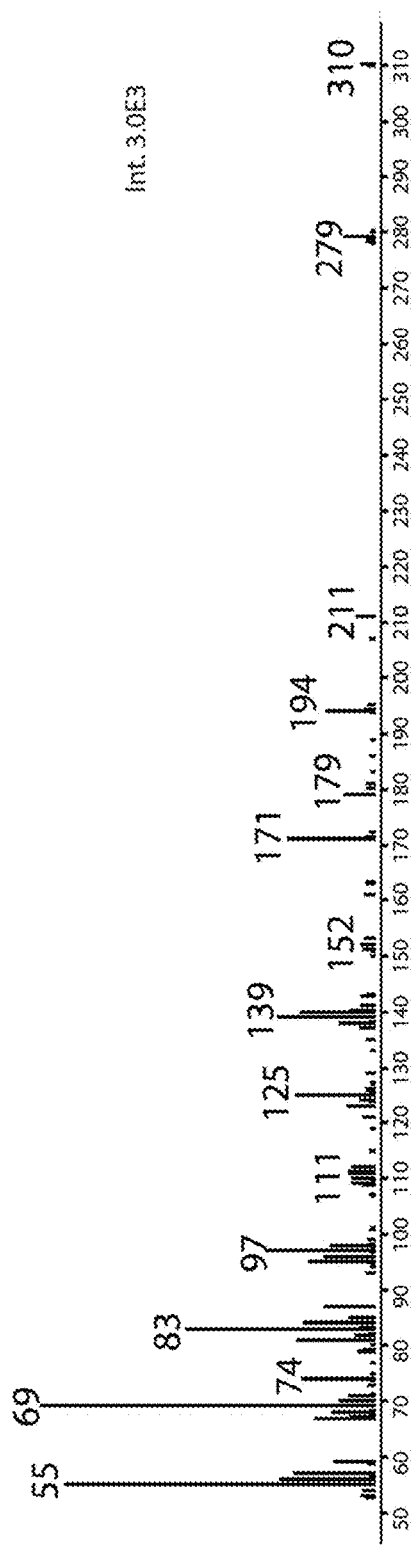
Figure 6B:
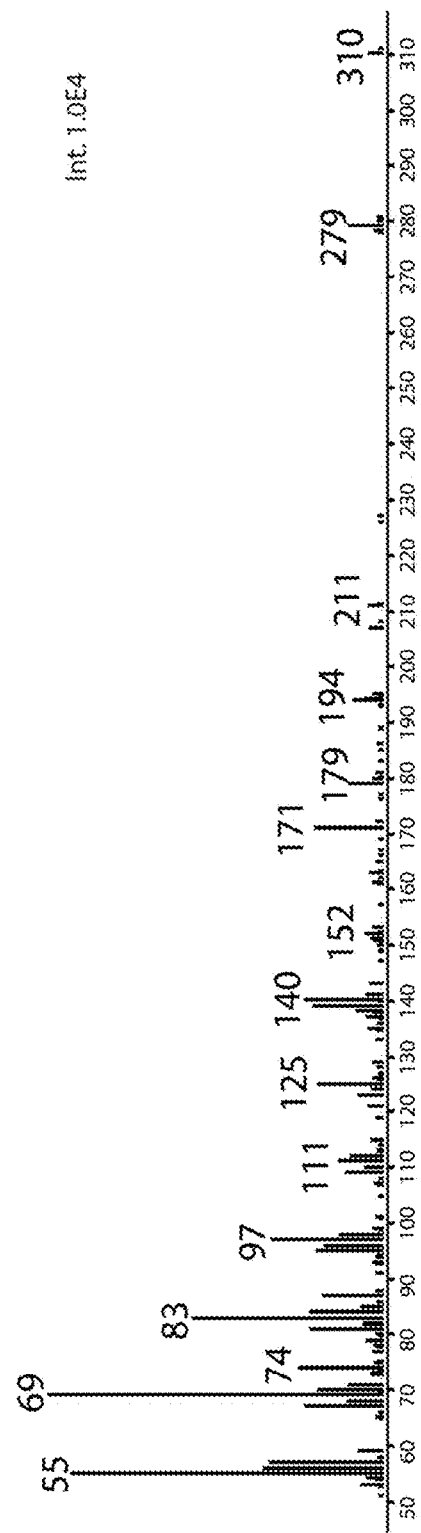

FIG. 5 shows the identification of fatty acyl isomers by gas chromatography flame ionization detection from ΔChrR cells. Panel A shows the elution profile of synthetic standards 19M-UFAtrans (9.34 min), C18:1Δ9trans (9.42 min), C18:1Δ9cis (9.53 min), and C18:1Δ9cis (9.63 min). Panel B shows the elution profile of FAMES isolated from ΔChrR cells with species eluting at 9.23 min, 9.34 min and 9.63 min.

FIGS. 6A-6D show electron ionization spectra of methyl esters prepared from (FIG. 6A) chemically synthetized 19M-UFA, (FIG. 6B) 19M-UFA from ΔChrR cells, (FIG. 6C) chemically synthesized 19Fu-FA, and (FIG. 6D) 19Fu-FA from ΔChrR cells.

Figure 7A:
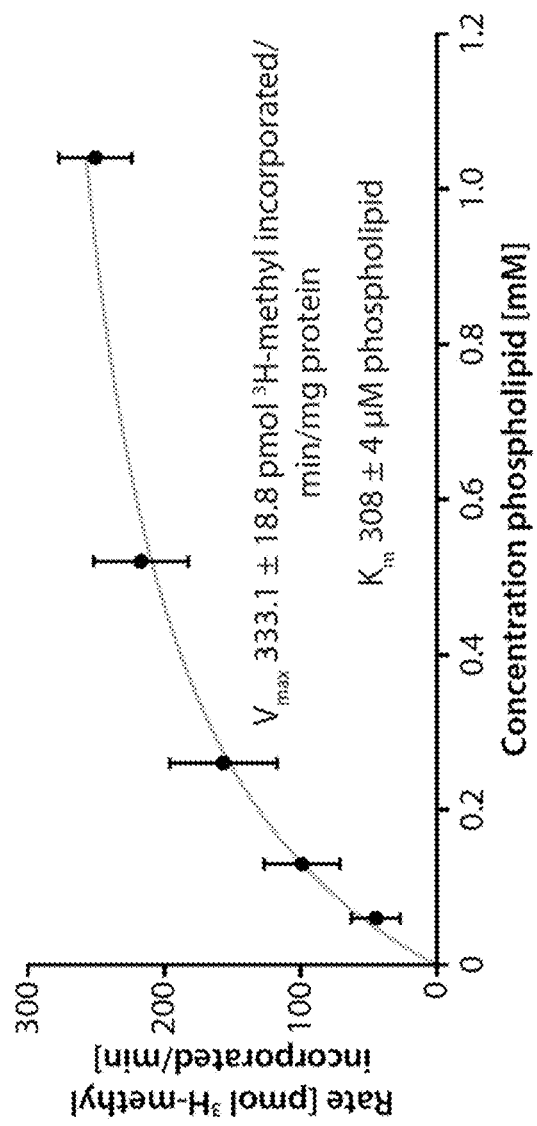
Figures 7B, 7C:
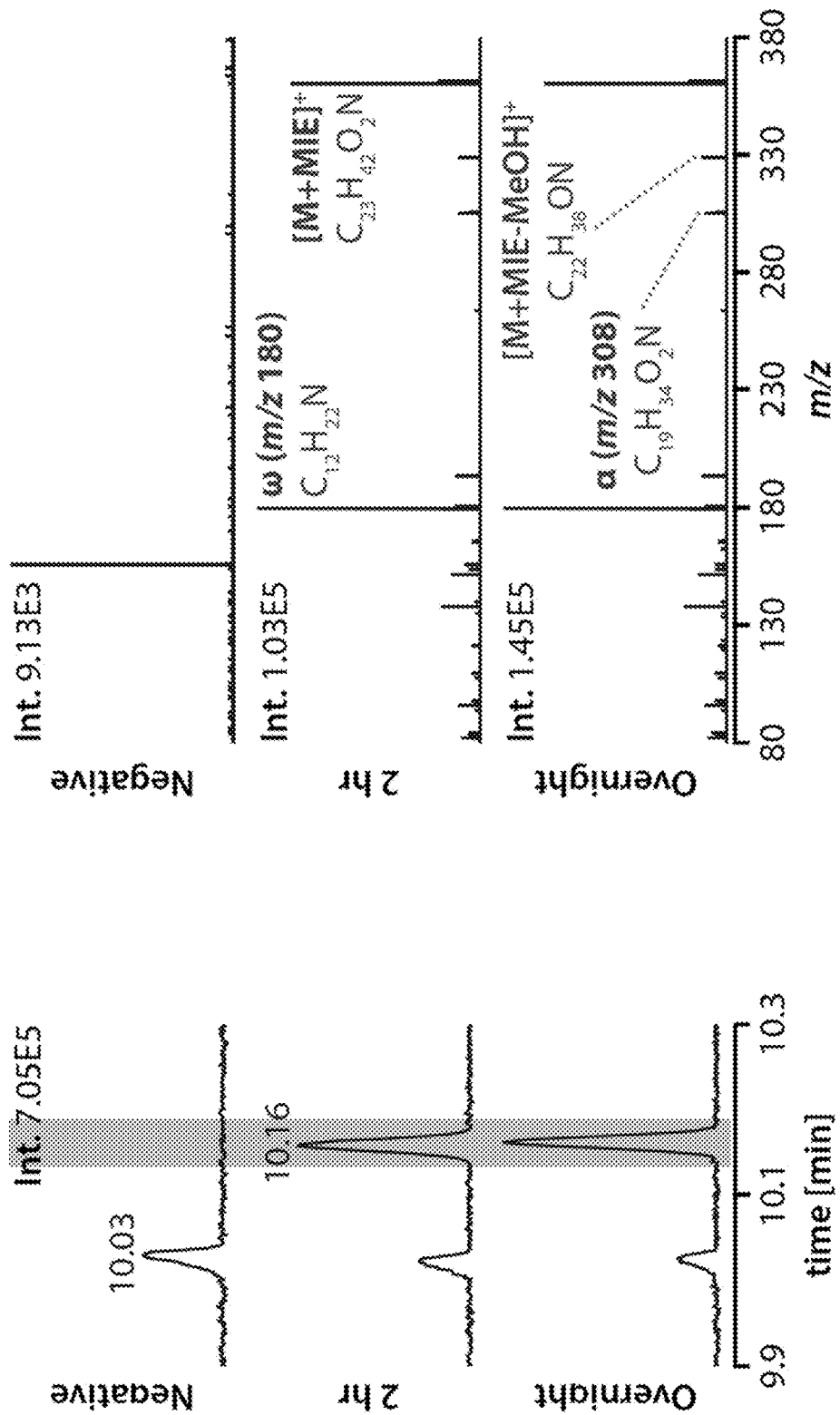

FIG. 7A shows the rate of incorporation of $^3$H-methyl labelled S-adenosyl methionine (SAM) into trichloroacetic acid (TCA)-insoluble material versus concentration of phospholipid upon treating micelles containing native *R. sphaeroides* phospholipids as a substrate with recombinant RSP2144 in the presence of $^3$H-methyl labelled SAM in vitro. FIG. 7B and FIG. 7C show gas chromatograms (FIG. 7B) and ionization spectra (FIG. 7C) of FAME products obtained using *R. sphaeroides* lipids in the absence (negative, top panels) or presence (2-hr (middle panels) and overnight (bottom panels) time points) of His$_6$-RSP2144 protein (UfaM) and SAM in vitro. The chromatographic response of lipids before and after 2 hr or overnight incubation with UfaM in vitro shows an increase in 19M-UFA concentration when incubated with UfaM (shaded in grey). The ionization spectra show the ACN PCI [M+MIE]$^+$ MS/MS (25 eV) spectra collected at the apex of the 19M-UFA peak in all three samples, with key fragment ions labeled. No 19M-UFA was detected in the reactions lacking UfaM (negative).

Figure 8A:
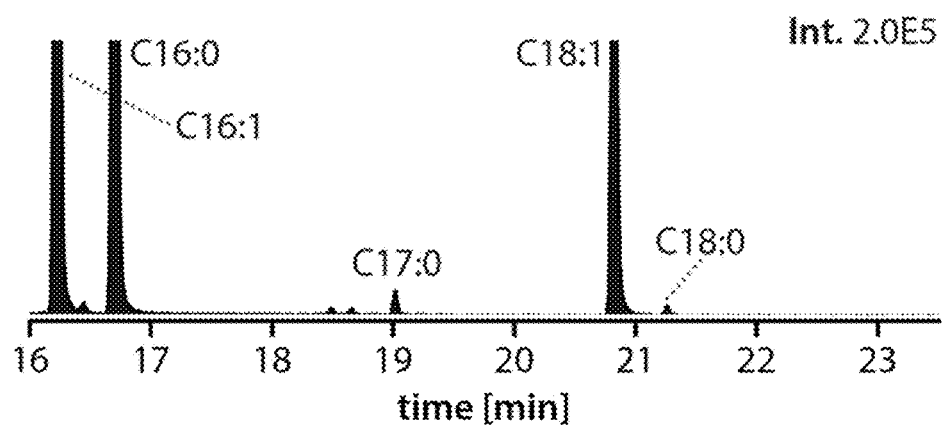
Figure 8B:
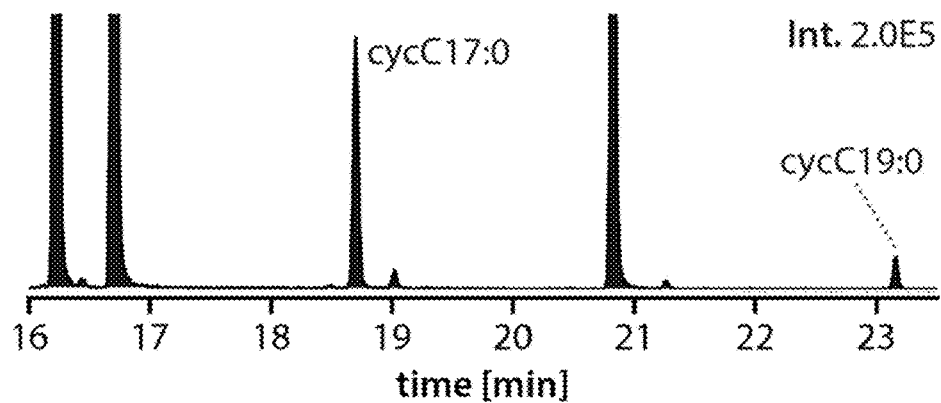
Figure 8C:
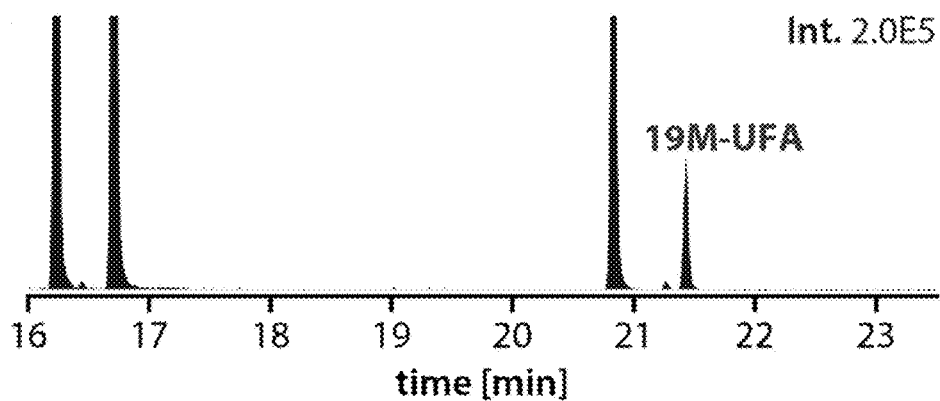

FIGS. 8A-8C show chromatograms of FAMEs derived from fatty acids accumulated in an *Escherichia coli* ΔCfa mutant (JW1653) (FIG. 8A), an *E. coli* ΔCfa mutant containing *E. coli* cfa on a plasmid (FIG. 8B), and an *E. coli* ΔCfa mutant containing RSP2144 on a plasmid (FIG. 8C). The Y- and X-axes show the relative abundance and retention time for each species, respectively.

Figure 9:
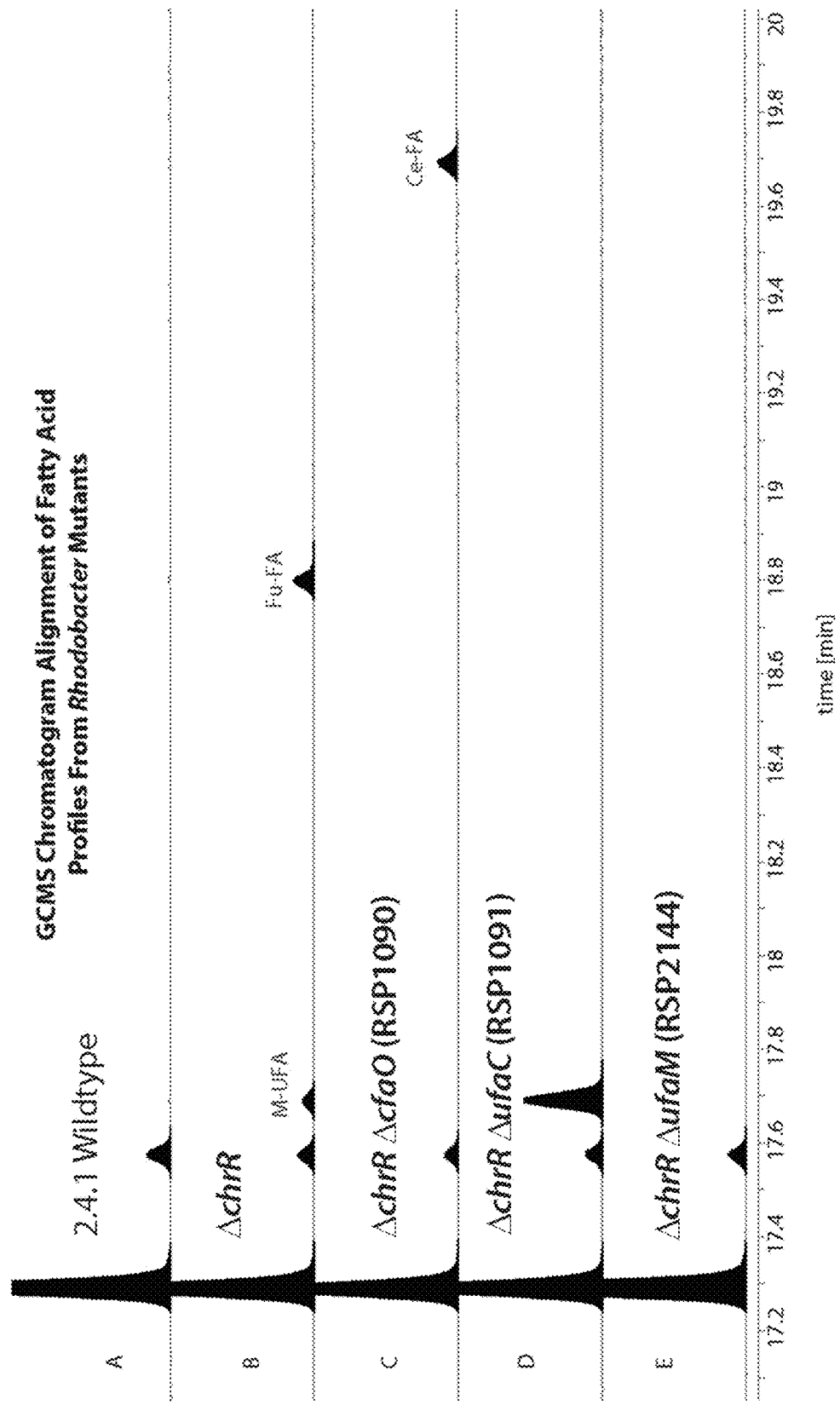

FIG. 9 shows gas chromatograms of FAMEs of fatty acids from various *R. sphaeroides* 2.4.1 cells and mutants, including wild type cells (A), ΔchrR cells (B), ΔchrR/ΔcfaO (RSP1090) cells (C), ΔchrR/ΔufaC (RSP1091) cells (D), and ΔChrR/ΔufaM (RSP2144) cells (E). The Y- and X-axes show the relative abundance and retention time for each species, respectively.

FIG. 10 shows a proposed pathway for the production of 19M-UFA from vaccenic acid via the gene products of ufaM (RSP2144), ufaC (RSP1091), and cfaO (RSP1090).

Figure 11:
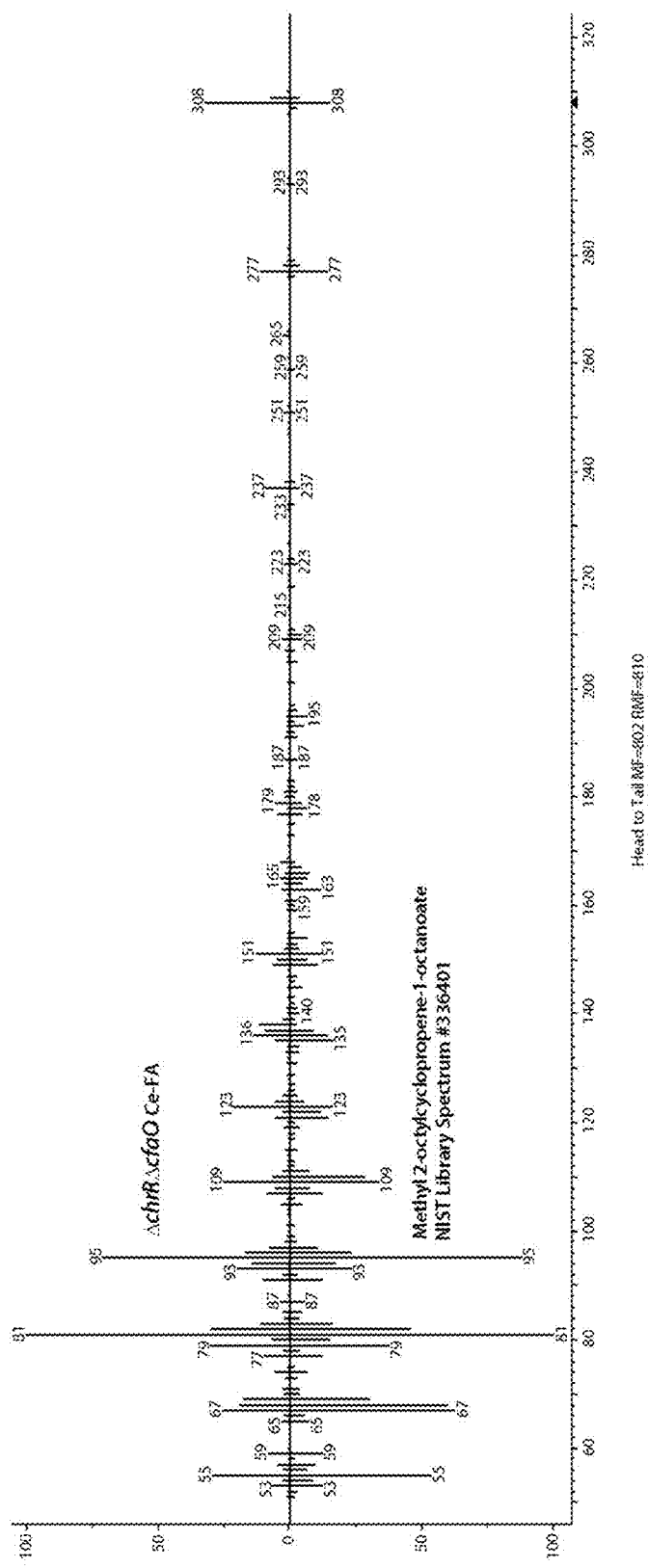

FIG. 11 shows a comparison of the mass spectrum of the Ce-FA product of the *R. sphaeroides* ΔChrR/ΔcfaO mutant (top spectrum) with Spectrum 336401 from the National Institutes of Standards and Technology (NIST) Library for methyl 2-octylcyclopropene-1-octanoate (methyl ester of 11,12-methylene-octadec-11-enoate) (Ce-FA) (bottom spectrum).

Figure 12:
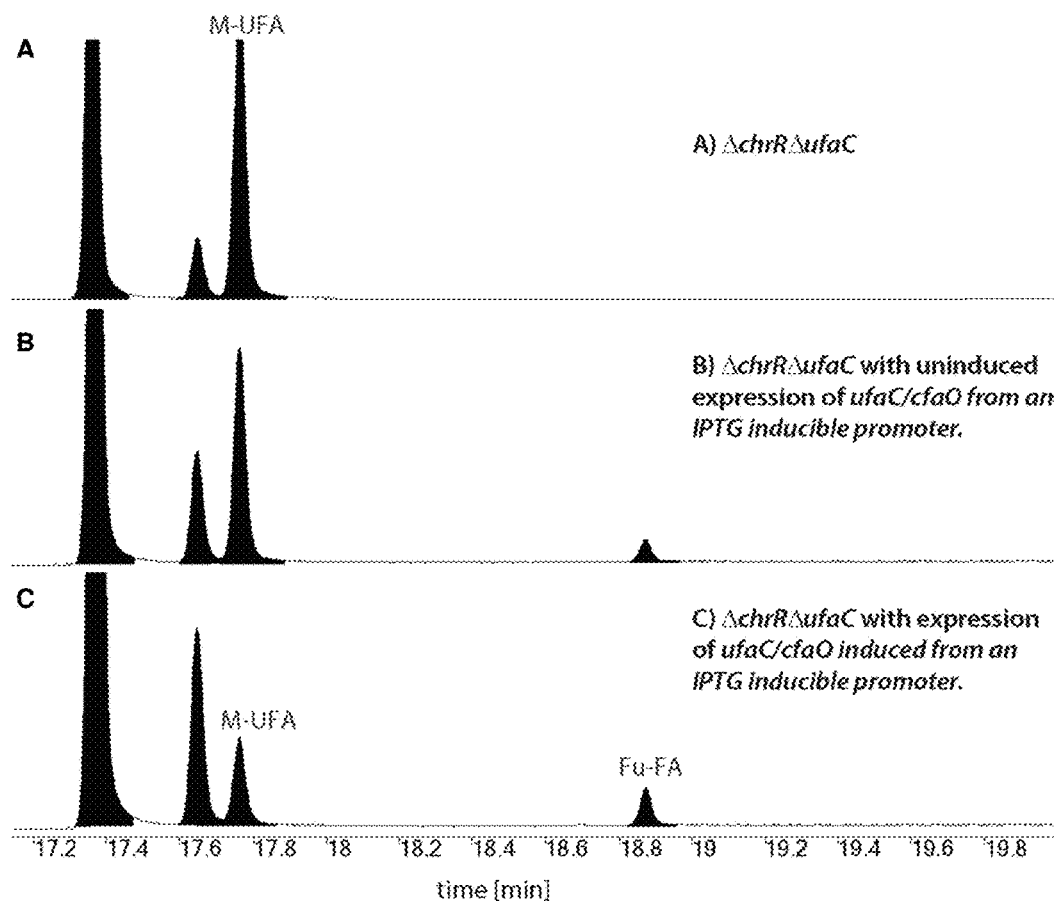

FIG. 12 shows gas chromatograms of FAMEs of fatty acids from various *R. sphaeroides* 2.4.1 cells and mutants, including ΔChrR/ΔufaC cells (A), ΔchrR/ΔufaC cells with uninduced expression of ufaC and cfaO from an IPTG-inducible promoter (B), and ΔchrR/ΔufaC cells with induced expression of ufaC and cfaO from an IPTG-inducible promoter (C). The Y- and X-axes show the relative abundance and retention time for each species, respectively.

Figure 13:
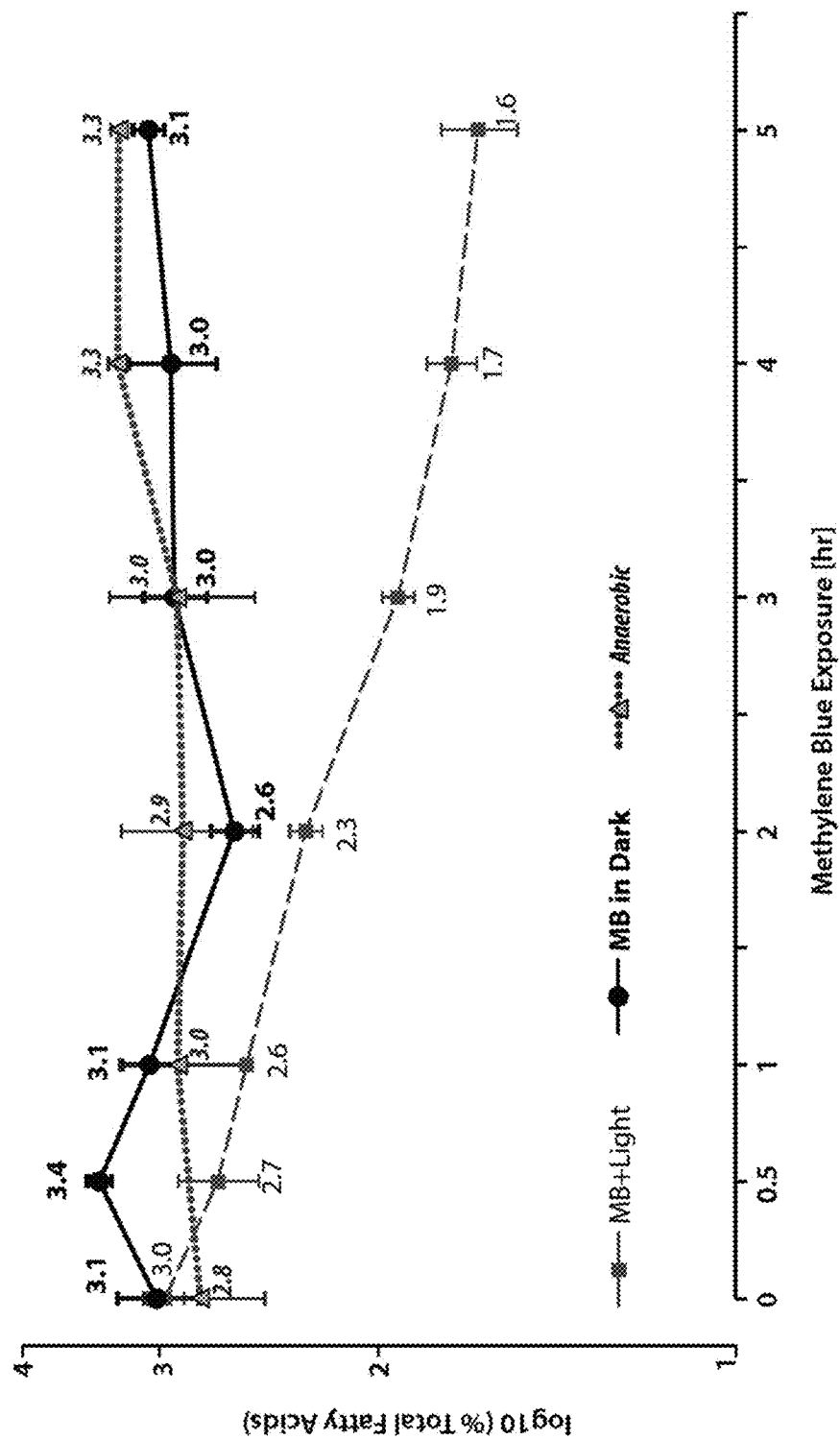

FIG. 13 shows time-dependent changes in the cellular abundance of 19Fu-FA in aerobically grown ΔChrR cells exposed to methylene blue (MB) in the light (MB+Light, squares), aerobically grown ΔChrR cells exposed to MB in the dark (MB in dark, circles), or ΔChrR cells that were returned to anaerobic growth (anaerobic, triangles).

Figure 14A:
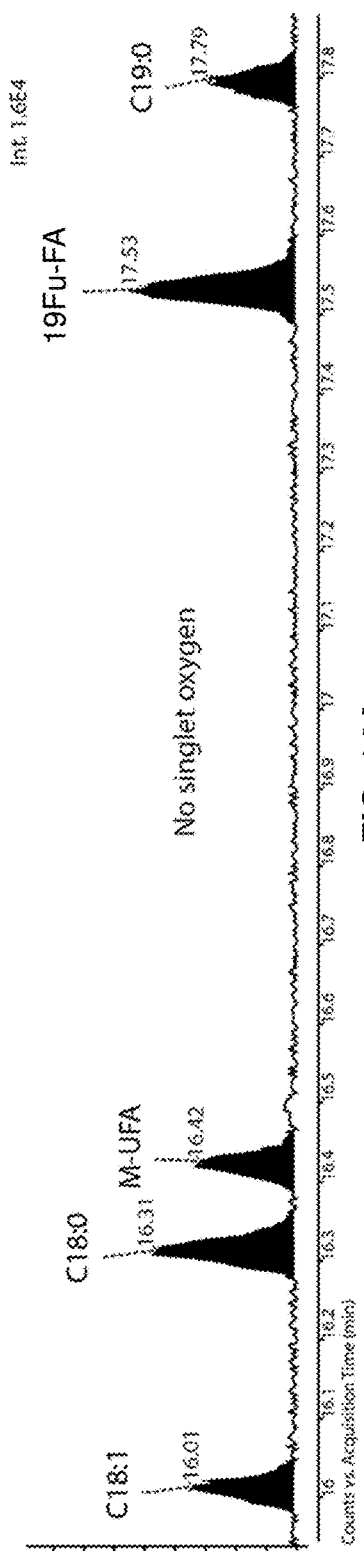
Figure 14B:
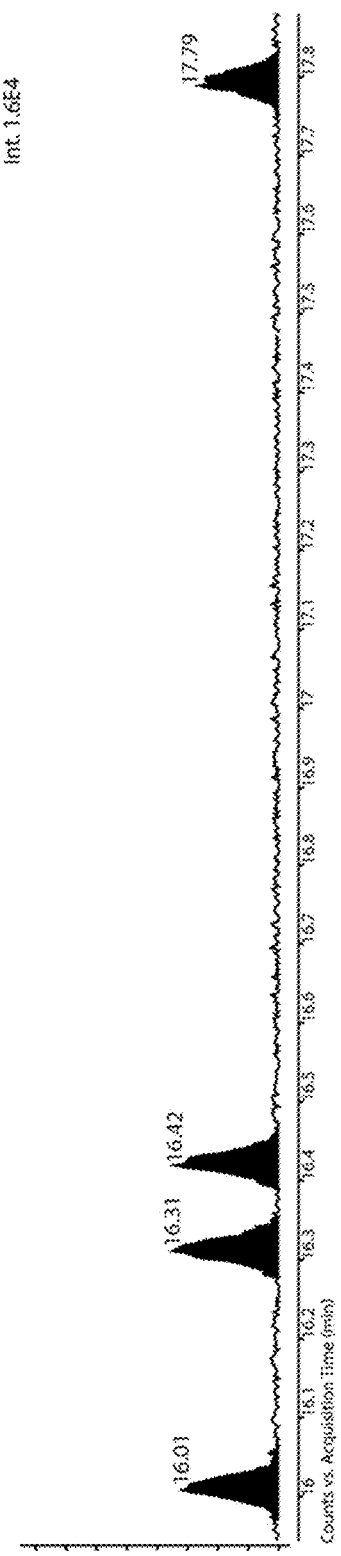

FIGS. 14A and 14B show gas chromatograms in counts versus acquisition time (min.) of fatty acids either exposed to $^1O_2$ (MB in light) (FIG. 14B) or not exposed to $^1O_2$ (MB in dark) (FIG. 14A) in a test tube in vitro.

Figure 15:
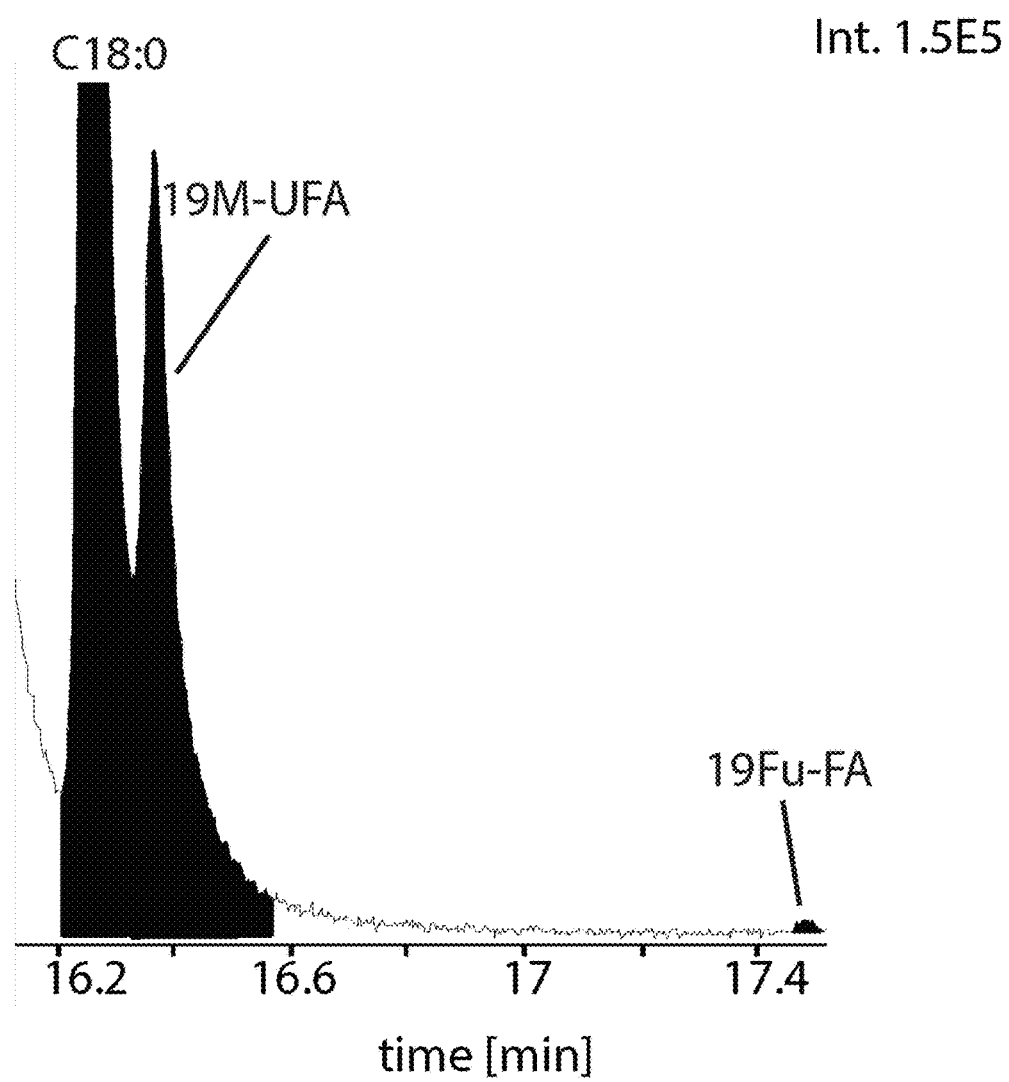

FIG. 15 shows gas chromatograms in counts versus acquisition time (min.) of fatty acids isolated from *Rhodopseudomonas palustris*.

Figure 16:
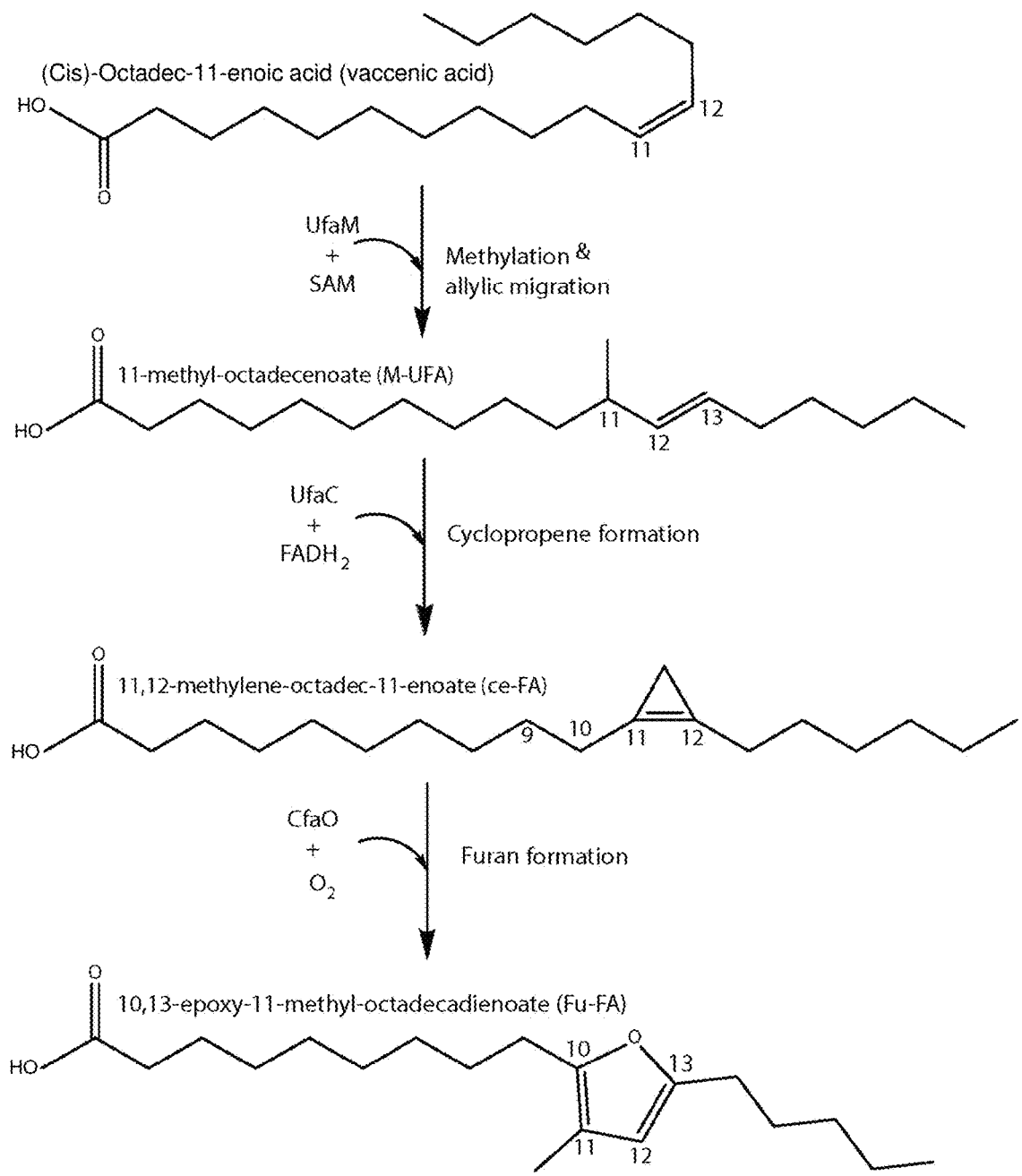

FIG. 16 shows a model pathway for synthesis of 19M-UFA and 19Fu-FA. UfaM (RSP2144) is a SAM-dependent methylase that participates in the production of 19M-UFA from vaccenic acid. UfaC (RSP1091) participates in the conversion of 19M-UFA to Ce-FA. CfaO (RSP1090) participates in the conversion of Ce-FA to 19Fu-FA.

Figure 17A:
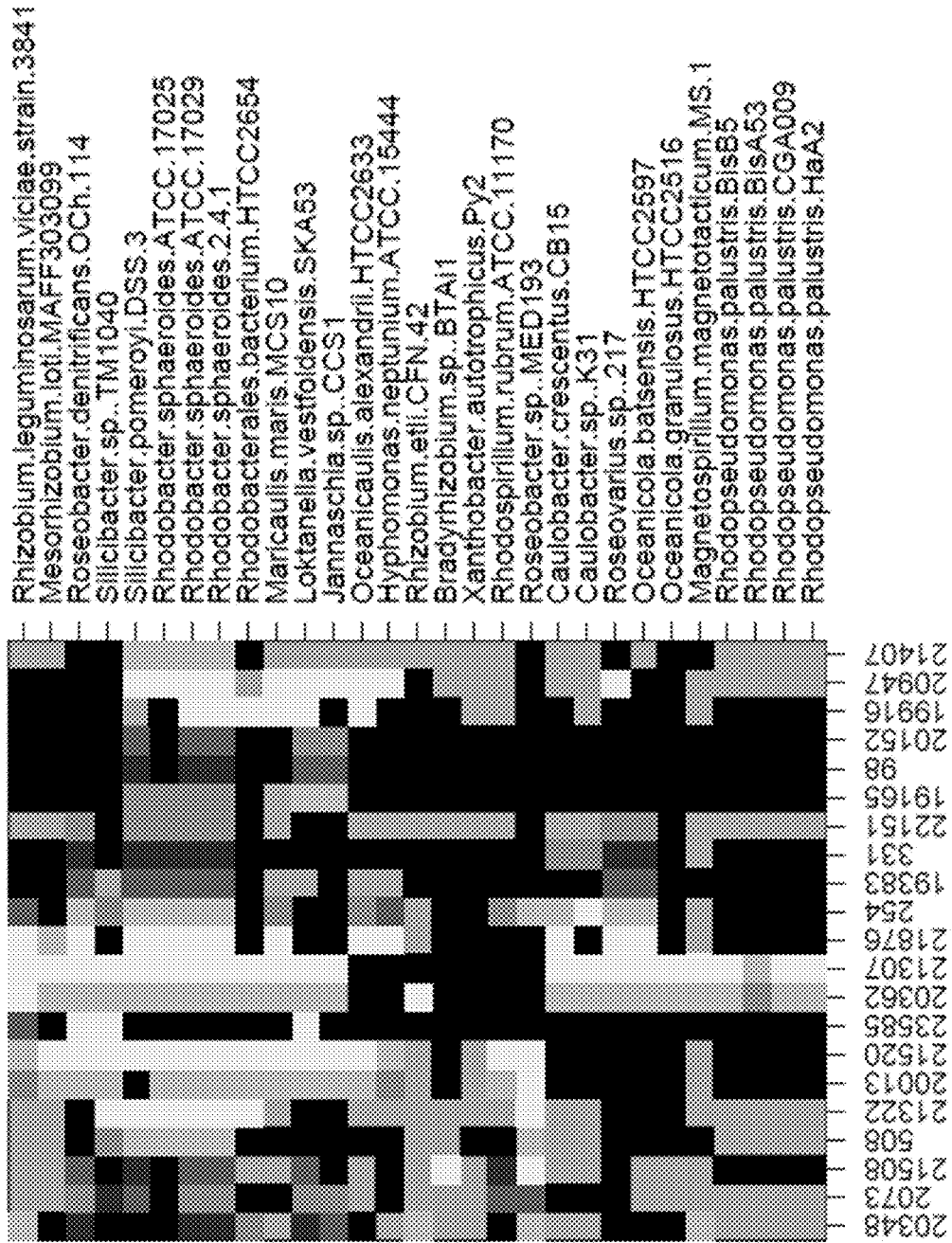
Figure 17B:

FIGS. 17A and 17B show $\sigma^E$ target genes across selected bacteria. Various bacteria are listed on the Y axis. Protein ortholog ID numbers are listed on the X axis. See Dufour et al. 2008.

DETAILED DESCRIPTION OF THE INVENTION

The enzymes of the invention comprise the enzymes encoded by RSP2144, RSP1091, RSP1090, RSP1089, RSP1088, and RSP1087 from *Rhodobacter sphaeroides* and homologs thereof. The designations "RSP2144," "RSP1091," "RSP1090," "RSP1089," "RSP1088," "RSP1087," and "homologs" may be used herein to refer to genes, enzymes encoded by the genes, or both the genes and enzymes encoded by the genes.

The RSP2144 of *R. sphaeroides* has an amino acid sequence of SEQ ID NO:2 and a coding sequence of SEQ ID NO:1. The RSP2144 enzyme is also referred to herein as "UfaM," and the RSP2144 coding sequence is also referred to herein as "ufaM." The RSP2144 enzyme is a fatty acyl methylase that is upregulated by $\sigma^E$ in the presence of $^1O_2$. The RSP2144 enzyme is capable of producing branched-chain fatty acids such as 11-methyl-octadecenoate from straight-chain fatty acids such as vaccenic acid.

Homologs of RSP2144 include enzymes having a sequence at least about 60%, 65%, 70%, 75%, 80%, 85%, 90%, 95%, 97%, 99%, or more identical to SEQ ID NO:2. Homologs of RSP2144 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:2. Homologs of RSP2144 also include enzymes that are upregulated by orthologs of R. sphaeroides $\sigma^E$ and have a sequence at least about 60%, 65%, 70%, 75%, 80%, 85%, 90%, 95%, 97%, 99%, or more identical to SEQ ID NO:2. Homologs of RSP2144 also include orthologs of RSP2144 and modified forms thereof. See Ziegelhoffer et al. and Dufour et al. for orthologs of RSP2144 and R. sphaeroides $\sigma^E$. It is understood that the homologs of RSP2144 have RSP2144 activity.

An exemplary homolog of RSP2144 is an enzyme comprising a sequence at least about 80%, 85%, 90%, 95%, 97%, 99%, or more identical to SEQ ID NO:15. SEQ ID NO:15 represents an ortholog of RSP2144 in R. palustris. Other exemplary homologs of RSP2144 include the enzyme of Jannaschia sp. CCS1 entered in GenBank under Accession Number WP_011455112.1, the enzyme of Dinoroseobacter shibae entered in GenBank under Accession Number WP_012178984.1, the enzyme of Loktanella vestfoldensis entered in GenBank under Accession Number WP_007204671.1, the enzyme of Oceanicola sp. HL-35 entered in GenBank under Accession Number WP_024812002.1, the enzyme of Sagittula stellate entered in GenBank under Accession Number WP_005861028.1, the enzyme of Wenxinia marina entered in GenBank under Accession Number WP_018303672.1, the enzyme of Pseudorhodobacter ferrugineus entered in GenBank under Accession Number WP_022704200.1, and the enzyme of Rhodopseudomonas palustris sp. CGA009 entered in GenBank under Accession Number WP 011158119.1.

The RSP1091 of R. sphaeroides has an amino acid sequence of SEQ ID NO:4 and a coding sequence of SEQ ID NO:3. The RSP1091 enzyme is also referred to herein as "UfaC," and the RSP1091 coding sequence is also referred to herein as "ufaC." RSP1091 is upregulated by $\sigma^E$ in the presence of $^1O_2$. The RSP1091 enzyme is capable of producing cyclic fatty acids such as 11,12-methylene-octadec-11-enoate from branched-chain fatty acids such as 11-methyl-octadecenoate.

Homologs of RSP1091 include enzymes having a sequence at least about 60%, 65%, 70%, 75%, 80%, 85%, 90%, 95%, 97%, 99%, or more identical to SEQ ID NO:4. Homologs of RSP1091 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:4. Homologs of RSP1091 also include enzymes that are upregulated by homologs of R. sphaeroides $\sigma^E$ and have a sequence at least about 60%, 65%, 70%, 75%, 80%, 85%, 90%, 95%, 97%, 99%, or more identical to SEQ ID NO:4. Homologs of RSP1091 also include orthologs of RSP1091 and modified forms thereof. See Ziegelhoffer et al. and Dufour et al. for orthologs of RSP1091 and R. sphaeroides $\sigma^E$. It is understood that the homologs of RSP1091 have RSP1091 activity.

An exemplary homolog of RSP1091 is an enzyme comprising a sequence at least about 80%, 85%, 90%, 95%, 97%, 99%, or more identical to SEQ ID NO:16. SEQ ID NO:16 represents an ortholog of RSP1091 in R. palustris. Other exemplary homologs of RSP1091 include the enzyme of Rhodobacter sp. SW2 entered in GenBank under Accession Number WP_008027729.1, the enzyme of Pseudorhodobacter ferrugineus entered in GenBank under Accession Number WP_022702381.1, the enzyme of Salipiger mucosus entered in GenBank under Accession Number WP_021120150.1, the enzyme of Rhodobacter sp. CACIA14H1 entered in GenBank under Accession Number WP_023664950.1, the enzyme of Oceanicola sp. HL-35 entered in GenBank under Accession Number WP_024811361.1, the enzyme of Roseobacter sp. AzwK-3b entered in GenBank under Accession Number WP_007812241.1, the enzyme of Roseibacterium elongatum entered in GenBank under Accession Number WP_025311080.1, the enzyme of Oceanicola batsensis entered in GenBank under Accession Number WP_009806953.1, the enzyme of Dinoroseobacter shibae entered in GenBank under Accession Number WP_012177046.1, and the enzyme of R. palustris sp. CGA009 entered in GenBank under Accession Number NP_947913.1.

The RSP1090 from R. sphaeroides has an amino acid sequence of SEQ ID NO:6 and a coding sequence of SEQ ID NO:5. The RSP1090 enzyme is also referred to herein as "CfaO," and the RSP1090 coding sequence is also referred to herein as "cfaO." RSP1090 is upregulated by $\sigma^E$ in the presence of $^1O_2$. The RSP1090 enzyme is capable of producing furan-containing fatty acids such as 10,13-epoxy-11-methyl-octadecadienoate from cyclic fatty acids such as 11,12-methylene-octadec-11-enoate.

Homologs of RSP1090 include enzymes having a sequence at least about 60%, 65%, 70%, 75%, 80%, 85%, 90%, 95%, 97%, 99%, or more identical to SEQ ID NO:6. Homologs of RSP1090 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:6. Homologs of RSP1090 also include enzymes that are upregulated by homologs of R. sphaeroides $\sigma^E$ and have a sequence at least about 60%, 65%, 70%, 75%, 80%, 85%, 90%, 95%, 97%, 99%, or more identical to SEQ ID NO:6. Homologs of RSP1090 also include orthologs of RSP1090 and modified forms thereof. See Ziegelhoffer et al. and Dufour et al. for orthologs of RSP1090 and R. sphaeroides $\sigma^E$. It is understood that the homologs of RSP1090 have RSP1090 activity.

An exemplary homolog of RSP1090 is an enzyme comprising a sequence at least about 80%, 85%, 90%, 95%, 97%, 99%, or more identical to SEQ ID NO:17. SEQ ID NO:17 represents an ortholog of RSP1090 in R. palustris. Other exemplary homologs of RSP1090 include the enzyme of Rhodobacter sp. CACIA14H1 entered in GenBank under Accession Number WP_023664949.1, the enzyme of Rhodobacter sp. SW2 entered in GenBank under Accession Number WP_008027731.1, the enzyme of Pseudorhodobacter ferrugineus entered in GenBank under Accession Number WP_022702382.1, the enzyme of Dinoroseobacter shibae entered in GenBank under Accession Number WP_012177047.1, and the enzyme of R. palustris sp. CGA009 entered in GenBank under Accession Number NP_947912.1.

The RSP1089 of R. sphaeroides has an amino acid sequence of SEQ ID NO:8 and a coding sequence of SEQ ID NO:7. RSP1089 is upregulated by $\sigma^E$ in the presence of $^1O_2$.

Homologs of RSP1089 include enzymes having a sequence at least about 60%, 65%, 70%, 75%, 80%, 85%, 90%, 95%, 97%, 99%, or more identical to SEQ ID NO:8. Homologs of RSP1089 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:8. Homologs of RSP1089 also include sequences of enzymes that are upregulated by homologs of R. sphaeroides $\sigma^E$ and have a sequence at least about 60%, 65%, 70%, 75%, 80%, 85%, 90%, 95%, 97%, 99%, or more identical to SEQ ID NO:8. Homologs of RSP1089 also include orthologs of RSP1089 and modified forms thereof. See Ziegelhoffer et al. and Dufour et al. for orthologs of RSP1089 and *R. sphaeroides* $\sigma^E$. It is understood that the homologs of RSP1089 have RSP1089 activity.

Exemplary homologs of RSP1089 include the enzyme of *R. sphaeroides* entered in GenBank under Accession Number WP_011909884.1, the enzyme of *Rhodobacter* sp. SW2 entered in GenBank under Accession Number WP_008027733.1, the enzyme of *Roseobacter litoralis* entered in GenBank under Accession Number WP_013963634.1, and the enzyme of *Oceanicola* sp. HL-35 entered in GenBank under Accession Number WP_024811359.1.

The RSP1088 of *R. sphaeroides* has an amino acid sequence of SEQ ID NO:10 and a coding sequence of SEQ ID NO:9. RSP1088 is upregulated by $\sigma^E$ in the presence of $^1O_2$.

Homologs of RSP1088 include enzymes having a sequence at least about 60%, 65%, 70%, 75%, 80%, 85%, 90%, 95%, 97%, 99%, or more identical to SEQ ID NO:10. Homologs of RSP1088 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:10. Homologs of RSP1088 also include enzymes that are upregulated by homologs of *R. sphaeroides* $\sigma^E$ and have a sequence at least about 60%, 65%, 70%, 75%, 80%, 85%, 90%, 95%, 97%, 99%, or more identical to SEQ ID NO:10. Homologs of RSP1088 also include orthologs of RSP1088 and modified forms thereof. See Ziegelhoffer et al. and Dufour et al. for orthologs of RSP1088 and *R. sphaeroides* $\sigma^E$. It is understood that the homologs of RSP1088 have RSP1088 activity.

Exemplary homologs of RSP1088 include the enzyme of *Rhodobacter* sp. AKP1 entered in GenBank under Accession Number WP_009563139.1, the enzyme of *R. sphaeroides* entered in GenBank under Accession Number WP_011909885.1, the enzyme of *Rhodobacter* sp. CACIA14H1 entered in GenBank under Accession Number WP_023664947.1, the enzyme of *Roseobacter* sp. AzwK-3b entered in GenBank under Accession Number WP_007812248.1, and the enzyme of *Dinoroseobacter shibae* entered in GenBank under Accession Number WP 012177049.1.

The RSP1087 of *R. sphaeroides* has an amino acid sequence of SEQ ID NO:12 and a coding sequence of SEQ ID NO:11. RSP1087 is upregulated by $\sigma^E$ in the presence of $^1O_2$.

Homologs of RSP1087 include enzymes having a sequence at least about 60%, 65%, 70%, 75%, 80%, 85%, 90%, 95%, 97%, 99%, or more identical to SEQ ID NO:12. Homologs of RSP1087 also include enzymes that are that are upregulated in the presence of $^1O_2$ and have a sequence at least about 60%, 65%, 70%, 75%, 80%, 85%, 90%, 95%, 97%, 99%, or more identical to SEQ ID NO:12. Homologs of RSP1087 also include enzymes that are upregulated by homologs of *R. sphaeroides* $\sigma^E$ and have a sequence at least about 60%, 65%, 70%, 75%, 80%, 85%, 90%, 95%, 97%, 99%, or more identical to SEQ ID NO:12. Homologs of RSP1087 also include orthologs of RSP1087 and modified forms thereof. See Ziegelhoffer et al. and Dufour et al. for orthologs of RSP1087 and *R. sphaeroides* $\sigma^E$. It is understood that the homologs of RSP1087 have RSP1087 activity.

An exemplary homolog of RSP1087 is an enzyme comprising a sequence at least about 80%, 85%, 90%, 95%, 97%, 99%, or more identical to SEQ ID NO:18. SEQ ID NO:18 represents a homolog of RSP1087 in *R. palustris*. Other exemplary homologs of RSP1087 include the enzyme of *Rhodobacter* sp. AKP1 entered in GenBank under Accession Number WP_009563138.1, the enzyme of *R. sphaeroides* entered in GenBank under Accession Number WP_011909886.1, the enzyme of *Rhodobacter* sp. CACIA14H1 entered in GenBank under Accession Number WP_023664946.1, the enzyme of *Sulfitobacter* sp. NB-68 entered in GenBank under Accession Number WP_025050106.1, and the enzyme of *R. palustris* sp. CGA009 entered in GenBank under Accession Number NP_948969.1.

The recombinant nucleic acids of the invention comprise recombinant nucleic acids configured to express one or more enzymes selected from the group consisting of RSP2144, RSP1091, RSP1090, RSP1089, RSP1088, RSP1087, and homologs thereof. The recombinant nucleic acids preferably comprise at least one genetic element that is not present in the RSP2144, RSP1091, RSP1090, RSP1089, RSP1088, or RSP1087 genes or homologs thereof in their natural state. Exemplary genetic elements, include promoters, enhancers, ribosome binding sites, etc. In an exemplary version, the recombinant nucleic acid comprises a promoter operably linked to a coding sequence for the enzyme, wherein the promoter is different from that operably linked to the coding sequence in its natural state. In another exemplary version, the recombinant nucleic acid comprises a sequence encoding a protein tag in frame with the enzyme coding sequence.

The isolated enzymes of the invention comprise any one or more of the enzymes described herein isolated from the organisms in which they are naturally expressed.

The fusion proteins of the invention comprise an enzyme of the invention fused to a protein tag. The protein tag may comprise an amino acid sequence of from about 1 to about 200 or more amino acids that are not naturally part of the enzyme. The protein tag may be fused to the N-terminus of the enzyme or the C-terminus of the enzyme, or a separate protein tag may be fused to each of the N-terminus and the C-terminus of the enzyme.

In some versions, the protein tag comprises an affinity tag. The affinity tags can be used for purification, detection with antibodies, or other uses. A number of affinity tags are known in the art. Exemplary affinity tags include the His tag, the Strep II tag, the T7 tag, the FLAG tag, the S tag, the HA tag, the c-Myc tag, the dihydrofolate reductase (DHFR) tag, the chitin binding domain tag, the calmodulin binding domain tag, and the cellulose binding domain tag. The sequences of each of these tags are well-known in the art. Preferred affinity tags are those smaller than about 20 amino acids, such as the His tag, the Strep II tag, the T7 tag, the FLAG tag, the S tag, the HA tag, the c-Myc tag.

The microorganisms of the present invention may comprise any type of microorganism. The microorganism may be prokaryotic or eukaryotic. Suitable prokaryotes include bacteria and archaea. Suitable types of bacteria include α- and γ-proteobacteria, gram-positive bacteria, gram-negative bacteria, ungrouped bacteria, phototrophs, lithotrophs, and organotrophs. Suitable eukaryotes include yeast and other fungi.

In some versions, the microorganisms of the invention comprise a microorganism that makes a C18 fatty acid. In some versions, the microorganisms of the invention comprise a microorganism that makes a C18 unsaturated fatty acid. In some versions, the microorganisms of the invention comprise a microorganism that makes a C18 unsaturated fatty acid comprising a double bond between carbons 11 and 12 in the hydrocarbon chain. In some versions, the microorganisms of the invention comprise a microorganism that makes a C18 fatty acid such as vaccenic acid. Such fatty acids serve as substrates for the enzymes described herein.

The microorganisms of the invention are configured to increase production of particular fatty acids compared to corresponding microorganisms. As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention. "Increasing production" or grammatical variants thereof refers to producing a fatty acid not made by the corresponding microorganism or producing more of a fatty acid already made by the corresponding microorganism.

The microorganism of the invention may be configured to produce at least about 1.5-fold, 5-fold, 10-fold, 50-fold, 100-fold, 250-fold, or 500-fold more of a particular fatty acid than a corresponding microorganism.

Examples of fatty acids of which the microorganisms of the invention are modified to increase production include branched-chain fatty acids, cyclic fatty acids, and furan-containing fatty acids. "Fatty acid" generally refers to compounds comprising a hydrocarbon chain and a carboxyl or carboxylate moiety and encompasses such forms as free acid forms, salt forms, esterified forms (e.g., phospholipid, sterol ester, glyceride), or other forms. "Straight-chain fatty acid" refers to a fatty acid comprising a non-branched, non-cyclic, non-substituted alkyl or alkenyl group (in cis or trans) as a hydrocarbon chain. "Branched-chain fatty acid" refers to a fatty acid that comprises a pendent carbon chain stemming from the hydrocarbon chain. "Cyclic fatty acid" refers to a fatty acid comprising a ring within or at the terminus of the hydrocarbon chain. "Furan-containing fatty acid" refers to a fatty acid that contains a furan group within or at the terminus of the hydrocarbon chain.

Exemplary branched-chain fatty acids produced by the microorganisms of the invention include methylated fatty acids. Branched-chain fatty acids comprising branches other than methyl groups may also be produced. An exemplary methylated fatty acid produced by the microorganisms of the invention includes 11-methyl-octadecenoate (19M-UFA). The 11-methyl-octadecenoate may be trans across the double bond. Exemplary cyclic fatty acids produced by the microorganisms of the invention include cyclopropene fatty acids. An exemplary cyclopropene fatty acid produced by the microorganisms of the invention includes 11,12-methylene-octadec-11-enoate (Ce-FA). An exemplary furan-containing fatty acid produced by the microorganisms of the invention includes 10,13-epoxy-11-methyl-octadecadienoate (19Fu-FA). The fatty acids produced by the microorganisms of the invention include from about 6 to about 30 carbons, such as from about 16 to about 26 carbons or from about 16 to about 22 carbons, and may be saturated or unsaturated. The fatty acids produced by the microorganisms of the invention may be in a free fatty acid form, a salt form, an esterified form (e.g., phospholipid, sterol ester, glyceride), or other form.

The microorganisms of the invention are modified to increase expression of one or more enzymes of the invention described herein. "Increasing expression" or grammatical variants thereof may refer to expressing an enzyme not made by the corresponding microorganism or expressing more of an enzyme already made by the corresponding microorganism.

Modifying the microorganism to increase expression of such enzymes can be performed using any methods currently known in the art or discovered in the future. Examples include genetically modifying the microorganism and culturing the microorganism in the presence of factors that increase expression of the enzyme. Suitable methods for genetic modification include but are not limited to placing the enzyme coding sequence under the control of a more active promoter, increasing the copy number of the enzyme gene, introducing a translational enhancer on the enzyme gene (see, e.g., Olins et al. 1989), and/or modifying factors that control expression of the enzyme gene. Increasing the copy number of the enzyme gene can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is introduced to a microorganism by genetic modification. "Heterologous" used in reference to a genetic element means that the genetic element is derived from a different species. A promoter or other genetic element that controls or affects expression of a particular coding sequence is herein described as being "operationally connected" to the coding sequence.

The microorganisms of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides using genetic engineering techniques. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress an enzyme produces the enzyme at a greater amount than a microorganism that does not include the recombinant nucleic acid.

The microorganisms of the invention are generally configured for increased expression of any one or more of RSP2144, RSP1091, RSP1090, RSP1089, RSP1088, RSP1087, and homologs thereof. The microorganisms may be configured to express these enzymes in a singlet oxygen ($^1O_2$)- and/or $\sigma^E$-independent manner. In some versions, the microorganisms of the invention are configured for increased expression of at least one, at least two, or all of RSP2144 or a homolog thereof, RSP1091 or a homolog thereof, and RSP1090 or a homolog thereof. In some versions, the microorganisms of the invention are configured for increased expression of at least one, at least two, or all of RSP2144 or a homolog thereof, RSP1091 or a homolog thereof, and RSP1090 or a homolog thereof together with increased expression of least one, at least two, or all of RSP1089 or a homolog thereof, RSP1088 or a homolog thereof, and RSP1087 or a homolog thereof. The enzymes may be expressed from individual nucleic acids or as a unit from a single nucleic acid, such as from an operon.

The expression of the enzymes may be increased by any of the methods discussed herein or otherwise known in the art, including placing the enzyme coding sequence under the control of a more active promoter, increasing the copy number of the gene of the enzyme, introducing a translational enhancer on the gene of the enzyme, modifying factors that control expression of the gene, and/or other methods.

The expression of the enzymes may be increased by modifying the microorganism to increase the activity of $\sigma^E$ of *R. sphaeroides* or a homolog thereof. The $\sigma^E$ of *R. sphaeroides* has a sequence of SEQ ID NO:14. Methods of increasing the activity of the $\sigma^E$ of *R. sphaeroides* are described in U.S. Pat. No. 8,003,390, which is attached hereto and is incorporated by reference in its entirety. Exemplary methods of increasing the activity of $\sigma^E$ include increasing expression of $\sigma^E$ (e.g., by increasing the copy number of the gene, etc.), thereby out-titrating the abundance $\sigma^E$ with respect to its inhibitor, the anti-sigma factor ChrR; introducing mutated forms of $\sigma^E$ that do not bind or bind inefficiently to ChrR; introducing mutated forms of ChrR that do not bind or bind inefficiently to $\sigma^E$, deleting ChrR; or otherwise modifying the microorganism in any other manner that reduces or ablates the activity of ChrR in binding $\sigma^E$ and/or reduces or ablates the activity of $\sigma^E$ in binding ChrR. Mutations to $\sigma^E$ that disrupt its ability to bind ChrR include any one, all, or combination of K38E, K38R, and M42A. See Greenwell et al. 2011 and U.S. Pat. No. 8,003,390. The sequence of ChrR is represented by SEQ ID NO: 13. Mutations to ChrR that disrupt its ability to bind $\sigma^E$ include any one, all or combination of H6A, H31A, C35A, C35S, C38A, C38S, C38R and C187/189S. See Greenwell et al. 2011 and U.S. Pat. No. 8,003,390.

Any of the methods described above for increasing the activity of $\sigma^E$ can be performed for homologs of $\sigma^E$ or homologs of ChrR in organisms other than *R. sphaeroides*. Homologs of $\sigma^E$ include proteins having sequences at least about 60%, 65%, 70%, 75%, 80%, 85%, 90%, 95%, 97%, 99%, or more identical to SEQ ID NO:14. Homologs of ChrR include proteins having sequences at least about 60%, 65%, 70%, 75%, 80%, 85%, 90%, 95%, 97%, 99%, or more identical to SEQ ID NO:13. Homologs of $\sigma^E$ and ChrR in microorganisms other than *R. sphaeroides* are known in the art. See Ziegelhoffer et al. 2009 and Dufour et al. 2008.

In some versions of the invention, the microorganism is modified to reduce or ablate the activity of any one or more of RSP2144, RSP1091, RSP1090, RSP1089, RSP1088, RSP1087, and homologs thereof. Such a modification that reduces or ablates the activity of a gene product such as an enzyme in a microorganism is referred to herein as a "functional deletion" of the gene product. "Functional deletion" or its grammatical equivalents refers to any modification to a microorganism that ablates, reduces, inhibits, or otherwise disrupts production of a gene product, renders a produced gene product non-functional, or otherwise reduces or ablates a produced gene product's activity. Accordingly, in some instances, a gene product that is functionally deleted means that the gene product is not produced by the microorganism at all. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. Various methods for introducing genetic modifications are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). Various other genetic modifications that functionally delete a gene product are described in the examples below. In some versions, functional deletion can be accomplished by expressing ribozymes or antisense sequences that target the mRNA of the gene of interest. Functional deletion can also be accomplished by inhibiting the activity of the gene product, for example, by chemically inhibiting a gene product with a small-molecule inhibitor, by expressing a protein that interferes with the activity of the gene product, or by other means. Other aspects of functionally deleting gene products are described in U.S. Pat. No. 8,846,329 and can be applied to the enzymes described herein.

Functionally deleting any one or more of RSP2144, RSP1091, RSP1090, RSP1089, RSP1088, RSP1087, and homologs thereof can enhance the production of certain fatty acids. For example, functionally deleting RSP1090 or a homolog thereof can result in enhanced production of cyclic fatty acids such as 11,12-methylene-octadec-11-enoate. Production of the cyclic fatty acids can be further enhanced by coupling the functional deletion of RSP1090 or a homolog thereof with increased expression of RSP2144 or a homolog thereof and/or RSP1091 or a homolog thereof. In another example, functionally deleting RSP1091 or a homolog thereof, either alone or together with RSP1090 or a homolog thereof, can result in enhanced production of branched-chain fatty acids such as 11-methyl-octadecenoate. Production of the branched-chain fatty acids can be further enhanced by coupling the function deletion of RSP1091, RSP1090, or homologs thereof with increased expression of RSP2144 or a homolog thereof.

In general, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologous sequences of the sequences described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the sequences described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is any nucleic acid or amino acid sequence described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

In vivo methods of producing non-straight-chain fatty acids comprise culturing a microorganism of the invention in conditions suitable for growth of the microorganism. The microorganism either directly produces the fatty acids of interest or produces precursors from which the fatty acids of interest can be converted. Such conditions include providing suitable carbon sources for the particular microorganism along with suitable micronutrients. For eukaryotic microorganisms and heterotrophic bacteria, suitable carbon sources include various carbohydrates. For phototrophic bacteria, suitable carbon sources can include an organic carbon source with or without added $CO_2$, which is provided together with light energy or in the absence of light. If provided in the absence of light, oxygen or another electron acceptor is provided. Culturing the microorganism to produce a furan-containing fatty acid is preferably performed in the presence of oxygen.

The fatty acids produced by the microorganisms can then be isolated from the microorganisms by methods known in the art or developed in the future. Exemplary methods include gas chromatography, as described in the following examples. As the furan-containing fatty acid is an anti-oxidant, it is prone to degradation by some reactive oxygen species. Standard methods to prevent chemical auto-oxidation or degradation of the furan-containing fatty acid product by reactive oxygen species are preferably employed during its isolation.

In vitro methods of producing non-straight-chain fatty acids comprise contacting a first fatty acid in vitro with any one or more enzymes selected from the group consisting of RSP2144, RSP1091, RSP1090, RSP1089, RSP1088, RSP1087, and homologs thereof to generate a second fatty acid. The first fatty acid may comprise any one or more of a straight-chain fatty acid, a branched-chain fatty acid, and a cyclic fatty acid. The second fatty acid may comprise any one or more of a branched-chain fatty acid, and a cyclic fatty acid, and a furan-containing fatty acid. The first and second fatty acids may comprise purified, semi-purified, or unpurified fatty acids. The first and second fatty acids may be saturated or unsaturated. If saturated, the straight-chain fatty acids may be desaturated before contacting them with the one or more enzymes. If unsaturated, the straight-chain fatty acids may be cis or trans across the double bond. The first and second fatty acids may have a hydrocarbon length of from about 6 to about 30 carbons, such as from about 16 to about 26 carbons or from about 16 to about 22 carbons. The first and second fatty acids may be in a free fatty acid form, a salt form, an esterified form (e.g., phospholipid, sterol ester, glyceride), or other form. In some versions of the invention, the first and/or second fatty acids comprise a contiguous chain of 18 carbons. Such a contiguous chain includes the carbon in the carboxyl moiety, excludes any terminal carbon branches on the hydrocarbon chain, and may include or exclude any carbon rings on the hydrocarbon chain.

In exemplary in vitro methods, a straight-chain fatty acid such as vaccenic acid as a first fatty acid may be contacted with at least RSP2144 or a homolog thereof to yield a branched fatty acid such as 11-methyl-octadecenoate as a second fatty acid. This reaction is preferably performed in the presence of a chemically reactive methyl group, such as S-adenosyl methionine (SAM). A branched fatty acid such as 11-methyl-octadecenoate as a first fatty acid may be contacted with at least RSP1091 or a homolog thereof to yield a cyclic or cyclopropene fatty acid such as 11,12-methylene-octadec-11-enoate as a second fatty acid. This reaction is preferably performed in the presence of a flavin or pyridine nucleotide cofactors such as $FADH_2$, NADH, or NADPH. A cyclic or cyclopropene fatty acid such as 11,12-methylene-octadec-11-enoate as a first fatty acid may be contacted with at least RSP1090 or a homolog thereof to yield a furan-containing fatty acid such as 10,13-epoxy-11-methyl-octadecadienoate as a second fatty acid. This reaction is preferably performed in the presence of oxygen, such as air or an external source of $O_2$ gas. RSP1089, RSP1088, RSP1087, and/or homologs thereof may be included in any of the above-mentioned reactions. Such reactions may occur individually in separate reaction compositions or in combination in a single reaction composition.

The invention also provides methods of scavenging reactive oxygen species. The methods comprise contacting a reactive oxygen species with an isolated furan-containing fatty acid. The furan-containing fatty acid may include from about 6 to about 30 carbons, such as from about 16 to about 26 carbons or from about 16 to about 22 carbons, and may be saturated or unsaturated. If unsaturated, the produced furan-containing fatty acid may be cis or trans across the double bond. The furan-containing fatty acid may be in a free fatty acid form, a salt form, an esterified form (e.g., phospholipid, sterol ester, glyceride), or other form. In exemplary versions, the furan-containing fatty acid comprises 10,13-epoxy-11-methyl-octadecadienoate. In exemplary versions, the reactive oxygen species comprises $^1O_2$. The furan-containing fatty acid may be produced and/or isolated by any methods described herein. Contacting the reactive oxygen species with the isolated furan-containing fatty acid may occur in vivo or in vitro.

As used herein, the term "increase," whether used to refer to an increase in production of a fatty acid, an increase in expression of an enzyme, etc., generally refers to an increase from a baseline amount, whether the baseline amount is a positive amount or none at all.

The elements and method steps described herein can be used in any combination whether explicitly described or not.

The singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

Examples

Background

Fatty acids have crucial, yet diverse, roles in biology. In cells and organelles, fatty acids maintain bilayer stability, provide a permeability barrier, act as secondary messengers in signaling pathways, and aid the function of integral membrane proteins (Mueller et al. 2008, Cronan 2002, Cronan 2003). Fatty acids also help maintain viability in response to temperature and environmental changes, and can be targets for modification by reactive oxygen species or membrane-active agents (Cronan 2002, Cronan 2003, Chang et al. 1999, Girotti et al. 2004, Imlay 2003, Sayre et al. 2006, Watabe et al. 2007). Fatty acids, or the products derived from them, are valuable as food additives, specialty chemicals, and petroleum substitutes (Lennen et al. 2010, Peralta-Yahya et al. 2012, Connor et al. 2009, Lands 2012). Thus, there is considerable interest in understanding the suite of fatty acids that can be made by native or engineered pathways.

The following examples demonstrate a previously unreported ability of the photosynthetic bacterium *Rhodobacter sphaeroides* to produce furan-containing fatty acids (Fu-FAs), an important, yet poorly understood class of compounds. The presence of Fu-FAs has been reported previously in plants, fish, and some bacteria (Spiteller 2005). Based on their chemical properties, it is proposed that Fu-FAs could provide bilayer protection against radicals or organic peroxides that reduce membrane function (Spiteller 2005, Okada et al. 1996, Okada et al. 1990). The oxygen atom within Fu-FAs also provides a functional group for modifications that could increase their industrial value (Spiteller 2005).

The following examples show the high abundance of the 19-carbon furan-containing fatty acid, 10,13-epoxy-11-methyl-octadecadienoate (19Fu-FA), in phospholipids isolated from an *R. sphaeroides* mutant lacking an anti-sigma factor, ChrR. This *R. sphaeroides* mutant has increased transcription of genes that are normally activated in the presence of the reactive oxygen species (ROS) singlet oxygen ($^1O_2$). In this and other phototrophs, $^1O_2$ is a byproduct of light energy capture in integral membrane complexes of the photosynthetic apparatus (Girotti et al. 2004, Ziegelhoffer et al. 2009, Glaeser et al. 2011). Consequently, fatty acids or other membrane components are likely targets for damage by $^1O_2$ (Ziegelhoffer et al. 2009, Glaeser et al. 2011).

Despite the proposed roles of Fu-FAs, little is known about how they are synthesized (Spiteller 2005). The following examples show proteins needed for the conversion of unsaturated fatty acids to 19Fu-FA. The examples show that a $^1O_2$-inducible protein (RSP2144), is an S-adenosyl methionine (SAM)-dependent methylase that synthesizes a 19 carbon methylated unsaturated fatty acid (19M-UFA) from vaccenic acid both in vivo and in vitro. The examples also identify gene products needed for the $O_2$-dependent conversion of 19M-UFA to 19Fu-FA (Lemke et al. 2014). Further, the examples demonstrate that the presence of $^1O_2$ leads to the disappearance of 19Fu-FA in vivo. A pathway for Fu-FA synthesis is proposed, as is a protective role for compounds in the presence of a ROS like $^1O_2$.

Material and Methods

Bacterial Strains and Growth.

*Escherichia coli* and *R. sphaeroides* strains were grown as described (Anthony et al. 2005). Mutant strains 41091/ΔChrR and 1091:sp$^R$/ΔChrR were made using methods described previously (Nam et al. 2013). The strains and plasmids used throughout the examples are shown in Tables 1 and 2, respectively.

Purification of His$_6$-RSP2144 Protein.

pRLhisRSP2144 was generated by cloning the RSP2144 coding region of *R. sphaeroides* (Kontur et al. 2012) into the NdeI and EcoRI sites of pET-28a(+) to produce an N-terminally hexahistidine-tagged protein (His$_6$-RSP2144). A 500-ml culture of log phase BL21DE3 *E. coli* cells, containing pRLhisRSP2144, was exposed to 1 mM isopropyl β-d-1-thiogalactopyranoside (IPTG) for 4 hrs at 28° C. to induce expression of His$_6$-RSP2144. The cells were harvested by centrifugation and the resulting pellet was resuspended in lysis buffer (25 mM HEPES pH 7.5, 150 mM KCl, 20 mM imidazole, 10% glycerol, 1 mg/ml lysozyme, and 1× Halt protease inhibitor (Pierce)), sonicated on ice, pulsing every 20 s, for 7 min, and centrifuged for 1 hr at 50,000 g. The resulting supernatant was passed over a 4 ml Ni-NTA agarose column (Novagen), washed with 50 ml wash buffer (25 mM HEPES pH 7.5, 150 mM KCl, 50 mM imidazole, and 10% glycerol) and protein removed with 16 ml elution buffer (25 mM HEPES pH 7.5, 150 mM KCl, 250 mM imidazole, and 10% glycerol). Fractions containing the most protein were combined and concentrated using a YM10 centrifugal filter (Millipore) and dialyzed into 50 mM HEPES, 10 mM sodium bicarbonate, and 50% glycerol. Small portions were aliquotted and stored at −80° C. Protein concentration was estimated using the Bradford Assay (Bio-Rad).

In Vitro Assay of His$_6$-RSP2144 Activity.

The phospholipid substrate was purified from a ΔRSP2144 strain and a phospholipid micelle solution (in water) was created (Courtois et al. 2004) and quantitated by a lipid phosphorous assay (Rouser et al. 1970). Each enzyme reaction contained 0.06 to 1.04 mM phospholipid, 4.4 µM His$_6$-RSP2144 protein, 20 mM potassium phosphate buffer pH 7.4, 0.5 mg/ml BSA, 750 µM SAM (Sigma) with a specific activity of 25 µCi/µmol (Perkin Elmer). The reactions were incubated at 30° C. and individual time points were taken by placing 100 µl aliquots into 1 ml 10% trichloroacetic acid (TCA) (v/v). The solutions were filtered over Whatman GF/c glass filter fibers on a 1225 sampling manifold (Millipore), followed by three washes with 1 ml 10% TCA and three washes with 1 ml water. The filters were put into 5 ml Optiphase scintillation fluid (Perkin Elmer) and incubated at room temperature overnight before determining radioactivity on a scintillation counter. The results of duplicate assays were averaged and the reaction rate calculated by plotting radioactivity versus time for each concentration of phospholipid. The rates were averaged among two independent experiments.

Exposure to $^1O_2$.

*R. sphaeroides* strains were exposed to $^1O_2$ as described (Anthony et al. 2004). One mM IPTG was added to cells 1 hr before $^1O_2$ exposure to induce protein expression in cells containing a plasmid-encoded His$_6$-RSP2144 protein. Cells were grown anaerobically by sparging cultures with a 95% $N_2$/5% $CO_2$ gas mixture.

Fatty Acid Methyl Ester (FAME) Content.

All samples from methylene blue-treated cells were kept in the dark until FAMEs were generated and extracted into hexane before analysis by GC-MS. Equal cell numbers, of up to 4 ml cell culture, were added to 8 ml 1:1 v/v methanol:chloroform (Lennen et al. 2010) containing 50 µg or 100 µg pentadecanoic acid as a recovery standard (pentadecanoic acid is not detectable in *R. sphaeroides* fatty acids). The suspension was vigorously agitated and centrifuged at low speed to separate the phases. The organic phase was removed, dried under $N_2$, and lyophilized for 1 hr. FAMEs were prepared by resuspending the dried materials in 600 µl anhydrous methanol (Sigma), adding 100 µl sodium methoxide (Sigma) and incubating at room temperature for 3 hr (Christie 2010). The reaction was stopped by adding 600 µl 2 N HCl, and FAMEs were extracted with 600 µl hexane. One µl of each sample was analyzed on an Agilent 7890A/5975C GC-MS with differing split ratios with an HP-5 ms capillary column and He carrier gas (20 cm/s at 150° C.) using one of two oven programs: (A) 150° C. isothermal for 4 min, 4° C./min ramp to 250° C., and isothermal at 250° C. for 5 min; (B) 150° C. isothermal for 4 min, 6° C./min ramp to 245° C., isothermal at 245° C. for 2 min, 80° C./min ramp to 325° C., and isothermal at 325° C. for 2 min. Chromatograms and mass spectra were analyzed using Agilent GC/MS ChemStation (version E.02.00.493) and MassHunter software (version B.06.00; Agilent Technologies) and compared with the NIST MS Search 2011b library. For quantification, a set of appropriate FAME standard curves were created from a mix of Supelco C8-C24 standards (for C16:0, C16:1, C18:0), C15:0, C18:1 (Sigma), methyl 11-methyl-octadecenoate (n-6) (19M-UFA), and 10,13-epoxy-11-methyl-octadecadienoate (19Fu-FA) (Larodan). The MassHunter integration peak filter was set to >5% of the largest peaks; peak area was integrated for ions diagnostic for each FAME (m/z 74 for C15:0, C16:0, C18:1, and C18:0; m/z 55 for C16:1, m/z 69 for 19M-UFA, and m/z 165.1 for 19Fu-FA). The integrated areas were normalized to the recovery standard (C15:0), and each FAME was converted to a percentage of the total fatty acids, followed by averaging data from technical duplicates. Biological duplicates were averaged, and the standard deviation (SD) was calculated.

Ectopic Expression of RSP2144 in *R. sphaeroides* and *E. coli*.

pRL101 was created by cloning the $His_6$-RSP2144 gene from pRLhisRSP2144 into the NdeI and HindIII sites of pIND5. This plasmid and pAYW19 (containing *E. coli* cfa) were then transformed into the *E. coli* strain JW1653, which lacks cfa. JW1653 was obtained from the Keio collection and the $Kn^r$ gene was removed before use (Baba et al. 2006). Triplicate biological cultures were separately treated with 1 mM IPTG before preparing FAMEs (see section entitled "fatty acid methyl ester (FAME) content" above).

Hydrogenation of FAME Samples.

FAMEs were dried under $N_2$, dissolved in 10 ml (1:2 v/v) chloroform:methanol: with 15 mg 5% platinum on activated charcoal (Montanari et al. 2010). The reaction tubes were fitted with stoppers and sparged with a 95% $N_2$/5% $H_2$ gas mixture for 1 hr. The tubes were centrifuged twice to remove the charcoal, filtered through glass wool in a Pasteur pipet, and analyzed by GC/MS.

Identification of Unknown FAMEs.

Gas chromatography was performed on a Trace GC Ultra (Thermo Electron, Milan, Italy) equipped with a CTC Analytics GC PAL autosampler (Zwingen) using a 30 m×0.25 mm (ID)×0.25 µm ($d_f$) Crossbond 5% diphenyl/95% dimethyl polysiloxane column (Restek Rxi-5Sil MS, Bellefonte, Pa.) and He as carrier gas. Mass spectrometry was performed on a breadboard GC/quadrupole-Orbitrap MS (Peterson et al., Part I 2014; Peterson et al., Part II 2014). See also Lemke et al. 2014.

A FAME mix of 26 compounds in methyl caproate, was used for chromatographic and MS source optimization (Sigma). Samples in hexane (1 µL) were injected via the hot-needle technique at various split ratios depending on sample concentration, with an injector temperature of 250° C., He flow rate of 1 mL/min, and the following oven program: 1 min isothermal at 150° C., 15° C./min to 250° C., 1 min isothermal at 250° C., 80° C./min to 320° C., and 2 min isothermal at 320° C. The transfer line and source temperatures were 280° C. and 250° C., respectively. Samples were ionized via EI or positive CI (PCI) using acetonitrile (ACN) as the reagent gas (70 eV). Full-scan analyses employed a scan range of 75-400 Th, resolution of 17,500, automated gain control (AGC) target of 1E6, and maximum injection time of 100 ms. Targeted MS/MS analyses employed a 3 Th isolation width, normalized collision energy of 25 eV, resolution of 17,500, AGC target of 1E6, and maximum injection time of 250 ms.

To enable ACN PCI, a 250 µm (i.d.) fused silica capillary connected an ACN reservoir (6 mL) directly to the MS source through the heated transfer line. A two-holed ferrule was used to permit entry of both the GC column and ACN capillary into the transfer line. Although the column extended into the source, the ACN capillary was set back ~5 cm from the source to prevent interference with the GC eluent. A medium-flow metering valve (Swagelok) was placed between the reservoir and transfer line to regulate the flow of ACN into the source. A source pressure of 7.1E-5 Torr, ~0.2 ms reagent injection time (at a 1E6 AGC target), and m/z 42 (protonated ACN)-to-m/z 54 (1-methyleneimino-1-ethenylium, or MIE) ratio of 5:1 were found to be optimal for generation of molecular ion MIE-adducts of unsaturated FAMEs.

Identification of Fatty Acyl Isomers.

Identification of isomer configuration of 11-methyl-octadecanoate was determined by gas chromatography equipped with a flame ionization detector (6890N, Agilent technologies). Commercial FAME standards (18:0, $18:1\Delta9^{cis}$, $18:1\Delta11^{cis}$, $18:1\Delta9^{trans}$, and M-$UFA^{trans}$) and biological samples were separated on a DB-23 capillary column 30 m×0.25 mm (i.d.), 0.25-µm film thickness. The He flow rate was 1.5 mL/min, and the following oven program was run: 3 min isothermal at 140° C., 5° C./min to 230° C., and isothermal at 230° C. for 3 min. Injector and detector were maintained at 250° C. throughout the analysis. Isomers in biological samples were identified by retention time comparison with FAME standards (Tjellström et al. 2013).

TABLE 1

Strains

| Strain | Relevant genotype | Source |
|---|---|---|
| *E. coli* | | |
| DH5α | supE44 lacul69(φ80 lacZ M15) hsdR178 recA1 endA1 gyrA96 thi-1 relA-1 | Bethesda-Research Laboratories 1986 |
| S17-1 | C600::RP-4 2-(Tc::Mu) (Kn::Tn7) thi pro hsdR hsd $M^+$ recA | Simon et al. 1983 |
| BL21(DE3) | $F^-$ ompT hsdSB ($r^{B-}$ $m^{B-}$) gal dcm (DE3) | Novagen |
| JW1653 | cfa::kan of BW25113 Keio Collection | Baba et al. 2006 |
| RLcfaK49-6 *R. sphaeroides* | cfa markerless deletion mutant of JW1653 | This study |
| 2.4.1 | Wild type | Kontur et al. 2012 |
| TF18 | rpoE::drf | Newman et al. 1999 |
| ΔChrR | chrR::drf | Schilke et al. 1995 |
| ΔRSP2144 | RSP2144::Ω $Sm^rSp^r$ | Nam et al. 2013 |
| RSL1 | ΔchrR RSP2144::Ω $Sm^rSp^r$ | This study |
| 1091:$sp^R$/ΔChrR | $ΩSp^R$ insertion in RSP1091 coding sequence in ΔChrR | This study |
| ΔRSP1091/ΔChrR | In-frame deletion of both RSP1091 and ΔChrR | This study |
| ΔRSP1090/ΔChrR | In-frame deletion of both RSP1090 and ΔChrR | This study |

TABLE 2

Plasmids

| Plasmid | Relevant genotype | Source |
|---|---|---|
| pBlueScriptII KS- | Ap$^r$ | Agilent Technologies |
| pRS2144 | RSP2144 in pBSII | Nam et al. 2013 |
| pET-28a+ | His$_6$ expression vector, Kn$^r$ | Novagen |
| pRLhisRSP2144 | 1.2 kb RSP2144 fragment from pRS44 cloned into NdeI/EcoRI-cut pET-28a | This study |
| pIND5 | pIND4 NcoI site replaced with NdeI site, Kn$^r$ | Nam et al. 2013 |
| pRL101 | 1.3 kb fragment amplified from pRLhisRSP2144 cloned into NdeI/HindIII pIND5 | This study |
| pRL591 | 1.3 kb fragment containing RSP1091 amplified from genomic R. sphaeroides DNA cloned into NdeI/HindIII pIND5 | This study |
| pRL590 | 0.8 kb containing RSP1090 fragment amplified from genomic R. sphaeroides DNA cloned into NdeI/HindIII pIND5 | This study |
| pRL59190 | 2.1 kb fragment containing RSP1091 and RSP1090 amplified from genomic R. sphaeroides DNA cloned into NdeI/HindIII pIND5 | This study |
| pAYW19 | E. coli cfa gene on pGEMS, Ap$^r$ | Wang et al. | integral membrane proteins of the photosynthetic apparatus (Ziegelhoffer et al. 2009, Glaeser et al. 2011, Anthony et al. 2004). At least one open reading frame, which is a known member of the $\sigma^E$ regulon, RSP2144, encodes a protein with amino acid similarity to an enzyme predicted to modify fatty acids (Ziegelhoffer et al. 2009, Glaeser et al. 2011, Anthony et al. 2004, Nam et al. 2013, Dufour et al. 2008). To test for $\sigma^E$-dependent alterations in fatty acid composition, fatty acyl methyl esters (FAMEs) were prepared in order to compare the fatty acid content of wild-type cells and mutant cells (ΔChrR; see Table 1 for strain designations), which have high $\sigma^E$ activity when grown aerobically in the absence of light because the antisigma factor ChrR that normally inhibits $\sigma^E$ function has been inactivated (Anthony, 2004, Anthony, 2005, Nam, 2013, Newman, 1999).

Figure 1A:
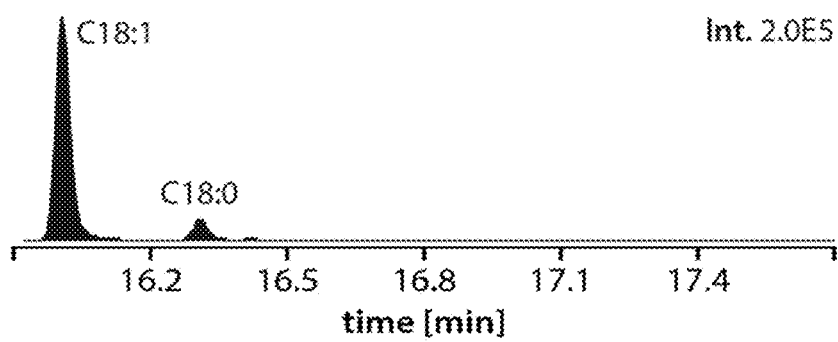
FIGS. 1A-1D show gas chromatograms of fatty acid methyl esters (FAMEs) of fatty acids from various *Rhodobacter sphaeroides* cells, including wild type cells (FIG. 1A), ΔChrR cells (FIG. 1B), ΔRSP2144 cells (FIG. 1C), and ΔRSP2144 cells ectopically expressing the RSP2144 gene from an IPTG-inducible plasmid (FIG. 1D). FAMEs known to be present in wild type *R. sphaeroides* (C18:0 and C18:1) are indicated, as are two additional FAMEs of fatty acids (19M-UFA (11-methyl-octadecenoate (n-6), see below) and 19Fu-FA (10,13-epoxy-11-methyl-octadecadienoate, see below)) that accumulate in ΔChrR cells. The Y- and X-axes show the relative abundance and retention time for each species, respectively.

In wild type cells, the expected major FAME products (C18:1, C18:0, C16:1, C16:0; Table 3) based on published fatty acid analysis of R. sphaeroides (Donohue et al. 1982, Hands et al. 1962, Qureshi et al. 1988, Russell et al. 1979) were found (FIG. 1A). In ΔChrR cells, the accumulation of two additional FAME products (retention times of ~16.4 and 17.5 minutes, FIG. 1B) was observed. A lower level of the vaccenic acid (C18:1) FAME in the ΔChrR cells compared to wild type cells was also observed (Table 3, FIG. 1B). It was concluded that increased $\sigma^E$ activity alters the cellular fatty acid composition. Neither of the two additional FAME products in cells containing increased $\sigma^E$ activity eluted with

TABLE 3

Relative cellular fatty acid content*

| | C16:1 | C16:0 | C18:1 | C18:0 | M-UFA† | FFA‡ | N |
|---|---|---|---|---|---|---|---|
| WT Aero | 5.3 (0.6) | 21.1 (3.1) | 45.9 (6.7) | 25.7 (2.9) | 1.3 (0.2) | 0.6 (0.2) | 3 |
| WT Photo | 5.1 (0.1) | 18.6 (0.1) | 48.3 (1.3) | 26.3 (0.7) | 1.7 (0.1) | ND | 2 |
| ΔChrR Aero | 5.7 (0.3) | 23.3 (1.2) | 40.0 (2.3) | 26.4 (1.1) | 2.5 (1.1) | 2.3 (0.2) | 3 |
| ΔChrR Photo | 5.4 (0.3) | 21.4 (2.0) | 42.8 (4.6) | 25.9 (3.4) | 4.6 (0.7) | ND | 3 |
| ΔUfaM Aero | 5.0 (0.2) | 21.4 (1.3) | 47.4 (2.4) | 26.0 (1.2) | ND | ND | 3 |
| ΔUfaM Photo | 4.2 (0.4) | 18.1 (5.1) | 51.8 (11.9) | 25.5 (6.4) | ND | ND | 2 |
| RSL1 Aero | 5.4 (0.8) | 24.5 (3.0) | 45.3 (6.3) | 24.5 (2.5) | ND | ND | 3 |
| RSL1 Photo | 4.5 (0.1) | 19.1 (0.5) | 49.7 (0.6) | 26.4 (1.4) | ND | ND | 3 |
| 1091:sp$^R$/ΔChrR$^2$ Aero§ | 5.0 (0.3) | 22.6 (0.3) | 40.1 (0.7) | 23.1 (0.5) | 9.2 (0.6) | ND | 2 |
| 1091:sp$^R$/ΔChrR$^2$ Photo | 5.2 (0.4) | 19.9 (0.6) | 43.5 (2.6) | 24.6 (1.6) | 6.8 (0.1) | ND | 3 |
| Δ1091/ΔChrR$^2$ Aero¶ | 3.9 (1.2) | 21.5 (1.4) | 43.4 (3.2) | 22.5 (0.4) | 8.7 (1.7) | ND | 3 |
| Δ1091/ΔChrR$^2$ Photo | 5.1 (0.2) | 21.6 (1.4) | 39.5 (2.4) | 26.8 (0.4) | 7.1 (0.5) | ND | 3 |

*% of the total fatty acid, with standard deviation in parentheses;
ND = <0.5% of the total FAME;
N = number of biological replicates
†M-UFA is methyl 11-methyl-C18:1 (n-6).
‡FFA is 10,13-epoxy-11-methyl-octadecadienoate.
§1091:sp$^R$ cells contain a polar insertion of a spectinomycin-resistance gene in RSP1091.
¶Δ1091 cells contain an in frame-deletion in RSP1091.

Results

Increased $\sigma^E$ Activity Alters Cellular Fatty Acid Composition.

Fatty acids are targets for direct or indirect damage by ROS (Mueller et al. 2008, Girotti et al. 2004, Imlay 2003, Sayre et al. 2006, Watabe et al. 2007, Ziegelhoffer et al. 2009), particularly when ROS are produced by integral membrane enzymes in the respiratory chain or the photosynthetic apparatus (Mueller et al. 2008, Sayre et al. 2006, Watabe et al. 2007, Ziegelhoffer et al. 2009, Koopman et al. 2010). The R. sphaeroides $\sigma^E$ protein activates a transcriptional stress response to $^1O_2$, a ROS that is generated by compounds in bacterial fatty acid standard mixtures. The identity of these products was therefore sought.

Identification of Additional FAMEs in Cells with Increased $\sigma^E$ Activity.

Figure 1B:
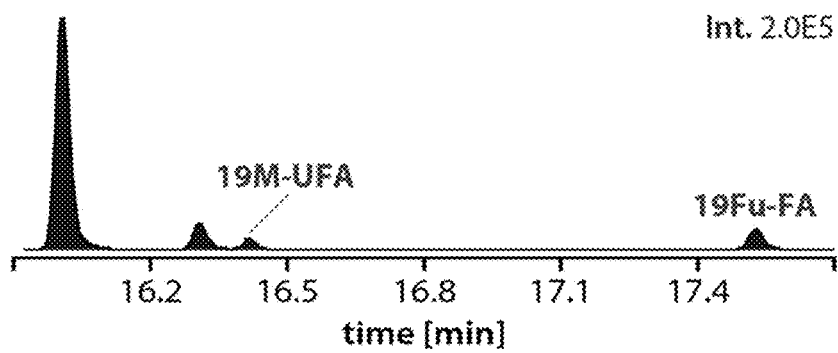
Figure 1C:
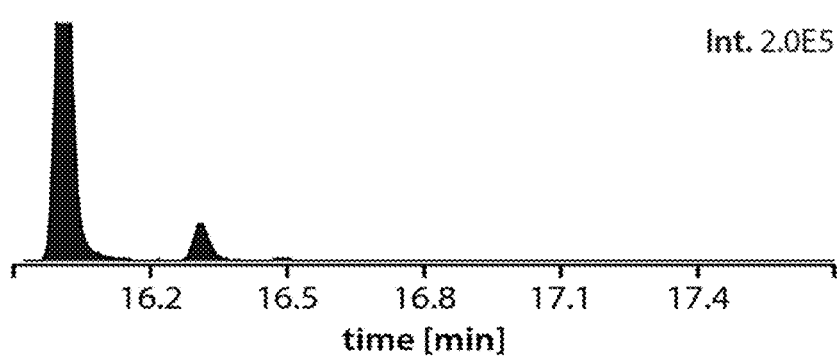
Figure 2A:
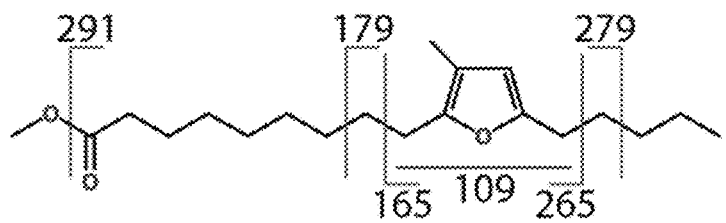
FIG. 2A shows fragmentation sites on methyl 10,13-epoxy-11-methyl-octadecadienoate in electron ionization.
Figure 2B:
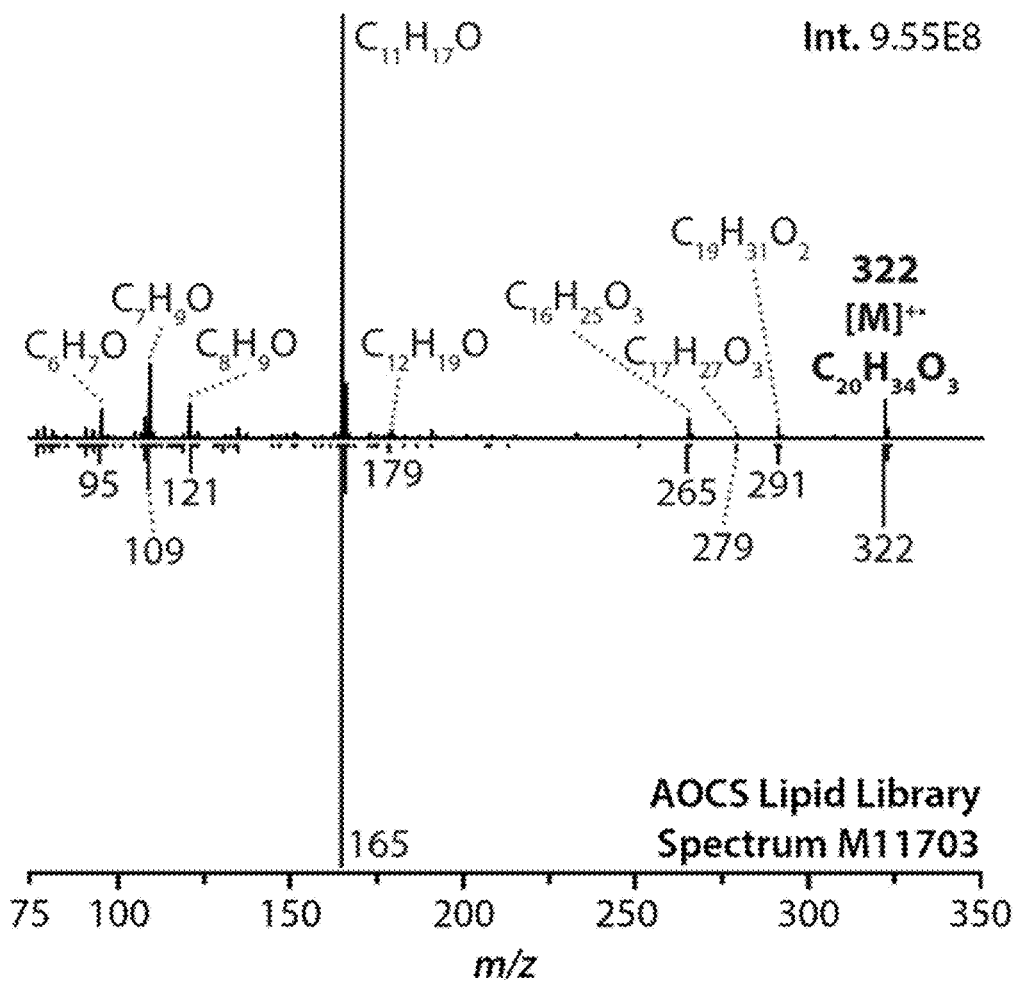
FIG. 2B shows the electron ionization spectrum and interpretation of major fragment ions of the 19Fu-FA FAME indicated in FIG. 1B (top trace) and its comparison to the reference library spectrum for methyl 10,13-epoxy-11-methyl-octadecadienoate (bottom trace). Library spectrum adapted from the American Oil Chemists' Society (AOCS) Lipid Library, spectrum number M11703.

The electron ionization (EI, 70 eV) mass spectrum of one of the unknown FAMEs derived from cells with increased $\sigma^E$ activity (retention time ~17.5 min in FIG. 1B) showed that it has an intact molecular ion mass of 322.2502 Da. This ion mass corresponds to a molecular formula of $C_{20}H_{34}O_3$ (FIGS. 2A and 2B). The fragmentation pattern of this FAME (FIG. 2A and top trace of FIG. 2B) had a good correlation with a methyl ester of a 19-carbon furan-containing fatty acid, 10,13-epoxy-11-methyl-octadecadienoate (9-(3- methyl-5-pentylfuran-2-yl)nonanoic acid), as seen by the comparison with the reference spectrum (FIG. 2A and bottom trace of FIG. 2B) (Spectrum M11703, American Oil Chemists' Society (AOCS) Lipid Library). The 10,13-epoxy-11-methyl-octadecadienoate found in the ΔChrR cells is hereafter referred to as 19Fu-FA.

Figure 3A:
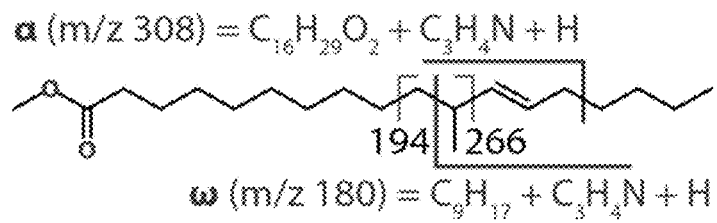
FIG. 3A shows fragmentation sites on 19M-UFA in electron ionization.
Figure 3B:
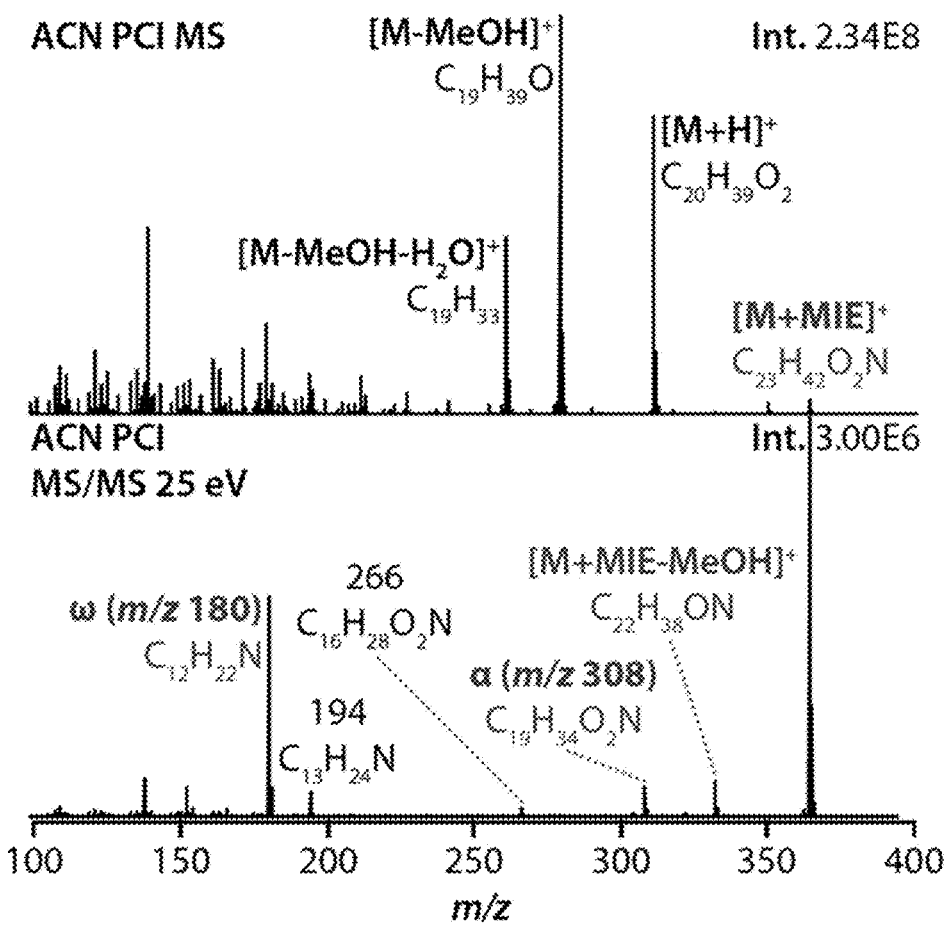
FIG. 3B shows mass spectroscopy (MS)

The other unidentified FAME derived from cells with increased $\sigma^E$ activity (retention time ~16.4 minutes in FIG. 1B) had an intact molecular ion mass of 310.2866 Da, corresponding to an elemental composition of $C_{20}H_{38}O_2$ (FIGS. 3A and 3B). The EI mass spectrum of this FAME did not allow a definitive assignment of its identity, so additional experiments were necessary. Hydrogenation of the FAME led to a shift in retention time (FIG. 4A) and an increase in the intact molecular ion mass by 2 Da (312.3023 Da, $C_{20}H_{40}O_2$) (FIG. 4C). The increase in the mass of this FAME after hydrogenation indicates that the untreated molecule is unsaturated. The EI mass spectrum of the 312 Da hydrogenated unknown contained diagnostic a and b fragment ions that localized a methyl branch at position 11 on the hydrogenated molecule, and by extension on the non-hydrogenated unknown (FIGS. 4B and 4C). This spectrum correlates well with the reference spectrum of methyl 11-methyl-octadecanoate (Spectrum 112141, National Institutes of Standards and Technology (NIST) Library) (FIGS. 4B and 4D). To then localize the position of the double bond in the acyl chain of the 310 Da unsaturated, faster-migrating unknown, a soft ionization technique (Michaud et al. 2002), acetonitrile (ACN) positive chemical ionization (PCI), was employed with subsequent isolation and MS/MS of a chemical ionization-derived molecular ion adduct $\{[M+1\text{-methyl-eneimino-1-ethenylium (MIE)}]^+\}$ of the (non-hydrogenated) unknown FAME. The ACN PCI MS/MS fragmentation pattern of this compound contains diagnostic fragment ions, α and ω, that localize the double bond in the acyl chain to position 12 (FIGS. 3A and 3B). This unknown FAME was thus identified as methyl 11-methyl-C18:1 (n-6), the precursor fatty acid of which is hereafter referred to as 19M-UFA. The 19M-UFA produced in ΔChrR cells was determined to have a trans configuration around the double bond (FIG. 5). As the 19M-UFA is derived from cis-vaccenic acid, the unsaturated fatty acyl methylase (UfaM) activity alters the isomeric state of the fatty acyl molecule in a manner reported for SAM-dependent methylases involved in mycolic acid biosynthesis (Grogan et al. 1997, Yuan et al. 1997).

To validate the assigned identity of these two FAMEs, the behavior of synthetic standard FAMEs of 19M-UFA and 19Fu-FA was compared to those derived from ΔChrR cells. The fragmentation patterns of the synthetic 19M-UFA and 19Fu-FA FAMEs were indistinguishable from the native 19M-UFA and 19Fu-FA FAMEs present in ΔChrR cells (FIGS. 6A-6D).

By using the synthetic FAMEs as quantitative standards, the relative cellular abundance of the 19M-UFA and 19Fu-FA in the cells was estimated. Little of either 19M-UFA or 19Fu-FA was found in aerobically grown wild type cells (FIG. 1A and Table 3), presumably because these cells have low $\sigma^E$ activity (Anthony et al. 2004). By contrast, 19M-UFA and 19Fu-FA constituted ~2.5 and ~2.3%, respectively, of the total FAME products in aerobically grown ΔChrR cells (which contain high $\sigma^E$ activity) (FIG. 1B). There is also decreased abundance of vaccenic acid in the ΔChrR cells compared to the wild type cells (C18:1, FIG. 1B and Table 3), suggesting that both of 19M-UFA and 19Fu-FA are derived from vaccenic acid.

RSP2144 is a SAM-Dependent Fatty Acyl Methylase (UfaM).

The accumulation of 19M-UFA and 19Fu-FA and the reduction in vaccenic acid in ΔChrR cells could reflect the use of a mono-unsaturated fatty acyl chain as a substrate for synthesis of one or both of these products. RSP2144 is annotated as a SAM-dependent fatty acyl modifying enzyme with significant amino acid similarity to bacterial cyclopropane fatty acid synthase (Ziegelhoffer et al. 2009, Anthony et al. 2004, Dufour et al. 2008). However, RSP2144 does not appear to catalyze this reaction, because ΔChrR cells, which have increased RSP2144 expression (Anthony et al. 2004, Dufour et al. 2008), do not contain detectable levels of a C19 cyclopropane FAME (FIG. 1A and Table 3).

Thus, it was hypothesized that RSP2144 is a previously uncharacterized SAM-dependent unsaturated fatty acyl methylase (UfaM). To test this hypothesis, the ability of purified recombinant $His_6$-tagged RSP2144 to methylate fatty acids was tested. Purified $His_6$-RSP2144 catalyzed transfer of a $^3H$-methyl group from methyl-labeled SAM into trichloroacetic acid(TCA)-precipitated material when incubated with a phospholipid substrate mixture isolated from an R. sphaeroides ΔRSP2144 mutant (FIG. 7A). The activity of the recombinant RSP2144 enzyme ($V_{max}$~331 pmol/min/mg) and its apparent affinity for phospholipid substrate ($K_m$~308 μM, FIG. 7A) were comparable with other SAM-dependent fatty acyl modifying enzymes (Guianvarc'h et al. 2006, Iwig et al. 2005). Analyzing the FAME products of this in vitro reaction by GC-MS revealed the accumulation of a product with a retention time (FIG. 7B) and fragmentation pattern (FIG. 7C) identical to the 19M-UFA (methyl 11-methyl-C18:1 (n-6)) accumulating in ΔChrR cells.

It was also found that ectopic expression of $His_6$-RSP2144 in either R. sphaeroides or an Escherichia coli (fa (cyclopropane fatty acid synthase) mutant led to accumulation of 19M-UFA (FIGS. 8A and 8C). Unlike R. sphaeroides, E. coli contains significant amounts of C16:1 (n-7) fatty acyl chains in its phospholipids (Cronan 2002, Cronan 2003), so preferential accumulation of 19M-UFA and the absence of a detectable methyl C17 FAME in E. coli could indicate that RSP2144 has some selectivity for methylation of vaccenic acid. However, there is a bias for having a C16:1 chain at position 2 of phospholipids in E. coli (Magnuson 1993), so the lack of accumulation of a 17 carbon M-UFA in this bacterium could also reflect a preference for UfaM to methylate acyl chains at the 1 position. As a control, it was found that ectopic expression of E. coli cfa in its native host led to accumulation of C17 and C19 cyclopropane FAMEs (FIG. 8B), as expected given the reported function of this enzyme (Guianvarc'h et al., Iwig et al.). Thus, it was concluded that $His_6$-RSP2144 is a previously uncharacterized SAM-dependent unsaturated fatty acid (UFA) methylase, which we hereafter call UfaM.

RSP1091 is Needed for Accumulation of 19Fu-FA.

Figure 1D:
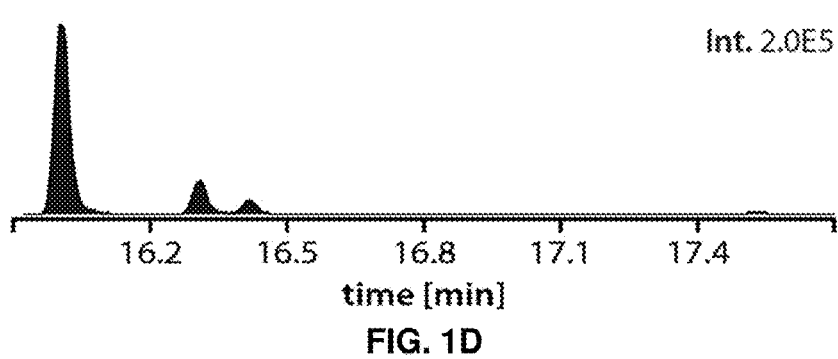

Ectopic expression of $His_6$-RSP2144 in ΔRSP2144 R. sphaeroides resulted in accumulation of 19M-UFA but not 19Fu-FA (FIG. 1D). By contrast, both 19M-UFA and 19Fu-FA accumulated in ΔChrR cells (FIG. 1B and Table 3), which have increased expression of RSP2144 and other proteins in the $\sigma^E$ regulon (Dufour et al. 2008). One interpretation of these data is that another $\sigma^E$-dependent gene is needed to synthesize 19Fu-FA. $\sigma^E$ target genes in the putative RSP1091-1087 operon have amino acid sequence similarity to fatty acid modifying enzymes (Ziegelhoffer et al. 2009, Anthony et al. 2004, Dufour et al. 2008). Thus, it was determined whether any of these proteins had a previously unrecognized role in fatty acid modification.

To test this hypothesis, the FAME content of aerobic cells which lacked ChrR and RSP1091 (Nam et al. 2013) was analyzed. For this analysis, cells containing either an in-frame deletion in the RSP1091 coding sequence or ones which contained an insertion in RSP1091 that might have a polar, i.e. negative, effect on expression of the downstream genes RSP1090-1087 (Nam et al. 2013, Dufour et al. 2008) were used. Fatty acid analysis of either the ΔChrR/ΔRSP1091 double mutants showed that they lacked detectable levels of 19Fu-FA present in the ΔChrR mutant (Table 3). However, both the ΔChrR/ΔRSP1091 double mutants contained the 19M-UFA that is present in the ΔChrR mutant. Thus, it was concluded that RSP1091 is needed for synthesis of 19Fu-FA. Other genes in the putative RSP1091-1087 operon may also be involved in the conversion of 19M-UFA to 19Fu-FA (see below).

Based on only these data, it was deemed possible that the RSP1091 protein either directly converts vaccenic acid to 19Fu-FA, or alternatively, that 19M-UFA produced by the RSP2144 protein could be an intermediate in a RSP1091-dependent pathway for Fu-FA synthesis. To distinguish between these possibilities, the FAME content of cells lacking both ChrR and RSP2144 was compared to cells lacking only ChrR. Analysis of FAMEs from the ΔChrR/ΔRSP2144 double mutant showed that it lacked both the 19M-UFA and 19Fu-FA that accumulate in ΔChrR cells (Table 3). Thus, it was concluded that 19M-UFA, as a product of RSP2144 activity, is needed to produce 19Fu-FA. In addition, it was concluded that RSP1091, either alone or in conjunction with another $\sigma^E$ target gene, converts 19M-UFA into 19Fu-FA.

Role of RSP1090.

The potential role of RSP1090 in the production of 19Fu-FA was assessed. Deletion of RSP1090 (cfaO) in ΔChrR R. sphaeroides mutants resulted in the disappearance of the 19Fu-FA observed in ΔChrR cells and the appearance of a new fatty acid species designated as Ce-FA (FIG. 9, panels B and C). Neither 19Fu-FA nor Ce-FA was present in ΔChrR/ΔufaC (RSP1091) cells, and, instead, M-UFA was particularly abundant in these cells (FIG. 9, panel D). None of M-UFA, 19Fu-FA, and Ce-FA was detectable in ΔChrR/ΔufaM (RSP2144) cells (FIG. 9, panel E). These results suggested that CfaO participates in the production of 19Fu-FA by converting Ce-FA generated by UfaC to Fu-FA. A proposed pathway is shown in FIG. 10.

Identification of Ce-FA.

The fragmentation pattern of the Ce-FA produced by ΔChrR/ΔcfaO (RSP1090) cells (FIG. 11, top trace) had a good correlation with the reference spectrum of methyl 2-octylcyclopropene-1-octanoate (Spectrum 336401, NIST Library) (FIG. 11, bottom trace), which is the methyl ester of 11,12-methylene-octadec-11-enoate. Thus, Ce-FA was identified as 11,12-methylene-octadec-11-enoate.

Enhanced Production of 19Fu-FA with Ectopic Expression of ufaC (RSP1091) and cfaO (RSP1090).

The ability to enhance production of 19Fu-FA by ectopically expressing ufaC (RSP1091) and cfaO (RSP1090) was assessed. A plasmid expressing ufaC and cfaO from an IPTG-inducible promoter was introduced into ΔchrR/ΔufaC R. sphaeroides cells. In the absence of IPTG, these cells showed the production of 19Fu-FA and a decrease in the abundance of M-UFA relative to the amounts in ΔchrR/ΔufaC cells (FIG. 12, panels A and B). These changes were presumably a result of leaky expression of ufaC and cfaO gene products in the absence of inducer. Induction of ufaC and cfaO expression with IPTG resulted in an increase in 19Fu-FA production and a further decrease in M-UFA abundance relative to the uninduced cells (FIG. 12, panels B and C). These results show that ectopic expression of ufaC and/or cfaO can increase production of fatty acids such as 19Fu-FA and that this increase can be modulated by the amount of expression.

$O_2$ is Needed for Accumulation of 19Fu-FA.

$O_2$ is one potential source of the oxygen moiety in Fu-FAs (Spiteller 2005), but experimental evidence in support of this notion is lacking. To test if $O_2$ was needed for accumulation of this bacterial 19Fu-FA, the FAME profile of cells containing increased $\sigma^E$ activity (ΔChrR cells) grown aerobically (30% $O_2$ in the dark) was compared with those grown anaerobically (in the light by photosynthesis). Analysis of the FAME profile shows that 19Fu-FA is only detected when cells were grown in the presence of $O_2$. By contrast, it was found that 19M-UFA accumulated when this strain was grown both in the presence and absence of $O_2$, suggesting that RSP2144 activity does not require $O_2$ (Table 3). It was concluded that $O_2$ acts as a source of oxygen in this bacterial 19Fu-FA.

$^1O_2$ Causes Turnover of 19Fu-FA.

The above experiments showed accumulation of 19M-UFA and 19Fu-FA in ΔChrR cells that have increased $\sigma^E$ activity. It was determined whether changes in fatty acid content were observed when wild type cells were exposed to $^1O_2$, a signal that induces $\sigma^E$ activity (Ziegelhoffer et al. 2009, Anthony et al. 2004, Nam et al. 2013). When wild type cells were exposed to $^1O_2$ as a way to increase $\sigma^E$ activity (Ziegelhoffer et al. 2009, Anthony et al. 2004, Nam et al. 2013), there was no detectable accumulation of 19Fu-FA. This result was somewhat surprising because the conditions used to produce $^1O_2$ are known to be sufficient to increase $\sigma^E$ activity (Anthony et al. 2004, Nam et al. 2013), so accumulation of 19Fu-FA was expected.

$^1O_2$ can directly oxidize furan moieties and produce fatty acyl radicals from unsaturated fatty acids, so it has been proposed that Fu-FAs can act as a scavenger for this and other ROS (Okada et al. 1996, Okada et al. 1990, White et al. 2005, Wakimoto et al. 2011). Thus, the failure to observe alterations of the fatty acid content when wild type cells were exposed to $^1O_2$ could reflect the ability of 19Fu-FA to scavenge this ROS or products of its action on bilayer constituents. To test this hypothesis, the effect of $^1O_2$ on the fatty acid content of ΔChrR cells was determined (Table 3). $^1O_2$ was generated by adding methylene blue (MB) to aerobically grown cultures in the presence of light. A time-dependent decrease in the abundance of 19Fu-FA was observed after exposing aerobically grown ΔChrR cells to methylene blue in light. (FIG. 13, squares). This decrease in abundance of 19Fu-FA was not observed in an aerobically grown ΔChrR control culture that was exposed to methylene blue in the dark (FIG. 13, circles) or when aerobically grown cells were transferred to dark, anaerobic conditions at time 0 (FIG. 13, triangles). Thus, it was concluded that this observed decrease in 19Fu-FA abundance required conditions that result in $^1O_2$ formation. One explanation for this observation is that 19Fu-FA acts as a scavenger of fatty acyl radicals or other compounds that are produced in the presence of $^1O_2$ (see Discussion).

$^1O_2$ Causes Turnover of 19Fu-FA In Vitro.

The ability of 19Fu-FA to scavenge $^1O_2$ was tested in vitro. A number of fatty acids, including C18:1, C18:0, M-UFA, 19Fu-FA, and C19:0 were incubated in a test tube with (FIG. 14B) or without (FIG. 14A) $^1O_2$. The $^1O_2$ was generated with exposure methylene blue exposure in the light (FIG. 14B). Methylene blue exposure in the dark was used as a negative control (FIG. 14A). $^1O_2$ caused degradation of 19Fu-FA but not the other fatty acids (note absence of 19Fu-FA peak in FIG. 14B). Degradation of 19Fu-FA was detectable as early as 2 minutes after exposure to $^1O_2$ and was completely degraded by 30 minutes. These data show the ability of 19Fu-FA to directly scavenge reactive oxygen species such as $^1O_2$.

Production of 19M-UFA or 19Fu-FA in *Rhodopseudomonas palustris*.

19M-UFA and 19Fu-FA were found among fatty acids isolated from *R. palustris* (FIG. 15). This result suggests that the production of fatty acids such as 19M-UFA, Ce-FA, and 19Fu-FA in *R. palustris* can be increased by expressing or increasing expression of RSP2144, RSP1091, and/or RSP1090 or homologs thereof in *R. palustris*. This result also suggests that the production of fatty acids such as 19M-UFA, Ce-FA, and 19Fu-FA in other microorganisms can be increased by expressing or increasing expression of RSP2144, RSP1091, and/or RSP1090 or homologs thereof in such organisms. Selective production of 19M-UFA or Ce-FA can occur through increasing expression of a subset of these genes in combination with decreasing expression of or deleting others.

Discussion

The above examples demonstrate the accumulation of branched-chain, cyclic, and furan-containing fatty acids in *R. sphaeroides* and show that a newly-identified class of a SAM-dependent methylase (RSP2144, UfaM), uncharacterized protein RSP1091 (UfaC), and uncharacterized protein RSP1090 (CfaO), respectively, are responsible for their production. The data indicate that 19M-UFA, Ce-FA, and 19Fu-FA are synthesized from unsaturated fatty acids in cellular phospholipids using a previously uncharacterized set of enzymes (FIG. 16). Furthermore, the data show that formation of the ROS $^1O_2$ leads to loss of 19Fu-FA, suggesting that this fatty acyl chain acts to scavenge reactive and potentially damaging products present in the bilayer upon $^1O_2$ formation. We further demonstrate the production of 19M-UFA and 19Fu-FA in a second bacterium, *R. palustris*, indicating that recombinant strains that over-produce one or more of these or other novel fatty acids can be generated.

Identification of Gene Products Needed to Produce 19M-UFA, Ce-FA, and 19Fu-FA.

19M-UFA and 19Fu-FA were identified as unknown fatty acids present in a mutant strain (ΔChrR) of the photosynthetic bacterium *R. sphaeroides*. This mutant strain constitutively expresses stress response genes, such as RSP2144 and RSP1091, shown previously to be required for survival in the presence of $^1O_2$ (Ziegelhoffer et al. 2009, Anthony et al. 2004, Nam et al. 2013). The data show that RSP2144 is a SAM-dependent methylase that synthesizes M-UFA, both in vitro when a recombinant protein is incubated with purified native phospholipids, and in vivo when expressed in *R. sphaeroides* or heterologously expressed in *E. coli*.

RSP2144 was previously annotated as a cyclopropane fatty acyl synthase. However it does not produce detectable levels of cyclopropane fatty acids (CFAs) in vivo or in vitro under any conditions tested. Instead, the data indicate that RSP2144 is a previously undescribed enzyme that produces a 19-carbon methylated unsaturated fatty acid (UFA) product, hence the name UfaM. In addition, UfaM could have a preference for methylating vaccenic acid (C18:1), since only a C19 methyl product was observed when this protein was expressed in *E. coli* (which contains more C16:1 than C18:1 fatty acyl chains). In addition, the production of the trans isomer of 19M-UFA from cis-vaccenic acid predicts that SAM-dependent fatty acyl methylation by UfaM uses a reaction mechanism similar to methylases involved in mycolic acid biosynthesis (Grogan et al. 1997, Yuan et al. 1997).

The examples also demonstrate that other $\sigma^E$ target genes, RSP1091 and RSP1090 (Ziegelhoffer et al. 2009, Anthony et al. 2004, Dufour et al. 2008), are needed for conversion of 19M-UFA to 19Fu-FA (FIG. 16). The data show that this conversion results from growth of cells under aerobic conditions, suggesting that $O_2$ is the source of the oxygen moiety in the furan ring. RSP1091 is annotated as a protein of unknown function (Ziegelhoffer et al. 2009, Anthony et al. 2004, Dufour et al. 2008), but it is predicted to contain an N-terminal Rossman fold (putative pyridine nucleotide binding domain), a flavin binding domain, and to be a fatty acyl modifying enzyme (Kontur et al. 2012, Mackenzie et al. 2001). RSP1091 and RSP1090 were previously uncharacterized (Anthony et al. 2004, Dufour et al. 2008, Kontur et al. 2012), but the data provided herein suggest these enzymes permit conversion of 19M-UFA into 19Fu-FA via Ce-FA in an $O_2$-dependent manner, likely with the use of flavin and pyridine nucleotide cofactors. It is possible that other proteins in the putative RSP1091-1087 operon also participate in the conversion of 19M-UFA into 19Fu-FA. The data show that synthesis of 19Fu-FA requires the ability of cells to make 19M-UFA and Ce-FA, as the loss of any one or more of UfaM (RSP2144), UfaC (RSP1091), and CfaO (RSP1090) prevents synthesis of 19Fu-FA. In this regard, it appears that methylation of the unsaturated fatty acid creates a tertiary carbon in the acyl chain that is needed for subsequent conversion of 19M-UFA to 19Fu-FA via Ce-FA.

Protective Role of 19Fu-FA in Scavenging ROS-Mediated Damage.

The examples show that the conditions which lead to formation of $^1O_2$ also result in turnover of 19Fu-FA in vivo. Under the conditions used, ~50% of 19Fu-FA is removed in one cell doubling (~3 hours for *R. sphaeroides*). This is probably an underestimate of the turnover of this fatty acid in the presence of $^1O_2$ since these cells are also capable of synthesizing new 19Fu-FA under these conditions. In addition, it is unclear precisely how much $^1O_2$ is formed inside or outside the cells under the conditions used. Thus, it is possible that the reactivity of 19Fu-FA is underestimated since fatty acyl chains in the inner or outer membrane of this gram-negative bacterium are in the immediate vicinity of $^1O_2$.

From the chemical properties of Fu-FAs, it is proposed that they can scavenge lipid peroxides, fatty acyl radicals, or even $^1O_2$ (Spiteller 2005, Okada et al. 1996, Okada et al. 1990). The loss of 19Fu-FA when cells generate $^1O_2$ is the first report of their potential role as scavengers of ROS in bacteria. Wild type *R. sphaeroides* retains viability and grows after formation of $^1O_2$ (Anthony, 2005), and carotenoids have typically been considered as the major route for quenching this ROS in photosynthetic bacteria and other microbes (Armstrong 1996, Cogdell 2000, Krinsky 1989). Previous studies have shown that $^1O_2$ kills cells lacking either UfaM (RSP2144) or RSP1091 (Nam et al. 2013, Nuss et al. 2013). It is now known from the present examples that both of these strains are unable to make 19Fu-FA. Combined, these observations indicate that synthesis of 19Fu-FA is required for viability in the presence of $^1O_2$, possibly because they can also scavenge and minimize cellular damage by this ROS.

Potential Role of 19Fu-FA as a Bacterial Second Messenger.

It is not surprising that previous analysis of the fatty acid content of wild type cells did not detect the presence of 19Fu-FA (Donohue et al. 1982, Hands et al. 1962, Qureshi et al. 1988, Russell et al. 1979). Transcription of the genes needed to synthesize 19Fu-FA requires high activity of the alternative sigma factor $\sigma^E$, but, in the absence of $^1O_2$, $\sigma^E$ activity is inhibited because it is bound to an anti-sigma factor ChrR (Ziegelhoffer et al. 2009, Anthony et al. 2005, Anthony et al. 2004). The examples show that $^1O_2$ formation leads to 19Fu-FA turnover in ΔChrR cells, explaining why one does not observe time-dependent changes in levels of 19Fu-FA after exposing wild-type cells to $^1O_2$.

In contrast to the situation in wild type cells, mutants lacking either UfaM or RSP1091 have defects in increasing $\sigma^E$ transcriptional activity (Nam et al. 2013, Nuss et al. 2013). This observation and the results of the experiments in the examples suggest that a product of either gene is needed to promote dissociation of a $\sigma^E$-ChrR complex (Nam et al. 2013). For example, the ability of 19Fu-FA to scavenge $^1O_2$ could lead to accumulation of lipid peroxides that act as a second messenger to promote dissociation of the $\sigma^E$-ChrR complex. In this model, the subsequent ChrR proteolysis in the presence of $^1O_2$ (Nam et al. 2013, Nuss et al. 2013, Greenwell et al. 2011) could be promoted by direct modification of this anti-sigma factor or by the activation of one or more proteases by a lipid peroxide.

ufaM (RSP2144) and the genes in the RSP1091-1087 operon are present across a wide group of α- and γ-proteobacteria (Ziegelhoffer et al. 2009, Dufour et al. 2008) (FIGS. 17A and 17B). In addition, in these other organisms, homologs of these genes are predicted to be transcribed by a homolog of *R. sphaeroides* $\sigma^E$, suggesting they are members of a core regulon that is conserved across the bacterial phylogeny (Dufour et al. 2008) (FIGS. 17A and 17B). Thus, it would appear that 19Fu-FA synthesis in the presence of $^1O_2$ and the potential use of the products of UfaM and RSP1091 as second messengers is conserved across bacteria. Accordingly, bacterial synthesis of 19M-UFA, Ce-FA, and/or 19Fu-FA can be produced or increased in all bacteria by increasing the expression of UfaM, RSP1091, RSP1090, or homologs thereof. This is evidenced in the above examples with the production of 19Fu-FA and 19M-UFA with UfaM and RSP1091 in such diverse bacteria as α-proteobacteria (*R. sphaeroides*) and γ-proteobacteria (*E. coli*).

Conditions and enzymes needed for bacterial synthesis of 19Fu-FA are identified in the examples. Compounds predicted to be 19Fu-FA and 19M-UFA were provisionally identified in bacteria before (Shirasaka et al. 1995, Shirasaka et al. 1997), but their chemical identity was not absolutely confirmed and information on their cellular abundance, the enzymes needed for their synthesis, and their cellular role were not reported. Conditions that increase production of 19Fu-FA in both native and foreign hosts, such as *E. coli*, are also identified in the examples. The examples provide methods for synthesizing large quantities of 19M-UFA, Ce-FA, and/or 19Fu-FA in bacterial systems. With large amounts of 19Fu-FA available, one can probe the interaction of $^1O_2$ with this Fu-FA, identify potential secondary messengers, and test the utility of Fu-FAs as food, chemical, or fuel additives.

CITED REFERENCES

Anthony J R, Warczak K L, & Donohue T J (2005) A transcriptional response to singlet oxygen, a toxic byproduct of photosynthesis. *Proc Natl Acad Sci USA* 102(18): 6502-6507.

Anthony J R, Newman J D, & Donohue T J (2004) Interactions between the *Rhodobacter sphaeroides* ECF sigma factor, $\sigma^E$, and its anti-sigma factor, ChrR. *J. Mol. Biol.* 341:345-360.

Armstrong G & Hearst J (1996) Carotenoids 2: Genetics and molecular biology of carotenoid pigment biosynthesis. The *FASEB Journal* 10(2):228-237.

Baba T, et al. (2006) Construction of *Escherichia coli* K-12 in-frame, single-gene knockout mutants: the Keio collection. *Molecular systems biology* 2:2006 0008.

Batna, A.; Spiteller, G. Oxidation of Furan-containing fatty acids by Soybean Lipoxygenase-1 in the Presence of Linoleic Acid. Chem. Phys. Lipids, 1994, 70, 179-185.

Bethesda-Research-Laboratories (1986) BRL pUC host: *Escherichia coli* DH5α competent cells. *Bethesda Research Laboratories Focus* 8:9-10.

Christie W (2010) Lipid Analysis. ed P. J. Barnes & Associates (Eds.) (The Oily Press, Bridgwater), p 148.

Cogdell R J (2000) How carotenoids protect bacterial photosynthesis. *Phil. Trans. R. Soc. Lond. B* 355:1345-1349.

Connor M R & Liao J C (2009) Microbial production of advanced transportation fuels in non-natural hosts. *Current Opinion in Biotechnology* 20(3):307-315.

Cronan J E (2002) Phospholipid modifications in bacteria. *Curr. Opin. Microbiol.* 5:202-205.

Cronan J E (2003) Bacterial membrane lipids: Where Do We Stand? *Annual Review of* Microbiology 57(1):203-224.

Chang Y Y & Cronan J E, Jr. (1999) Membrane cyclopropane fatty acid content is a major factor in acid resistance of *Escherichia coli*. *Mol Microbiol* 33(2):249-259.

Courtois F, Guerard C, Thomas X, & Ploux O (2004) *Escherichia coli* cyclopropane fatty acid synthase. *European journal of biochemistry/FEBS* 271(23-24):4769-4778.

Donohue T J, Cain B D, & Kaplan S (1982) Purification and characterization of an N-acylphosphatidylserine from *Rhodopseudomonas sphaeroides*. *Biochemistry* 21(11): 2765-2773.

Dufour Y S, Landick R, & Donohue T J (2008) Organization and evolution of the biological response to singlet oxygen stress. *J Mol Biol* 383(3):713-730.

Fuchs, C.; Spiteller, G. Iron Release from the Active Site of Lipoxygenase, Z. Naturforsch. 2000, 55, 643-648

Girotti A W & Kriska T (2004) Role of lipid peroxides in photo-oxidative stress signalling. *Antioxidants & Redox Signalling* 6:301-310.

Glaeser J, Nuss A M, Berghoff B A, & Klug G (2011) Singlet oxygen stress in microorganisms. *Advances in Microbial Physiology*, ed Robert K P (Academic Press), Vol Volume 58, pp 141-173.

Glass, R. L.; Krick, T. P.; Olson, D. L.; Thorson, R. L. The Occurrence and Distribution of Furan-containing fatty acids in Spawning Male Freshwater Fish. Lipids, 1977, 12, 828-836.

Glass, R. L.; Krick, T. P.; Sand, D. M.; Rahn, C. H.; Schlenk, H. Furanoid Fatty Acids from Fish Lipids. Lipids, 1975, 10, 695-702.

Glass, R. L.; Krick, T. P.; Eckhardt, A. E. New Series of Fatty Acids in Northern Pike (Esox Indus). Lipids, 1974, 9, 1004-1008.

Graft, G.; Gellerman, J. L.; Sand, D. M.; Schlenk, H. Inhibition of Blood Platelet Aggregation by Dioxo-ene Compounds. Biochim. Biophys. Acta, 1984, 799, 143-150.

Greenwell R S, Nam T W, & Donohue T J (2011) Aspects of the zinc metalloprotein ChrR required for dissociation of $\sigma^E$/ChrR complexes. *Journal of Molecular Biology* 407:477-491.

Grogan D W & Cronan J E (1997) Cyclopropane ring formation in membrane lipids of bacteria. Microbiology and Molecular Biology Reviews 61(4):429-441.

Guianvarc'h D, Drujon T, Leang T E, Courtois F, & Ploux O (2006) Identification of new inhibitors of *E. coli* cyclopropane fatty acid synthase using a colorimetric assay. *Biochimica et Biophysica Acta (BBA)—Proteins and Proteomics* 1764(8):1381-1388.

Gunstone, F. D.; Wijesundera, R. C.; Scrimgeour, C. M. The Component Acids of Lipids from Marine and Freshwater Species with Special Reference to Furan-Containing Acids. J. Sci. Food Agric. 1978, 29, 539-550.

Halliwell, B.; Gutteridge, J. M. C. Role of Free Radicals and Catalytic Metal Ions in Human Disease: An Overview, Methods Enzymol. 1990, 186, 1-85.

Hands A R & Bartley W (1962) The fatty acids of Rhodopseudomonas particles. *The Biochemical journal* 84:238

Hannemann, K.; Puchta, V.; Simon, E.; Ziegler, H.; Ziegler, G.; Spiteller, G. The Common Occurrence of Furan-containing fatty acids in Plants. Lipids, 1989, 24, 296-298.

Imlay J A (2003) Pathways of oxidative damage. *Annu. Rev. Microbiol.* 57:395-418.

Ishii, K.; Okajima, H.; Okada, Y.; Watanabe, H. Studies on Furan-containing fatty acids of Salmon Roe Phospholipids. J. Biochem. (Tokyo), 1988, 103, 836-839.

Ishii, K.; Okajima, H.; Okada, Y.; Watanabe, H. Effects of Phosphatidylcholines Containing Furan-containing fatty acid on Oxidation in Multilamellar Liposomes. Chem. Pharm. Bull. 1989, 37, 1396-1398.

Iwig D F, Uchida A, Stromberg J A, & Booker S J (2005) The activity of *Escherichia coli* cyclopropane fatty acid synthase depends on the presence of bicarbonate. *Journal of the American Chemical Society* 127(33): 11612-11613.

Jandke, J.; Schmidt, J.; Spiteller G. Über das Verhalten von F-Sauren bei der Oxidation mit Lipoxydase in Anwesenheit von S H-haltigen Verbindungen, liebigs Ann. Chem. 1988, 29-34.

Kontur W S, et al. (2012) Revised sequence and annotation of the *Rhodobacter sphaeroides* 2.4.1 genome. *Journal of Bacteriology* 194:7016-7017.

Koopman W J, et al. (2010) Mammalian mitochondrial complex I: biogenesis, regulation, and reactive oxygen species generation. *Antioxid Redox Signal* 12(12):1431-1470.

Krinsky N I (1989) Antioxidant functions of carotenoids. *Free radical biology & medicine* 7(6):617-635.

Lands B (2012) Consequences of Essential Fatty Acids. Nutrients 4(9):1338-1357.

Lemke R A, Peterson A C, Ziegelhoffer E C, Westphall M S, Tjellström H, Coon J J, Donohue T J. Synthesis and scavenging role of furan fatty acids. *Proc Natl Acad Sci USA*. 2014 Aug. 19; 111(33):E3450-7.

Lennen R M, Braden D J, West R A, Dumesic J A, & Pfleger B F (2010) A process for microbial hydrocarbon synthesis: Overproduction of fatty acids in *Escherichia coli* and catalytic conversion to alkanes. *Biotechnol Bioeng* 106(2):193-202.

Mackenzie C, et al. (2001) The home stretch, a first analysis of the nearly completed genome of *Rhodobacter sphaeroides* 2.4.1. *Photosynth Res* 70(1):19-41.

Magnuson K, Jackowski S, Rock C O, & Cronan J E (1993) Regulation of fatty acid biosynthesis in *Escherichia coli*. Microbiological Reviews 57(3):522-542.

Michaud A L, Diau G-Y, Abril R, & Brenna J T (2002) Double bond localization in minor homoallylic fatty acid methyl esters using acetonitrile chemical ionization tandem mass spectrometry. *Analytical Biochemistry* 307(2): 348-360.

Montanari C, Sado Kamdem S L, Serrazanetti D I, Etoa F X, & Guerzoni M E (2010) Synthesis of cyclopropane fatty acids in *Lactobacillus helveticus* and *Lactobacillus sanfranciscensis* and their cellular fatty acids changes following short term acid and cold stresses. *Food microbiology* 27(4):493-502.

Morris, L. J.; Marshall, M. O.; Kelly, W. A Unique Furanoid Fatty Acid from Exocarpus seed oil. Tetrahedron Lett. 1966, 16, 4249-4253.

Mueller S, et al. (2008) General detoxification and stress responses are mediated by oxidized lipids through TGA transcription factors in *Arabidopsis*. *Plant Cell* 20(3):768-785.

Nam T W, Ziegelhoffer E C, Lemke R A S, & Donohue T J (2013) Proteins needed to activate a transcriptional response to the reactive oxygen species singlet oxygen. *mBio* 4(1):e00541-00512.

Newman J D, Falkowski M J, Schilke B A, Anthony L C, & Donohue T J (1999) The *Rhodobacter sphaeroides* ECF sigma factor, $\sigma^E$, and the target promoters cycA P3 and rpoE P1. *J Mol Biol* 294(2):307-320.

Nuss A M, et al. (2013) DegS and RseP homologous proteases are involved in singlet oxygen dependent activation of RpoE in *Rhodobacter sphaeroides*. *PLoS ONE* 8(11):e79520.

Okada Y, Kaneko M, & Okajima H (1996) Hydroxyl radical scavenging activity of naturally occurring furan-containing fatty acids. *Biological & pharmaceutical bulletin* 19(12):1607-1610.

Okada Y, Okajima H, & Konishi H (1990) Antioxidant effect of naturally occurring furan-containing fatty acids on oxidation of linoleic acid in aqueous dispersion. *Journal of the American Oil Chemists' Society (JAOCS)* 67:858-862.

Olins P O, Rangwala S H. A novel sequence element derived from bacteriophage T7 mRNA acts as an enhancer of translation of the lacZ gene in *Escherichia coli*. *J Biol Chem*. 1989 Oct. 15; 264(29):16973-6.

Ota, T.; Takagi, T. Furan-containing fatty acids in the Lipids of the Cresthead Flounder. *Nippon Suisan Gakkaishi*, 1992, 58, 721-725.

Peralta-Yahya P P, Zhang F, del Cardayre S B, & Keasling J D (2012) Microbial engineering for the production of advanced biofuels. *Nature* 488(7411):320-328.

Peterson A C, et al. (2014) Development of a GC/Quadrupole-Orbitrap mass spectrometer, Part I: Design and characterization. *Analytical Chemistry* (Submitted).

Peterson A C, et al. (2014) Development of a G C/Quadruple-Orbitrap mass spectrometer, Part II: New approaches for discovery metabolomics. *Analytical Chemistry* (Submitted).

Qureshi N, Honovich J P, Hara H, Cotter R J, & Takayama K (1988) Location of fatty acids in lipid A obtained from lipopolysaccharide of *Rhodopseudomonas sphaeroides* ATCC 17023. *J Biol Chem* 263(12):5502-5504.

Rothamer D A, Donohue T J. Chemistry and combustion of fit-for-purpose biofuels. *Curr Opin Chem Biol*. 2013 June; 17(3):522-8.

Rouser G, Fkeischer S, & Yamamoto A (1970) Two dimensional then layer chromatographic separation of polar lipids and determination of phospholipids by phosphorus analysis of spots. *Lipids* 5(5):494-496.

Russell N J & Harwood J L (1979) Changes in the acyl lipid composition of photosynthetic bacteria grown under photosynthetic and non-photosynthetic conditions. *The Biochemical journal* 181(2):339-345.

Sayre L M, De L, Quan Y, Xiaochun Z, & Xiaoxia T (2006) Protein adducts generated from products of lipid oxidation: Focus on HNE and ONE*. *Drug Metabolism Reviews* 38(4):651-675.

Schilke B A & Donohue T J (1995) ChrR positively regulates transcription of the *Rhodobacter sphaeroides* cytochrome $c_2$ gene. *Journal of Bacteriology* 177(8): 1929-1937.

Schödel, R.; Spiteller, G. Uber die Strukturaufklärung von (Hydroxy-oxo-cyclopentenyl) alkansauren, den Aldolkondensationsprodukten von Dioxoen carbonsäuren aus Rinderleber. *Helv. Chim. Acta*, 1985, 68, 1624-1634.

Shirasaka N, Nishi K, & Shimizu M (1995) Occurrence of a furan-containing fatty acid in marine bacteria. *Biochim Biophys Acta.* 1258(3):225-227.

Shirasaka N, Nishi K, & Shimizu S (1997) Biosynthesis of furan-containing fatty acids (F-acids) by a marine bacterium, *Shewanella putrefaciens. Biochimica et biophysica acta* 1346(3):253-260.

Simon R, Priefer U, & Puhler A (1983) A broad host range mobilization system for in vitro genetic engineering: transposon mutagenesis in Gram negative bacteria. *Bio/technology* 1:748-791.

Spiteller G (2005) Furan-containing fatty acids: occurrence, synthesis, and reactions. Are furan-containing fatty acids responsible for the cardioprotective effects of a fish diet? *Lipids* 40(8):755-771.

Tjellström H, Strawsine M, Silva J, Cahoon E B, & Ohlrogge J B (2013) Disruption of plastid acyl:acyl carrier protein synthetases increases medium chain fatty acid accumulation in seeds of transgenic *Arabidopsis. FEBS Letters* 587(7):936-942.

Wakimoto T, et al. (2011) Furan-containing fatty acid as an anti-inflammatory component from the green-lipped mussel *Perna canaliculus. Proceedings of the National Academy of Sciences* 108(42):17533-17537.

Wang A Y, Grogan D W, & Cronan J E (1992) Cyclopropane fatty acid synthase of *Escherichia coli*: Deduced amino acid sequence, purification, and studies of the enzyme active site. *Biochemistry* 31(45):11020-11028.

Watabe N, Ishida Y, Ochiai A, Tokuoka Y, & Kawashima N (2007) Oxidation decomposition of unsaturated fatty acids by singlet oxygen in phospholipid bilayer membranes. *Journal of Oleo Science* 56(2):73-80.

White D C, et al. (2005) Phospholipid furan-containing fatty acids and ubiquinone-8: lipid biomarkers that may protect dehalococcoides strains from free radicals. *Applied and environmental microbiology* 71(12):8426-8433.

Yuan Y, Crane D C, Musser J M, Sreevatsan S, & Barry C E (1997) MMAS-1, the Branch Point Between cis- and trans-Cyclopropane-containing Oxygenated Mycolates in *Mycobacterium tuberculosis. J Biol Chem* 272(15): 10041-10049.

Ziegelhoffer E C & Donohue T J (2009) Bacterial responses to photo-oxidative stress. *Nat Rev Microbiol* 7(12):856-863.

We claim:

1. A microorganism modified with respect to a native microorganism, the microorganism comprising one or more genes encoding
    an RSP2144 enzyme or homolog thereof, wherein the RSP2144 enzyme or homolog thereof comprises an amino acid sequence having at least 85% sequence identity to the amino acid sequence of SEQ ID NO: 2 or SEQ ID NO: 15; and
    an RSP1090 enzyme or homolog thereof, wherein the RSP1090 enzyme or homolog thereof comprises an amino acid sequence having at least 85% sequence identity to the amino acid sequence of SEQ ID NO: 6 or SEQ ID NO: 17,
    wherein each of the one or more genes comprises a non-native nucleic acid sequence.

2. The microorganism of claim 1, wherein expression of the RSP1090 enzyme or homolog thereof is increased in the microorganism compared to the native microorganism.

3. The microorganism of claim 1, wherein the one or more genes further encode an RSP1091 enzyme or homolog thereof, wherein the RSP1091 enzyme or homolog thereof comprises an amino acid sequence having at least 85% sequence identity to the amino acid sequence of SEQ ID NO:4 or SEQ ID NO: 16.

4. The microorganism of claim 3, wherein expression of the RSP1091 enzyme or homolog thereof is increased in the microorganism compared to the native microorganism.

5. The microorganism of claim 1, wherein the microorganism produces an increased amount of a furan-containing fatty acid compared to the native microorganism.

6. The microorganism of claim 1, wherein each of the one or more genes comprises a coding sequence operably linked to a heterologous promoter.

7. The microorganism of claim 1, wherein the microorganism comprises a deletion of an endogenous ChrR gene or bacterial homolog thereof.

8. The microorganism of claim 1, wherein:
    the amino acid sequence of the RSP2144 enzyme or homolog thereof has at least 90% sequence identity to the amino acid sequence of SEQ ID NO: 2 or SEQ ID NO: 15; and
    the amino acid sequence of the RSP1090 enzyme or homolog thereof has at least 90% sequence identity to the amino acid sequence of to SEQ ID NO: 6 or SEQ ID NO: 17.

9. The microorganism of claim 8, wherein expression of the RSP1090 enzyme or homolog thereof is increased in the microorganism compared to the native microorganism.

10. The microorganism of claim 8, wherein the one or more genes further encode an RSP1091 enzyme or homolog thereof, wherein the RSP1091 enzyme or homolog thereof comprises an amino acid sequence having at least 90% sequence identity to the amino acid sequence of SEQ ID NO:4 or SEQ ID NO: 16.

11. The microorganism of claim 10, wherein expression of the RSP1091 enzyme or homolog thereof is increased in the microorganism compared to the native microorganism.

12. The microorganism of claim 8, wherein the microorganism produces an increased amount of a furan-containing fatty acid compared to the native microorganism.

13. The microorganism of claim 8, wherein each of the one or more genes comprises a coding sequence operably linked to a heterologous promoter.

14. A method of producing a fatty acid comprising:
    culturing the modified microorganism of claim 1 to produce a fatty acid; and
    isolating the fatty acid.

15. A microorganism modified with respect to a native microorganism, the microorganism comprising:
    a gene encoding an RSP2144 enzyme or homolog thereof, wherein the RSP2144 enzyme or homolog thereof comprises an amino acid sequence having at least 85% sequence identity to the amino acid sequence of SEQ ID NO: 2 or SEQ ID NO: 15, wherein the gene comprises a non-native nucleic acid sequence,
    wherein the microorganism has reduced or ablated expression compared to the native microorganism of at least one of:
        a native RSP1091 enzyme or native homolog thereof, wherein the native RSP1091 enzyme or native homolog thereof comprises an amino acid sequence having at least 85% sequence identity to the amino acid sequence of SEQ ID NO: 4 or SEQ ID NO: 16; and
        a native RSP1090 enzyme or native homolog thereof, wherein the native RSP1090 enzyme or native homolog thereof comprises an amino acid sequence having at least 85% sequence identity to the amino acid sequence of SEQ ID NO: 6 or SEQ ID NO: 17,
    wherein the microorganism exhibits at least one of increased enzyme activity of the RSP2144 enzyme or homolog thereof, decreased enzyme activity of the RSP1091 enzyme or homolog thereof, and decreased enzyme activity of the RSP1090 enzyme or homolog thereof compared to the native microorganism.

16. The microorganism of claim 15, wherein the gene encoding the RSP2144 enzyme or homolog thereof comprises a coding sequence operably linked to a heterologous promoter.

17. The microorganism of claim 15, wherein the microorganism further comprises a gene encoding an RSP1091 enzyme or homolog thereof, wherein the RSP1091 enzyme or homolog thereof comprises an amino acid sequence having at least 85% sequence identity to the amino acid sequence of SEQ ID NO:4 or SEQ ID NO: 16, wherein the gene encoding the RSP1091 enzyme or homolog thereof comprises a non-native nucleic acid sequence.

18. The microorganism of claim 15, wherein:
    the RSP2144 enzyme or homolog thereof comprises an amino acid sequence having at least 90% sequence identity to the amino acid sequence of SEQ ID NO: 2 or SEQ ID NO: 15;
    the native RSP1091 enzyme or native homolog thereof comprises an amino acid sequence having at least 90% sequence identity to the amino acid sequence of SEQ ID NO:4 or SEQ ID NO: 16; and
    the native RSP1090 or native homolog thereof comprises an amino acid sequence having at least 90% sequence identity to the amino acid sequence of SEQ ID NO:6 or SEQ ID NO: 17.

19. The microorganism of claim 18, wherein the gene encoding the RSP2144 enzyme or homolog thereof comprises a coding sequence operably linked to a heterologous promoter.

20. The microorganism of claim 18, wherein the microorganism further comprises a gene encoding an RSP1091 enzyme or homolog thereof, wherein the RSP1091 enzyme or homolog thereof comprises an amino acid sequence having at least 90% sequence identity to the amino acid sequence of SEQ ID NO:4 or SEQ ID NO: 16, wherein the gene encoding the RSP1091 enzyme or homolog thereof comprises a non-native nucleic acid sequence.

21. A method of producing a fatty acid comprising:
culturing the modified microorganism of claim 15 to produce a fatty acid; and
isolating the fatty acid.

22. The microorganism of claim 15, wherein the microorganism exhibits increased enzyme activity of the RSP2144 enzyme or homolog thereof and at least one of decreased enzyme activity of the RSP1091 enzyme or homolog thereof and decreased enzyme activity of the RSP1090 enzyme or homolog thereof compared to the native microorganism.

23. The microorganism of claim 15, wherein the microorganism exhibits increased enzyme activity of the RSP2144 enzyme or homolog thereof, decreased enzyme activity of the RSP1091 enzyme or homolog thereof, and decreased enzyme activity of the RSP1090 enzyme or homolog thereof compared to the native microorganism.

24. A microorganism modified with respect to a native microorganism, the microorganism comprising:
a gene encoding an RSP2144 enzyme or homolog thereof, wherein the RSP2144 enzyme or homolog thereof comprises an amino acid sequence having at least 85% sequence identity to the amino acid sequence of SEQ ID NO: 2 or SEQ ID NO: 15, wherein the gene comprises a non-native nucleic acid sequence,
wherein the microorganism has reduced or ablated expression of a native RSP1090 enzyme or native homolog thereof compared to the native microorganism, wherein the native RSP1090 enzyme or native homolog thereof comprises an amino acid sequence having at least 85% sequence identity to the amino acid sequence of SEQ ID NO: 6 or SEQ ID NO: 17.

25. The microorganism of claim 24, wherein the gene encoding the RSP2144 enzyme or homolog thereof comprises a coding sequence operably linked to a heterologous promoter.

26. The microorganism of claim 24, wherein the microorganism further comprises a gene encoding an RSP1091 enzyme or homolog thereof, wherein the RSP1091 enzyme or homolog thereof comprises an amino acid sequence having at least 85% sequence identity to the amino acid sequence of SEQ ID NO:4 or SEQ ID NO: 16, wherein the gene encoding the RSP1091 enzyme or homolog thereof comprises a non-native nucleic acid sequence.

27. The microorganism of claim 24, wherein:
the RSP2144 enzyme or homolog thereof comprises an amino acid sequence having at least 90% sequence identity to the amino acid sequence of SEQ ID NO: 2 or SEQ ID NO: 15; and
the native RSP1090 or native homolog thereof comprises an amino acid sequence having at least 90% sequence identity to the amino acid sequence of SEQ ID NO:6 or SEQ ID NO: 17.

28. The microorganism of claim 27, wherein the gene encoding the RSP2144 enzyme or homolog thereof comprises a coding sequence operably linked to a heterologous promoter.

29. The microorganism of claim 27, wherein the microorganism further comprises a gene encoding an RSP1091 enzyme or homolog thereof, wherein the RSP1091 enzyme or homolog thereof comprises an amino acid sequence having at least 90% sequence identity to the amino acid sequence of SEQ ID NO:4 or SEQ ID NO: 16, wherein the gene encoding the RSP1091 enzyme or homolog thereof comprises a non-native nucleic acid sequence.

30. The microorganism of claim 24, wherein the microorganism exhibits decreased enzyme activity of the RSP1090 enzyme or homolog thereof compared to the native microorganism.

31. A method of producing a fatty acid comprising:
culturing the modified microorganism of claim 24 to produce a fatty acid; and
isolating the fatty acid.

32. The microorganism of claim 1, wherein the microorganism comprises at least one of:
a deletion of an endogenous ChrR gene or bacterial homolog thereof;
a recombinant nucleic acid encoding a variant $\sigma^E$ protein, wherein the variant $\sigma^E$ protein comprises an amino acid sequence having at least 85% sequence identity to the amino acid sequence of SEQ ID NO: 14, and at least a mutation selected from the group consisting of K38E, K38R, and M42A, wherein the ability of the variant $\sigma^E$ protein to bind to a ChrR protein is disrupted; and
a recombinant nucleic acid encoding a variant ChrR protein, wherein the variant ChrR protein comprises an amino acid sequence having at least 85% sequence identity to the amino acid sequence of SEQ ID NO: 13, and at least a mutation selected from the group consisting of H6A, H31A, C35A, C35S, C38A, C38S, C38R and C187S/C189S, wherein the ability of the variant ChrR protein to bind to a $\sigma^E$ protein is disrupted.

33. The microorganism of claim 15, wherein the microorganism comprises at least one of:
a mutation in or deletion of a native gene encoding the native RSP1091 enzyme or native homolog thereof, wherein the mutation in or deletion of the native gene encoding the native RSP1091 enzyme or native homolog thereof results in the reduced or ablated expression of the native RSP1091 enzyme or native homolog thereof; and
a mutation in or deletion of a native gene encoding the native RSP1090 enzyme or native homolog thereof, wherein the mutation in or deletion of the native gene encoding the native RSP1090 enzyme or native homolog thereof results in the reduced or ablated expression of the native RSP1090 enzyme or native homolog thereof.

34. The microorganism of claim 24, wherein the microorganism comprises a mutation in or deletion of a native gene encoding the native RSP1090 enzyme or native homolog thereof, wherein the mutation in or deletion of the native gene encoding the native RSP1090 enzyme or native homolog thereof results in the reduced or ablated expression of the native RSP1090 enzyme or native homolog thereof.

* * * * *

SEQUENCE LISTING

<160> NUMBER OF SEQ ID NOS: 18

<210> SEQ ID NO 1
<211> LENGTH: 1212
<212> TYPE: DNA
<213> ORGANISM: Rhodobacter sphaeroides

<400> SEQUENCE: 1

```
atgacggctc tgaccagcac gcgcggccag caggatctgc cgcgctattt ctcgcaggtg      60
ttcgacgtga tgcagggact gcgccacggt cggctcgact tcgtgctcga cgacgggcgg     120
cgcttccggg tcgaggggca ggggccgggg ccggtcgccg aactcgacat tcatgatgcg     180
gatctcttcg cccgtctgat ccgcgagggc gacctcggct tctgcgaggc ctatctcgac     240
ggcggctggt cgacgccgga cctgcaggcc ttcatggatc tgatccatgc cgacaatgac     300
gatgtctatg acggctttcc cggtcagggg ctgctgcgcg cctacgagaa cctgcgccac     360
tggctgcgcg gcaactcgaa gcggcaggcc cgccgcaaca tcgcggccca ttacgacctc     420
ggcaacgact tctacgccct ctggctcgac gagagcatga cctattcctc ggcgctcttc     480
cggaccgggc aggagagcct cgaggaggcg cagcgggcga aatatgccag catggtcgac     540
cggatcggcg cgcagcccgg cgagcatgtg ctggagatcg gctgcggttg gggcggcttc     600
gccgaatatg cggcgcgcga gcggggctg cgggtgacgg gcctcaccat cagccaggcg     660
cagcacgatt atgcggtcga gcggatcgcg cgggcgggcc tgtcggaccg ggtcgagatc     720
cggcttcagg actaccgcga cgagcgggc agcttcgacg gcatcgcctc gatcgagatg     780
ttcgaggcgg tgggcgagaa atactggccg gtctatttcc agaccctgcg cgagcggctg     840
```

```
aagcccgggc gcaatgccac gctgcagatc atcaccgtgc aggacaagag gtgggaggtc    900
taccggcggg gggtggattt cattcagaag tacatcttcc ccggcgggat gctgccctcg    960
cccaccgcgc tccgggtcga ggtggcgaag gcggggctgc atgtaacgga ctcggtcgag   1020
ttcggcgaga gctattccat gacgctgcgc cgctggcacg agaccttcaa cgaccgctgg   1080
gaccgggtgg cggcgctggg cttcgacgag aggttccgcc gcatgtggaa cttctatctc   1140
acctcttgcg caggctcatt cgacggcgga aactgcgacg tgacgcagat caccgtaacg   1200
cgggccgcgt aa                                                       1212
```

<210> SEQ ID NO 2
<211> LENGTH: 403
<212> TYPE: PRT
<213> ORGANISM: Rhodobacter sphaeroides

<400> SEQUENCE: 2

```
Met Thr Ala Leu Thr Ser Thr Arg Gly Gln Gln Asp Leu Pro Arg Tyr
 1               5                  10                  15

Phe Ser Gln Val Phe Asp Val Met Gln Gly Leu Arg His Gly Arg Leu
                20                  25                  30

Asp Phe Val Leu Asp Asp Gly Arg Phe Arg Val Glu Gly Gln Gly
            35                  40                  45

Pro Gly Pro Val Ala Glu Leu Asp Ile His Asp Ala Asp Leu Phe Ala
        50                  55                  60

Arg Leu Ile Arg Glu Gly Asp Leu Gly Phe Cys Glu Ala Tyr Leu Asp
65                  70                  75                  80

Gly Gly Trp Ser Thr Pro Asp Leu Gln Ala Phe Met Asp Leu Ile His
                85                  90                  95

Ala Asp Asn Asp Asp Val Tyr Asp Gly Phe Pro Gly Gln Gly Leu Leu
               100                 105                 110

Arg Ala Tyr Glu Asn Leu Arg His Trp Leu Arg Gly Asn Ser Lys Arg
            115                 120                 125

Gln Ala Arg Arg Asn Ile Ala Ala His Tyr Asp Leu Gly Asn Asp Phe
        130                 135                 140

Tyr Ala Leu Trp Leu Asp Glu Ser Met Thr Tyr Ser Ser Ala Leu Phe
145                 150                 155                 160

Arg Thr Gly Gln Glu Ser Leu Glu Glu Ala Gln Arg Ala Lys Tyr Ala
                165                 170                 175

Ser Met Val Asp Arg Ile Gly Ala Gln Pro Gly Glu His Val Leu Glu
            180                 185                 190

Ile Gly Cys Gly Trp Gly Gly Phe Ala Glu Tyr Ala Ala Arg Glu Arg
        195                 200                 205

Gly Leu Arg Val Thr Gly Leu Thr Ile Ser Gln Ala Gln His Asp Tyr
    210                 215                 220

Ala Val Glu Arg Ile Ala Arg Ala Gly Leu Ser Asp Arg Val Glu Ile
225                 230                 235                 240

Arg Leu Gln Asp Tyr Arg Asp Glu Arg Gly Ser Phe Asp Gly Ile Ala
                245                 250                 255

Ser Ile Glu Met Phe Glu Ala Val Gly Glu Lys Tyr Trp Pro Val Tyr
            260                 265                 270

Phe Gln Thr Leu Arg Glu Arg Leu Lys Pro Gly Arg Asn Ala Thr Leu
        275                 280                 285

Gln Ile Ile Thr Val Gln Asp Lys Arg Trp Glu Val Tyr Arg Arg Gly
    290                 295                 300
```

```
Val Asp Phe Ile Gln Lys Tyr Ile Phe Pro Gly Gly Met Leu Pro Ser
305                 310                 315                 320

Pro Thr Ala Leu Arg Val Glu Val Ala Lys Ala Gly Leu His Val Thr
                325                 330                 335

Asp Ser Val Glu Phe Gly Glu Ser Tyr Ser Met Thr Leu Arg Arg Trp
            340                 345                 350

His Glu Thr Phe Asn Asp Arg Trp Asp Arg Val Ala Ala Leu Gly Phe
        355                 360                 365

Asp Glu Arg Phe Arg Arg Met Trp Asn Phe Tyr Leu Thr Ser Cys Ala
    370                 375                 380

Gly Ser Phe Asp Gly Gly Asn Cys Asp Val Thr Gln Ile Thr Val Thr
385                 390                 395                 400

Arg Ala Ala

<210> SEQ ID NO 3
<211> LENGTH: 1293
<212> TYPE: DNA
<213> ORGANISM: Rhodobacter sphaeroides

<400> SEQUENCE: 3
```

| | |
|---|---|
| atgccattcg agacgtctga gttcgcgcgg cggcgcgttg cggtgatcgg tggggggcatc | 60 |
| tcggggatgg ctgcggcgca tcttctggcc tccgaccatg cggtcgtgct gttcgaggcc | 120 |
| gagaagcggc tcgggggggca cgcccgcacg gtcctcgcgg gcaagcgcgg cgaccagcct | 180 |
| gtcgacacgg gcttcatcgt gttcaacaag gtgaattatc gcacctcac gcggctcttc | 240 |
| gacgagctcg gcgtgccggt ggcgaagagt gacatgagct tcggcgcctc ggttcgcggc | 300 |
| gggcggctgg aatacggcct caagaacctg aaatccgtct tcgcgcagaa gcgcaacatg | 360 |
| gcggatccgc gcttcctcaa catgatgatg gatgtgctgc gcttcaacgc ccatgcgctc | 420 |
| gaccatgcgg acgatccggc catgacgatc cgcgagctgc tcgcgcggct cgacctcggc | 480 |
| gactggttcc gggactatta cctcctgccg atctcggggg cgatctggtc cacgccctcg | 540 |
| cgcgggatcc tcgacttccc ggcgcaggca ctgctgcgct tcttccagaa ccatgcgctc | 600 |
| ctgtcccata cggggcagca ccagtggttc acggtcgagg gcggctcgat cgaatatgtc | 660 |
| acccggctgc aggccgcgat ggcggcgcgc ggggtggacc tgcgcaccgg ggcgcaggtg | 720 |
| gccggcgtgc gccgcgcgga cggcggggtg cgggtgcggg ccgagggcgg cgagtgggag | 780 |
| gccttcgacg aggtgatctt cgccacccat tccgacgata cgctgcggct tctgtccgat | 840 |
| gcgacggagg ccgagacgag cgcgctcggg ccgtgcgct accagccgaa ccgggcggtg | 900 |
| ctgcattccg atccgtcggt catgccgaag cgcaaggccg cctgggcctc ctgggtctat | 960 |
| gtcgagcctg acgatccgga ggcgcccatc gacatcacct actggatgaa ctcgctgcag | 1020 |
| cccatcccgc aggacgatcc gctgttcgtg acgctgaacg cacccgccc ggtgcgcgag | 1080 |
| gaactggtgc atgatgtggc gaccttccgc cacccggtct acgacctcgc ggcgcagctg | 1140 |
| ggcgtggcgg cgctgcggat gatgaacggc cagcgtcaga cctggttcgc gggcgcctgg | 1200 |
| atgcgcaacg gcttccacga ggatggcttt gccagcgctg tggatgttgt cgaggcgatg | 1260 |
| cgccggcgca ttcccgcctc ggccgcggcc tga | 1293 |

```
<210> SEQ ID NO 4
<211> LENGTH: 430
<212> TYPE: PRT
<213> ORGANISM: Rhodobacter sphaeroides
```

-continued

```
<400> SEQUENCE: 4

Met Pro Phe Glu Thr Ser Glu Phe Ala Arg Arg Val Ala Val Ile
1               5                   10                  15

Gly Gly Gly Ile Ser Gly Met Ala Ala His Leu Leu Ala Ser Asp
                20                  25                  30

His Ala Val Val Leu Phe Glu Ala Glu Lys Arg Leu Gly His Ala
            35                  40                  45

Arg Thr Val Leu Ala Gly Lys Arg Gly Asp Gln Pro Val Asp Thr Gly
        50                  55                  60

Phe Ile Val Phe Asn Lys Val Asn Tyr Pro His Leu Thr Arg Leu Phe
65                  70                  75                  80

Asp Glu Leu Gly Val Pro Val Ala Lys Ser Asp Met Ser Phe Gly Ala
                85                  90                  95

Ser Val Arg Gly Gly Arg Leu Glu Tyr Gly Leu Lys Asn Leu Lys Ser
                100                 105                 110

Val Phe Ala Gln Lys Arg Asn Met Ala Asp Pro Arg Phe Leu Asn Met
            115                 120                 125

Met Met Asp Val Leu Arg Phe Asn Ala His Ala Leu Asp His Ala Asp
130                 135                 140

Asp Pro Ala Met Thr Ile Arg Glu Leu Leu Ala Arg Leu Asp Leu Gly
145                 150                 155                 160

Asp Trp Phe Arg Asp Tyr Tyr Leu Leu Pro Ile Ser Gly Ala Ile Trp
                165                 170                 175

Ser Thr Pro Ser Arg Gly Ile Leu Asp Phe Pro Ala Gln Ala Leu Leu
            180                 185                 190

Arg Phe Phe Gln Asn His Ala Leu Leu Ser His Thr Gly Gln His Gln
        195                 200                 205

Trp Phe Thr Val Glu Gly Gly Ser Ile Glu Tyr Val Thr Arg Leu Gln
210                 215                 220

Ala Ala Met Ala Ala Arg Gly Val Asp Leu Arg Thr Gly Ala Gln Val
225                 230                 235                 240

Ala Gly Val Arg Arg Ala Asp Gly Gly Val Arg Val Arg Ala Glu Gly
                245                 250                 255

Gly Glu Trp Glu Ala Phe Asp Glu Val Ile Phe Ala Thr His Ser Asp
            260                 265                 270

Asp Thr Leu Arg Leu Leu Ser Asp Ala Thr Glu Ala Glu Thr Ser Ala
        275                 280                 285

Leu Gly Ala Val Arg Tyr Gln Pro Asn Arg Ala Val Leu His Ser Asp
290                 295                 300

Pro Ser Val Met Pro Lys Arg Lys Ala Ala Trp Ala Ser Trp Val Tyr
305                 310                 315                 320

Val Glu Pro Asp Asp Pro Glu Ala Pro Ile Asp Ile Thr Tyr Trp Met
                325                 330                 335

Asn Ser Leu Gln Pro Ile Pro Gln Asp Asp Pro Leu Phe Val Thr Leu
            340                 345                 350

Asn Gly Thr Arg Pro Val Arg Glu Glu Leu Val His Asp Val Ala Thr
        355                 360                 365

Phe Arg His Pro Val Tyr Asp Leu Ala Ala Gln Leu Gly Val Ala Ala
370                 375                 380

Leu Arg Met Met Asn Gly Gln Arg Gln Thr Trp Phe Ala Gly Ala Trp
385                 390                 395                 400

Met Arg Asn Gly Phe His Glu Asp Gly Phe Ala Ser Ala Val Asp Val
                405                 410                 415
```

Val Glu Ala Met Arg Arg Ile Pro Ala Ser Ala Ala Ala
              420                 425                 430

<210> SEQ ID NO 5
<211> LENGTH: 750
<212> TYPE: DNA
<213> ORGANISM: Rhodobacter sphaeroides

<400> SEQUENCE: 5

```
atgtgggtcg atcatgtgca gggcgagacc ttccacgggc gcaaggggc gctcggcaac      60
agctttcgct acggggtgga ttatctgctg atcgatcccg aggcggtgga ggggccggcg    120
ctcttctcgc gcaaccgggc caacctcatc tcgctccacg atcgcgacta cggcggtgcg    180
ccgggcgagg gacggggcgc agcgtgggtg cgcgaggtgc tggcggcgca ggggctgccg    240
cccgccgcgc gcatcctgct gctgacccag ccgcgggtgc tgggccatgt gttcaacccg    300
gtcagcttct ggctctgcga ggatgccgcg gcgcgctcc gctgcgtggt ggccgaggtc     360
agcaacacct tcggcgaccg gcactggtat ctctgcgcca gcccgacgg ctccgtcatc     420
gagcggacgg acacgctcga ggcggccaag atcatgcatg tctcgcccct ccagccgatc    480
gagggcggct atcgcttccg cttcgacatc cgcgaggatc gggtgggcgt ctggatcgac    540
tacagctccg ccgagggcgg gctctatgcc acgcttacgg ccggcgagc gcggctgtcg     600
aaccggggga tcctgcgcgc ctgcctccgg cggcccttcg gtcgcgccg cgtgctggcg     660
ctgatccact ggcaggcgct taagctggcg ctgaaggggg gcgctaccg cagccgcccc    720
gcgccgccgc tgcaagacgt cacgcggtga                                    750
```

<210> SEQ ID NO 6
<211> LENGTH: 249
<212> TYPE: PRT
<213> ORGANISM: Rhodobacter sphaeroides

<400> SEQUENCE: 6

Met Trp Val Asp His Val Gln Gly Glu Thr Phe His Gly Arg Lys Gly
1               5                   10                  15

Ala Leu Gly Asn Ser Phe Arg Tyr Gly Val Asp Tyr Leu Leu Ile Asp
            20                  25                  30

Pro Glu Ala Val Glu Gly Pro Ala Leu Phe Ser Arg Asn Arg Ala Asn
        35                  40                  45

Leu Ile Ser Leu His Asp Arg Asp Tyr Gly Gly Ala Pro Gly Glu Gly
    50                  55                  60

Arg Gly Ala Ala Trp Val Arg Glu Val Leu Ala Ala Gln Gly Leu Pro
65                  70                  75                  80

Pro Ala Ala Arg Ile Leu Leu Leu Thr Gln Pro Arg Val Leu Gly His
                85                  90                  95

Val Phe Asn Pro Val Ser Phe Trp Leu Cys Glu Asp Ala Ala Gly Ala
            100                 105                 110

Leu Arg Cys Val Val Ala Glu Val Ser Asn Thr Phe Gly Asp Arg His
        115                 120                 125

Trp Tyr Leu Cys Ala Lys Pro Asp Gly Ser Val Ile Glu Arg Thr Asp
    130                 135                 140

Thr Leu Glu Ala Ala Lys Ile Met His Val Ser Pro Phe Gln Pro Ile
145                 150                 155                 160

Glu Gly Gly Tyr Arg Phe Arg Phe Asp Ile Arg Glu Asp Arg Val Gly
                165                 170                 175

```
Val Trp Ile Asp Tyr Ser Ser Ala Glu Gly Gly Leu Tyr Ala Thr Leu
            180                 185                 190

Thr Gly Arg Arg Ala Arg Leu Ser Asn Arg Gly Ile Leu Arg Ala Cys
        195                 200                 205

Leu Arg Arg Pro Phe Gly Ser Arg Arg Val Leu Ala Leu Ile His Trp
    210                 215                 220

Gln Ala Leu Lys Leu Ala Leu Lys Gly Ala Arg Tyr Arg Ser Arg Pro
225                 230                 235                 240

Ala Pro Pro Leu Gln Asp Val Thr Arg
                245

<210> SEQ ID NO 7
<211> LENGTH: 1206
<212> TYPE: DNA
<213> ORGANISM: Rhodobacter sphaeroides

<400> SEQUENCE: 7
gtgagtgcgc ggcttctgcc gtggtcgctc ctcgcggggc tgatcgcggc tgccggcctg     60
ccgatctaca tccatgcgcc gaaggtctat gtggacgaat atggcgtgag cctcggcgcg    120
ctggggggcgg tgctggcggg cctgaggctt gtcgatgtgg tgcaggatcc ggccctgggc    180
tggctggccg aggtgacgcg gcagaggcgg gccgccatgg tggcggggc gctcttcctg     240
ctcgcgctgt ccatggtcgg gctcttcgcg gtcgtgccgc cggtggcgcc gctcctgtgg    300
ttcgccctga tgctggtcgt gctgttctct gccttctcct ttctcaccat cgccttctac    360
tccgaaggcg tggccaaggc cggggcggctc ggccccggcg ggcacctgca gctcgcagga    420
tggcgcgagg ccggggcgct cgtgggcgtg tcgcttgcgg cggtggctcc ggtggcgctc    480
ggcagcttcg gcctcttcgc ctggggcttc gcggcctttg cggcggtggc ctggctggcc    540
atgaggcgcg aatggacggg ctcggccgcc gcgccgcagc ccgacctgcg cgcggtgctg    600
cgcgatccga cgatccggcg gcttctcctc ctcgcgctgg tcaatgcggc gccggtggcc    660
gtcacctcca ctttgttcct gttcttcgtc gaaagccgcc tccgcgcccc ggggtccgag    720
gggccgctcc tcctgctttt cttcctcgcg gcggcggcca gtgccccggg ctggagccgc    780
atggcccggc atgtcggagc gaggcgcgcg ctcctcgccg gcatggcgct gtcggtggtc    840
gccttcatct tcgccttcac gctggacgcc ggcgacgtcg cggccttcgc cctgatctgc    900
gcggcctcgg gagcggcgct gggcgcggac atggtgctcc tgcccgcgat cttcgcccgc    960
catctggcgc agagcggggc gggcgaggcc acggccttcg gtctctggtc cttcgcctcg   1020
aagctggcgc tcgccctcgc cgcggcgacg ctgctgcccc tcctgcagcg cgcaggcttc   1080
gagcccggca gcggcgggcc ggccgaggcg ctcatgctcc tgtcggtgct ctatgcgctc   1140
gtgcctgcg gactgaaggc catcgccatc ctcctgctcc ttgccacccc catcccggag   1200
agttga                                                              1206

<210> SEQ ID NO 8
<211> LENGTH: 401
<212> TYPE: PRT
<213> ORGANISM: Rhodobacter sphaeroides

<400> SEQUENCE: 8

Met Ser Ala Arg Leu Leu Pro Trp Ser Leu Leu Ala Gly Leu Ile Ala
1               5                   10                  15

Ala Ala Gly Leu Pro Ile Tyr Ile His Ala Pro Lys Val Tyr Val Asp
            20                  25                  30
```

Glu Tyr Gly Val Ser Leu Gly Ala Leu Gly Ala Val Leu Ala Gly Leu
         35                  40                  45

Arg Leu Val Asp Val Val Gln Asp Pro Ala Leu Gly Trp Leu Ala Glu
 50                  55                  60

Val Thr Arg Gln Arg Arg Ala Ala Met Val Ala Gly Ala Leu Phe Leu
 65                  70                  75                  80

Leu Ala Leu Ser Met Val Gly Leu Phe Ala Val Pro Pro Val Ala
                 85                  90                  95

Pro Leu Leu Trp Phe Ala Leu Met Leu Val Val Leu Phe Ser Ala Phe
                100                 105                 110

Ser Phe Leu Thr Ile Ala Phe Tyr Ser Glu Gly Val Ala Lys Ala Gly
                115                 120                 125

Arg Leu Gly Pro Gly Gly His Leu Gln Leu Ala Gly Trp Arg Glu Ala
 130                 135                 140

Gly Ala Leu Val Gly Val Ser Leu Ala Ala Val Ala Pro Val Ala Leu
 145                 150                 155                 160

Gly Ser Phe Gly Leu Phe Ala Trp Gly Phe Ala Ala Phe Ala Ala Val
                 165                 170                 175

Ala Trp Leu Ala Met Arg Arg Glu Trp Thr Gly Ser Ala Ala Ala Pro
                 180                 185                 190

Gln Pro Asp Leu Arg Ala Val Leu Arg Asp Pro Thr Ile Arg Arg Leu
                 195                 200                 205

Leu Leu Leu Ala Leu Val Asn Ala Ala Pro Val Ala Val Thr Ser Thr
                 210                 215                 220

Leu Phe Leu Phe Phe Val Glu Ser Arg Leu Arg Ala Pro Gly Ser Glu
225                 230                 235                 240

Gly Pro Leu Leu Leu Leu Phe Phe Leu Ala Ala Ala Ser Ala Pro
                 245                 250                 255

Gly Trp Ser Arg Met Ala Arg His Val Gly Ala Arg Arg Ala Leu Leu
                 260                 265                 270

Ala Gly Met Ala Leu Ser Val Val Ala Phe Ile Phe Ala Phe Thr Leu
                 275                 280                 285

Asp Ala Gly Asp Val Ala Ala Phe Ala Leu Ile Cys Ala Ala Ser Gly
 290                 295                 300

Ala Ala Leu Gly Ala Asp Met Val Leu Leu Pro Ala Ile Phe Ala Arg
305                 310                 315                 320

His Leu Ala Gln Ser Gly Ala Gly Glu Ala Thr Ala Phe Gly Leu Trp
                 325                 330                 335

Ser Phe Ala Ser Lys Leu Ala Leu Ala Leu Ala Ala Thr Leu Leu
                 340                 345                 350

Pro Leu Leu Gln Arg Ala Gly Phe Glu Pro Gly Ser Gly Gly Pro Ala
                 355                 360                 365

Glu Ala Leu Met Leu Leu Ser Val Leu Tyr Ala Leu Val Pro Cys Gly
 370                 375                 380

Leu Lys Ala Ile Ala Ile Leu Leu Leu Ala Thr Pro Ile Pro Glu
385                 390                 395                 400

Ser

<210> SEQ ID NO 9
<211> LENGTH: 561
<212> TYPE: DNA
<213> ORGANISM: Rhodobacter sphaeroides

<400> SEQUENCE: 9

```
gtgagttcgt tcctgttcgt ggccctcggc gccctcatcc cccttacgct gctggctctg    60
cgccaccgca tgctctcctt cgccgcgcag cgcccggagg attatgccgc gcaggggccg   120
tcgctcgatc cgcggcggga tctctcgggg ccgatcctct gcgagggcgt cgtctacggg   180
ccgaccgggc gggtcgtctc gcgcttcgtg gccgatgtgg aaggccgctg ggatggcagc   240
tccggggtgc tgaccgagag cttccgctac gacagcggcg cgaccgaccg gcgcgagtgg   300
cgcttcacgc tcggcaatga cggaacgctg cgcgccgagg ccgacgatgt ggtgggcgtg   360
ggcctcggac gggccctcgg atcggcgctc tgcctgcgct accggctgcg gcttcaagat   420
gacgcagggg gccatgtgct ggacgtcatt gactggatgt accggctgga gaatggcacg   480
atcatcaatc ggagccagtt ccgtaagttc gggatcaagg tggccgagct tgtggcgaca   540
ctgagacgga tcgagagatg a                                             561
```

<210> SEQ ID NO 10
<211> LENGTH: 186
<212> TYPE: PRT
<213> ORGANISM: Rhodobacter sphaeroides

<400> SEQUENCE: 10

```
Met Ser Ser Phe Leu Phe Val Ala Leu Gly Ala Leu Ile Pro Leu Thr
1               5                   10                  15

Leu Leu Ala Leu Arg His Arg Met Leu Ser Phe Ala Ala Gln Arg Pro
            20                  25                  30

Glu Asp Tyr Ala Ala Gln Gly Pro Ser Leu Asp Pro Arg Arg Asp Leu
        35                  40                  45

Ser Gly Pro Ile Leu Cys Glu Gly Val Val Tyr Gly Pro Thr Gly Arg
    50                  55                  60

Val Val Ser Arg Phe Val Ala Asp Val Glu Gly Arg Trp Asp Gly Ser
65                  70                  75                  80

Ser Gly Val Leu Thr Glu Ser Phe Arg Tyr Asp Ser Gly Ala Thr Asp
                85                  90                  95

Arg Arg Glu Trp Arg Phe Thr Leu Gly Asn Asp Gly Thr Leu Arg Ala
            100                 105                 110

Glu Ala Asp Asp Val Val Gly Val Gly Leu Gly Arg Ala Leu Gly Ser
        115                 120                 125

Ala Leu Cys Leu Arg Tyr Arg Leu Arg Leu Gln Asp Asp Ala Gly Gly
    130                 135                 140

His Val Leu Asp Val Ile Asp Trp Met Tyr Arg Leu Glu Asn Gly Thr
145                 150                 155                 160

Ile Ile Asn Arg Ser Gln Phe Arg Lys Phe Gly Ile Lys Val Ala Glu
                165                 170                 175

Leu Val Ala Thr Leu Arg Arg Ile Glu Arg
            180                 185
```

<210> SEQ ID NO 11
<211> LENGTH: 738
<212> TYPE: DNA
<213> ORGANISM: Rhodobacter sphaeroides

<400> SEQUENCE: 11

```
atgagagact ttgtaggtaa gcggtattgg ctcatcggcg gcagcgaggg cctcggtctc    60
gcgctggcga agaaactgag cggcgcgggg gcgaaggtga tcctgtcggg tcgcgacgag   120
gcccggctgg cagaggccgt ggcggccatg ccggcgcccg ccgaggcggt caccctcgac   180
gtgacctccg aggcctcgat cgaggcggcg ctcgcgcagg tcggcgcctt cgacggggtg   240
```

```
gtctacctcg ccggcgccta ctggccgatg aaggcgcagg cctggaggc gagccgggtc    300 gaggcgatga tcgacacgaa ccttctgggg ctcgtgcggc ttctgtcggc ggtgcttccg    360
ggcatgatcg ctgcgaaccg cggccatctg gtggtgacgg gcagcatcgg cggctatcgc    420
ggcctgccgg cgccatcgg ctattcggcc agcaaggcag gcgtgatggc cctgaccgag    480
tcgctctatg ccgatctgcg cgacacgggc gtcgaggtgc agctcgtgaa cccgggcttc    540
atccgcacgc ggctgaccga gaagaaccgg ttccgcatgc ccttcatcat ggagcccgag    600
gcggccgcgc agcggatgtt cgaacatatg tgcgcggaca atttccgtgc caacttcccg    660
gtgctcttcg cctcgttctt ccgcttctcg cagctcctgc cggacgggct gttctaccgg    720
ctgctcggca agggctga                                                  738
```

<210> SEQ ID NO 12
<211> LENGTH: 245
<212> TYPE: PRT
<213> ORGANISM: Rhodobacter sphaeroides
<400> SEQUENCE: 12

```
Met Arg Asp Phe Val Gly Lys Arg Tyr Trp Leu Ile Gly Gly Ser Glu
1               5                   10                  15

Gly Leu Gly Leu Ala Leu Ala Lys Lys Leu Ser Gly Ala Gly Ala Lys
            20                  25                  30

Val Ile Leu Ser Gly Arg Asp Glu Ala Arg Leu Ala Glu Ala Val Ala
        35                  40                  45

Ala Met Pro Ala Pro Ala Glu Ala Val Thr Leu Asp Val Thr Ser Glu
    50                  55                  60

Ala Ser Ile Glu Ala Ala Leu Ala Gln Val Gly Ala Phe Asp Gly Val
65                  70                  75                  80

Val Tyr Leu Ala Gly Ala Tyr Trp Pro Met Lys Ala Gln Ala Trp Glu
                85                  90                  95

Ala Ser Arg Val Glu Ala Met Ile Asp Thr Asn Leu Leu Gly Leu Val
            100                 105                 110

Arg Leu Leu Ser Ala Val Leu Pro Gly Met Ile Ala Ala Asn Arg Gly
        115                 120                 125

His Leu Val Val Thr Gly Ser Ile Gly Gly Tyr Arg Gly Leu Pro Gly
    130                 135                 140

Ala Ile Gly Tyr Ser Ala Ser Lys Ala Gly Val Met Ala Leu Thr Glu
145                 150                 155                 160

Ser Leu Tyr Ala Asp Leu Arg Asp Thr Gly Val Glu Val Gln Leu Val
                165                 170                 175

Asn Pro Gly Phe Ile Arg Thr Arg Leu Thr Glu Lys Asn Arg Phe Arg
            180                 185                 190

Met Pro Phe Ile Met Glu Pro Glu Ala Ala Ala Gln Arg Met Phe Glu
        195                 200                 205

His Met Cys Ala Asp Asn Phe Arg Ala Asn Phe Pro Val Leu Phe Ala
    210                 215                 220

Ser Phe Phe Arg Phe Ser Gln Leu Leu Pro Asp Gly Leu Phe Tyr Arg
225                 230                 235                 240

Leu Leu Gly Lys Gly
                245
```

<210> SEQ ID NO 13
<211> LENGTH: 213
<212> TYPE: PRT

<213> ORGANISM: Rhodobacter sphaeroides

<400> SEQUENCE: 13

Met Thr Ile Arg His His Val Ser Asp Ala Leu Leu Thr Ala Tyr Ala
1               5                   10                  15

Ala Gly Thr Leu Ser Glu Ala Phe Ser Leu Val Val Ala Thr His Leu
            20                  25                  30

Ser Leu Cys Asp Glu Cys Arg Ala Arg Ala Gly Ala Leu Asp Ala Val
        35                  40                  45

Gly Gly Ser Leu Met Glu Thr Ala Pro Val Ala Leu Ser Glu Gly
    50                  55                  60

Ser Leu Ala Ser Val Met Ala Gln Leu Asp Arg Gln Ile Gln Arg Pro
65                  70                  75                  80

Ala Pro Ala Arg Arg Ala Asp Pro Arg Ala Pro Ala Pro Leu Ala Asp
                85                  90                  95

Tyr Val Gly Arg Arg Leu Glu Asp Val Arg Trp Arg Thr Leu Gly Gly
            100                 105                 110

Gly Val Arg Gln Ala Ile Leu Pro Thr Gly Gly Glu Ala Ile Ala Arg
        115                 120                 125

Leu Leu Trp Ile Pro Gly Gly Gln Ala Val Pro Asp His Gly His Arg
    130                 135                 140

Gly Leu Glu Leu Thr Leu Val Leu Gln Gly Ala Phe Arg Asp Glu Thr
145                 150                 155                 160

Asp Arg Phe Gly Ala Gly Asp Ile Glu Ile Ala Asp Gln Glu Leu Glu
                165                 170                 175

His Thr Pro Val Ala Glu Arg Gly Leu Asp Cys Ile Cys Leu Ala Ala
            180                 185                 190

Thr Asp Ala Pro Leu Arg Phe Asn Ser Phe Leu Pro Lys Leu Val Gln
        195                 200                 205

Pro Phe Phe Arg Ile
    210

<210> SEQ ID NO 14
<211> LENGTH: 181
<212> TYPE: PRT
<213> ORGANISM: Rhodobacter sphaeroides

<400> SEQUENCE: 14

Met Thr Asp Lys Ser Asp Arg Thr Asp Trp Val Ala Leu Met Arg Ala
1               5                   10                  15

Ile Arg Asp His Arg Asp Glu Ala Ala Phe Ala Glu Leu Phe Gln His
            20                  25                  30

Phe Ala Pro Lys Val Lys Gly Phe Leu Met Lys Ser Gly Ser Val Ala
        35                  40                  45

Ser Gln Ala Glu Glu Cys Ala Gln Asp Val Met Ala Thr Val Trp Gln
    50                  55                  60

Lys Ala His Leu Phe Asp Pro Ser Arg Ala Ser Val Ala Thr Trp Ile
65                  70                  75                  80

Phe Thr Ile Ala Arg Asn Arg Arg Ile Asp Gly Leu Arg Lys Asp Arg
                85                  90                  95

Gln Pro Glu Pro Glu Asp Leu Phe Trp Gly Pro Asp Ser Glu Pro Asp
            100                 105                 110

Gln Ala Asp Val Tyr Glu Met Gln Gln Glu Asn Ala Arg Leu Gly Arg
        115                 120                 125

Ala Ile Ala Arg Leu Pro Glu Ala Gln Arg Ala Leu Ile Glu Arg Ala

```
                130                 135                 140
Phe Phe Gly Asp Leu Thr His Arg Glu Leu Ala Ala Glu Thr Gly Leu
145                 150                 155                 160

Pro Leu Gly Thr Ile Lys Ser Arg Ile Arg Leu Ala Leu Asp Arg Leu
                165                 170                 175

Arg Gln His Met Ser
            180

<210> SEQ ID NO 15
<211> LENGTH: 409
<212> TYPE: PRT
<213> ORGANISM: Rhodopseudomonas palustris

<400> SEQUENCE: 15

Met Ser Glu Leu Val Ala Leu Thr Pro Asp Asn Val Asp Asp Arg Val
1               5                   10                  15

Ala Asp Leu Pro Arg Val Val Arg Met Ala Leu Ala Phe Gly Ala Arg
                20                  25                  30

Leu Gln Arg Gly Thr Leu Asp Val Thr Leu Pro Asp Gly Arg Arg Phe
            35                  40                  45

Arg Leu Gly Gly Ala Glu Pro Gly Pro Ala Ala Glu Met Arg Leu His
50                  55                  60

Ser Tyr Gly Phe Ala Ser Arg Leu Ile His Gly Gly Asp Ile Gly Ile
65                  70                  75                  80

Ala Glu Ala Tyr Leu Asn Arg Glu Trp Asp Thr Pro Asp Leu Thr Gln
                85                  90                  95

Phe Leu Tyr Leu Phe Cys Val Asn His Glu Met Ile Gln Ala Met Leu
            100                 105                 110

Ala Asp Asn Pro Leu Met Arg Leu Val Gln Met Val Arg His Trp Phe
        115                 120                 125

Asn Arg Asn Thr Lys Arg Gln Ala Arg Lys Asn Ile Tyr Ala His Tyr
130                 135                 140

Asp Ile Gly Asn Glu Phe Tyr Ser Ala Trp Leu Asp Pro Ser Met Thr
145                 150                 155                 160

Tyr Ser Ser Ala Leu Phe Glu Asp His Thr His Asp Leu Thr Ala Ala
                165                 170                 175

Gln Ile Asn Lys Tyr Gln Arg Leu Ala Glu Ala Ile Asp Leu Lys Pro
            180                 185                 190

Gly Gln Ser Val Leu Glu Ile Gly Cys Gly Trp Gly Gly Phe Ala Glu
        195                 200                 205

Tyr Ala Ala Lys Thr Phe Asp Val Arg Leu Val Gly Leu Thr Ile Ser
210                 215                 220

Arg Glu Gln Arg Asp Phe Ala Gln Gln Arg Met Phe Glu Ala Gly Leu
225                 230                 235                 240

Ala Asp Lys Val Glu Ile Lys Leu Gln Asp Tyr Arg Asp Glu Arg Gly
                245                 250                 255

Arg Tyr Asp Arg Ile Ala Ser Ile Glu Met Ile Glu Ala Val Gly Glu
            260                 265                 270

Glu Phe Trp Pro Lys Tyr Phe Ser Gln Leu Arg Asp Arg Leu Met Pro
        275                 280                 285

Gly Gly Leu Val Gly Ile Gln Ala Ile Thr Ile Gln Asp Arg Phe Phe
290                 295                 300

Gln Thr Tyr Arg Arg Glu Val Asp Phe Ile Gln Arg Tyr Val Phe Pro
305                 310                 315                 320
```

```
Gly Gly Met Leu Pro Ser Pro Gly Val Leu Lys Ser Leu Gly Glu Thr
            325                 330                 335

Phe Gly Val Pro Val Val Arg Glu Arg Val Phe Gly Glu Asp Tyr Ala
            340                 345                 350

Lys Thr Leu Ala Thr Trp Arg Asp Asn Phe Arg Ala Ala Trp Pro Lys
            355                 360                 365

Leu Arg Ser Gln Gly Phe Asp Asp Arg Phe Arg Leu Trp Glu Tyr
    370                 375                 380

Tyr Leu Ser Tyr Cys Glu Ala Gly Phe Leu Ser Gly Asn Ile Asp Val
385                 390                 395                 400

Arg Gln Val Val Phe Ala Lys Ala Gly
                405
```

<210> SEQ ID NO 16
<211> LENGTH: 437
<212> TYPE: PRT
<213> ORGANISM: Rhodopseudomonas palustris

<400> SEQUENCE: 16

```
Met Arg Val Ala Ile Val Gly Thr Gly Ile Ala Gly Asn Ala Ala Ala
1               5                   10                  15

Trp Ala Leu Ser Gln Arg Tyr Pro Val Thr Val Tyr Glu Arg Glu Leu
            20                  25                  30

Arg Ala Gly Gly His Ser His Thr Val Thr Val Asp Tyr Asp Gly Thr
            35                  40                  45

Thr Ile Pro Val Asp Ile Gly Phe Ile Val Tyr Asn Gln Leu Asn Tyr
    50                  55                  60

Pro Asp Leu Thr Ala Met Phe Ala His Leu Gly Val Glu Thr Val Glu
65                  70                  75                  80

Ser Cys Met Ser Phe Ser Val Ser Ala Asp Ala Gly Arg Phe Glu Trp
                85                  90                  95

Lys Gly Gly Gly Ser Asn Trp Leu Glu Thr Ala Asp Gly Leu Phe Ala
            100                 105                 110

Gln Arg Arg Asn Leu Leu Ser Pro Ser Tyr Leu Gln Met Leu Arg His
            115                 120                 125

Ile Leu Val Phe Asn Glu Lys Ser Val Glu Asp Phe Lys Thr Gly Ala
    130                 135                 140

Leu Ala Gly Leu Thr Leu Gly Asp Tyr Phe Glu Ser Arg Lys Phe Ala
145                 150                 155                 160

Pro Arg Leu Leu Thr Asp Tyr Leu Ala Pro Met Gly Ala Ala Ile Trp
                165                 170                 175

Ser Ala Pro Ala Ser Gln Ile Leu Asp Phe Pro Ala Glu Asn Phe Val
            180                 185                 190

Ala Phe Phe Asn Asn His Arg Leu Leu His Tyr Glu Arg Pro Ile Trp
            195                 200                 205

Arg Thr Val Lys Gly Gly Ser Ala Arg Tyr Val Glu Lys Leu Thr Ser
    210                 215                 220

Ala Phe Lys Asp Asp Met Arg Leu Gly Ala Ala Val Thr Ser Ile Glu
225                 230                 235                 240

Arg Ser Pro Lys Gly Val Ile Arg Asp Ser Leu Gly Gly Leu Gly
                245                 250                 255

Val Phe Asp His Val Val Ile Gly Ala His Ser Asp Gln Ala Leu Ala
            260                 265                 270

Met Leu Ser Asp Ala Ser Asp Ile Glu Arg Asp Ile Leu Gly Ser Ile
            275                 280                 285
```

```
Gly Tyr Ala Pro Asn Met Val Tyr Leu His Arg Asp Pro Arg Leu Met
            290                 295                 300

Pro Lys Arg Lys Arg Ala Trp Ala Ser Trp Asn Phe Leu Arg Trp Gln
305                 310                 315                 320

Arg Glu Gly Ser Pro Val Asn Asp Val Ala Val Thr Tyr Trp Met Asn
                325                 330                 335

Arg Leu Gln Gly Ile Asp Ala Asp Lys Pro Leu Phe Val Ser Leu Asn
            340                 345                 350

Pro Pro Phe Glu Pro Ala Pro Glu Leu Thr Phe Gly Arg Tyr Ala Cys
        355                 360                 365

Asp His Pro Gln Tyr Thr Ala Lys Ala Phe Ala Ala Gln Arg Arg Val
    370                 375                 380

Gly Glu Leu Gln Gly His Arg Asn Thr Trp Phe Cys Gly Ala Trp Thr
385                 390                 395                 400

Gly Tyr Gly Phe His Glu Asp Gly Leu Arg Ser Gly Leu Ala Val Ala
                405                 410                 415

Glu His Leu Gly Ala Pro Val Pro Trp Arg Gly Pro Ser Glu Phe
            420                 425                 430

Arg Glu Ala Ala Glu
            435

<210> SEQ ID NO 17
<211> LENGTH: 281
<212> TYPE: PRT
<213> ORGANISM: Rhodopseudomonas palustris

<400> SEQUENCE: 17

Met Ala Leu Leu Ala Ala Asn Thr Ser Pro Ser Leu Gly Ala Pro Pro
1               5                   10                  15

Ala Ala Ala Ala Ser Leu Tyr Val Gly Glu Val Met His Ala Arg Leu
                20                  25                  30

Lys Pro Val Gly His Arg Phe Gln Tyr Arg Val Met Ser Leu Leu Ile
            35                  40                  45

Asp Leu Asp Arg Leu Asp Glu Ala Asp Arg Met Ser Pro Leu Phe Gly
50                  55                  60

Val Asn Arg Arg Ala Leu Tyr Ser Phe His Glu Ala Asp His Gly Pro
65                  70                  75                  80

Arg Asp Ala Ser Ser Leu Arg Ala Tyr Ala Gln Ala Ser Ala Glu Ala
                85                  90                  95

Lys Gly Val Asp Leu Thr Gly Gly Arg Val Leu Leu Thr Tyr Pro
            100                 105                 110

Arg Ile Ala Gly Tyr Thr Phe Asn Pro Leu Ser Val Tyr Phe Cys Tyr
            115                 120                 125

Asp Ala Ser Gly Ala Leu Ala Val Ile Tyr Glu Val Arg Asn Thr
130                 135                 140

Phe Gly Asp Ile His Pro Tyr Val Leu Pro Val His Ala Gly Glu Met
145                 150                 155                 160

Gly Pro Ala Gly Leu Arg Gln Glu Gln Asp Lys Leu Phe Tyr Val Ser
                165                 170                 175

Pro Phe Ile Glu Met Ala Met Arg Tyr His Phe Arg Ile Val Pro Pro
            180                 185                 190

Gly Glu Ile Val Arg Leu Arg Ile Leu Glu Thr Asp Val Asp Gly Pro
        195                 200                 205

Val Leu Ala Ala Thr Phe Ala Gly Thr His Arg Val Leu Ser Thr Ala
```

```
            210                 215                 220
Ser Leu Leu Gln Ala Phe Leu Ala Leu Pro Leu Met Thr Leu Lys Val
225                 230                 235                 240

Ile Ala Ala Ile His Trp Glu Ala Leu Arg Leu Trp Ile Lys Gly Ala
                245                 250                 255

Lys Leu Val Pro Arg Pro Ala Pro Pro Ser Pro Pro Thr Gly Phe Ala
                260                 265                 270

Ala Gly Gly His Asp Ala Tyr Thr His
                275                 280

<210> SEQ ID NO 18
<211> LENGTH: 257
<212> TYPE: PRT
<213> ORGANISM: Rhodopseudomonas palustris

<400> SEQUENCE: 18

Met Arg Leu Ser Gly Lys Thr Ala Leu Ile Thr Gly Gly Asn Ser Gly
1               5                   10                  15

Ile Gly Leu Ala Thr Ala Lys Leu Phe Val Thr Glu Gly Ala Arg Val
                20                  25                  30

Thr Ile Thr Gly Arg Asp Arg Ala Arg Leu Asp Ala Ala Ala Arg Glu
            35                  40                  45

Leu Gly Ala Gln Ala Leu Ala Val Glu Ala Asp Val Thr Asp Val Ala
        50                  55                  60

Ala Ile Glu Asn Ala Val Ala Arg Ala Glu Arg Phe Gly Lys Leu
65                  70                  75                  80

Asp Ile Val Phe Ala Asn Ala Gly Ile Pro Gly Ala Thr Pro Leu Gly
                85                  90                  95

Gly Thr Ser Leu Ala Ala Phe Glu Gln Val Ile Arg Thr Asn Leu Thr
            100                 105                 110

Ala Val Phe Phe Thr Val Gln Ala Ala Leu Pro Tyr Leu Asn Asp Gly
        115                 120                 125

Ala Ser Ile Ile Leu Asn Gly Ser Val Ile Ser Val Leu Gly Asn Pro
    130                 135                 140

Gly Phe Ala Ala Tyr Ala Ala Ser Lys Ala Gly Leu Arg Gly Met Ala
145                 150                 155                 160

Arg Val Met Ala Ser Glu Leu Ser Pro Arg Asn Ile Arg Val Asn Val
                165                 170                 175

Val Ala Pro Gly Gly Ala Arg Thr Pro Ile Trp Lys Asp Thr Ala Pro
            180                 185                 190

Thr Asp Gln Ala Met Ala Val Leu Glu Lys Arg Ile Ala Ala Ala Thr
        195                 200                 205

Pro Leu Gly Arg Ile Ala Glu Pro Glu His Ile Ala Lys Thr Val Leu
    210                 215                 220

Phe Leu Ala Ser Asp Asp Ala Ala His Ile Gln Ser Ala Glu Ile Phe
225                 230                 235                 240

Val Asp Gly Gly Ala Thr Gly Ser Pro Ala Gly Val Pro Ala Phe Arg
                245                 250                 255

Ser
```